(12) United States Patent
Ogiso et al.

(10) Patent No.: US 7,259,260 B2
(45) Date of Patent: Aug. 21, 2007

(54) IMIDE COMPOUND AND OPTICAL RECORDING MEDIA MADE BY USING THE SAME

(75) Inventors: Akira Ogiso, Sodegaura (JP); Hiroyoshi Shiozaki, Sodegaura (JP); Tsutomu Ishida, Sodegaura (JP)

(73) Assignee: Mitsui Chemicals, Inc., Tokyo (JP)

(*) Notice: Subject to any disclaimer, the term of this patent is extended or adjusted under 35 U.S.C. 154(b) by 50 days.

(21) Appl. No.: 10/493,034

(22) PCT Filed: Oct. 22, 2002

(86) PCT No.: PCT/JP02/10939

§ 371 (c)(1),
(2), (4) Date: Apr. 19, 2004

(87) PCT Pub. No.: WO03/035407

PCT Pub. Date: May 1, 2003

(65) Prior Publication Data

US 2005/0208425 A1   Sep. 22, 2005

(30) Foreign Application Priority Data

May 22, 2001 (JP) ............................ 2002-147538
Oct. 22, 2001 (JP) ............................ 2001-323900
Nov. 9, 2001 (JP) ............................ 2001-344742
Jul. 19, 2002 (JP) ............................ 2002-210949
Aug. 26, 2002 (JP) ............................ 2002-244776
Aug. 27, 2002 (JP) ............................ 2002-246872

(51) Int. Cl.
*C07D 239/72* (2006.01)

(52) U.S. Cl. ............... 544/286; 430/270.16; 546/2; 548/402

(58) Field of Classification Search .......... 430/270.16; 546/2; 548/402; 544/286
See application file for complete search history.

(56) References Cited

U.S. PATENT DOCUMENTS 5,026,625 A   6/1991 Biediker et al.
5,886,183 A   3/1999 Langhals et al.

FOREIGN PATENT DOCUMENTS

| JP | 61-179792 | 8/1986 |
| JP | 05-214331 | 8/1993 |
| JP | 6-332173 | * 12/1994 |
| JP | 08-118800 | 5/1996 |
| JP | 10-147062 | 6/1998 |
| JP | 10-244755 | 9/1998 |
| JP | 11-348424 | 12/1999 |
| JP | 2001-047740 | 2/2001 |
| JP | 2001-165894 | 6/2001 |
| WO | 97/23354 | 7/1997 |

OTHER PUBLICATIONS

Wang et al, Registry No. 227618-02-2, 2000.*
Wang et al, Registry No. 226346-33-2, 2000.*
Bildstein et al, Organometallics, 1999, vol. 18, pp. 4325-4336.*
Emilia et al, J. of Organometallic Chemistry, vol. 480, 1994, 81-90.*
Richard C. Cambie et al., Towards the synthesis of aminodibenzo[b,e][1,4]dioxin derivatives via cationic ruthenium complexes, *Journal of Organometallic Chemistry*, 1996, pp. 1-21, vol. 507, Elsevier Science, S.A.
Attila C. Bényei et al., "Functionalised acyl ferrocenes: crystal and molecular structures of 4-aminobenzoylferrocene, 4-hydroxybenzoylferrocene and 1,1'-bis(4-hydroxybenzoyl) ferrocene", *Journal of Organometallic Chemistry*, 1997, pp. 177-186, vol. 539, Elsevier Science S.A.

* cited by examiner

*Primary Examiner*—Shailendra Kumar
(74) *Attorney, Agent, or Firm*—Buchanan Ingersoll & Rooney PC

(57) ABSTRACT

An optical recording medium containing one or more compounds selected from imide compounds having a metallocene residue in a recording layer and an imide compound represented by a general formula (1):

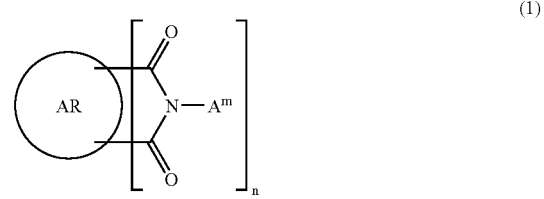

wherein a ring AR represents a substituted or unsubstituted aromatic ring residue or a residue formed by combining two or more aromatic ring residues via one or more linking groups; n represents the number of imide groups bonded to the ring AR; $A^m$ represents any one of substituents $A^1$ to $A^n$ bonded to a nitrogen atom of each imide group; and m represents an integer of from 1 to n, with the proviso that at least one substituent selected from the group consisting of $A^1$ to $A^n$ is one having at least one substituted or unsubstituted metallocene residue.

3 Claims, 4 Drawing Sheets

IMIDE COMPOUND AND OPTICAL RECORDING MEDIA MADE BY USING THE SAME

This application is a 371 of PCT/JP02/10939, filed Oct. 22, 2002.

TECHNICAL FIELD

The present invention relates to an optical recording medium, and more specifically, an optical recording medium capable of writing and reading by a visible laser, a blue laser beam. In addition, the present invention relates to a novel imide compound.

BACKGROUND ART

As a recordable optical recording medium corresponding to the specifications of a compact disk (hereinafter simply referred to as a "CD"), a CD-R (CD-Recordable) has been widely spread. The storage capacity of the CD-R is about 680 MB. However, with a drastic increase of the information volume, demands for higher density and larger storage capacity in an information recording medium have been increased.

As a means for achieving higher density of a recording medium, it is considered to decrease a beam spot by using a shorter-wavelength laser in writing and reading and increasing a numerical aperture (N.A.) of an object lens. As the short-wavelength laser for use in an optical disk system, red laser beams of 500 to 700 nm, further 630 to 690 nm, more specifically, 680, 670, 660, 650, and 635 nm have been put to practical use. Thus, by virtue of techniques for reducing the wavelength of a semiconductor laser, increasing the numerical aperture of an object lens, and compressing data, an optical recording medium capable of recording a motion picture and large volumetric information has been successfully produced. Examples of optical recording media proposed up to the present include a magneto-optical recording medium, phase change recording medium, chalcogen oxide-based optical recording medium, and organic dye-based optical recording medium. Of them, the organic dye-based optical recording medium is considered preferential in view of low cost and easy processing. In consideration of these circumstances, the one developed as an optical recording medium capable of recording and regenerating a motion picture with the same quality level as that of TV and with a higher density than that of CD and as a recordable optical recording medium capable of regenerating by a commercially available DVD video player or a DVD-ROM player that have been widely used and capable of recording by a red semiconductor laser having an oscillation wavelength of 630 to 690 nm is a recordable digital versatile disc (hereinafter, simply referred to as a "DVD-R"). DVD-R is a write-once optical recording medium having a 3.9 or 4.7 GB storage capacity. In particular, only recently, a DVD-R medium having a single-side capacity of 4.7 GB has been brought into a market. Such a DVD-R medium also employs a stacked structure, which is formed of a recording layer containing a cyanine-based dye, azo-based dye, or the like, and a reflecting layer, is characterized by a disk structure formed by adhering two substrates of 0.6 mm thick. Regarding such an optical disk having satisfactory recording characteristics suitable for this capacity, development of a medium applicable to high-speed recording has been aggressively made at present.

Furthermore, it has been estimated that a further higher density recording will be desired in future and that the amount of data stored in a single disk will reach up to 15 to 30 GB. To attain such a recording density, a further shorter-wavelength laser will be inevitably used. Accordingly, as a recording dye suitable for an on-coming organic dye-based optical recording medium, it is desired to develop a dye having good recording characteristics within the wavelength range of 300 to 500 nm.

In the meantime, regarding a medium attaining high-density recording more excellent than DVD-R using an organic dye in a recording layer, Japanese Patent Laid-Open No. 10-302310 discloses that a recording density having a storage capacity of 8 GB or more is attained by using a laser having an oscillation wavelength of 680 nm or less. This publication suggests that a large storage capacity of 8 GB or more should be attained by converging laser light of 680 nm or less through an object lens having a high numerical aperture of 0.7 or more via a light transmission layer of 10 to 177 μm thick.

On the other hand, only in recent years, as a blue laser having an oscillation wavelength of 390 to 430 nm, a laser of 410 nm using a GaN-based material and an SHG laser of 425 nm wavelength, which is obtained by combining a semiconductor laser and an optical wave guide element, have been developed (for example, January 26 Issue of Nikkei Electronics, No. 708, p. 117, 1998). Thus, development of blue semiconductor laser applicable dyes suitably used in such a laser is now proceeding.

Furthermore, Nichia Corporation started supply of a GaN-based semiconductor laser emitting bluish-violet light having an oscillation wavelength of 400 to 410 nm from the beginning of 1999. Since then, studies on a medium having a high-density storage capacity of 15 GB or more per side (hereinafter referred to as an "HD-DVD-R medium") and capable of recording a motion picture having the same image-quality level as that of a high definition television (HDTV) for about 2 hours have been started. Such an HD-DVD-R medium is capable of recording motion pictures for about 6 hours with the same image-quality level as those currently on air and therefore attracted attention also as a new recording medium in place of a home VTR. Already now, technical outline of a proposal for a medium using an inorganic recording film of a phase change system has been introduced in September 6 Issue of Nikkei Electronics, No. 751, p. 117 (1999).

The organic dye compounds for use in recording by a blue laser of 400 to 500 nm currently proposed include cyanine-based dye compounds described in Japanese Patent Laid-Open Nos. 4-74690, 6-40161, 2001-232945, 2001-246851, 2001-260536, and 2001-301333; porphyrin-based dye compounds described in Japanese Patent Laid-Open Nos. 7-304256, 7-304257, 8-127174, 11-334207, 2001-39032, 2001-80217, 2001-84594, 2001-138633, 2001-138634, 2001-143317, 2001-180117, 2001-181524, and 2001-287462; polyene-based dye compounds described in Japanese Patent Laid-Open Nos. 4-78576 and 4-89279; azo-based dye compounds described in Japanese Patent Laid-Open Nos. 11-334204, 11-334205 and 2001-271001; dicyanovinylphenyl dye compounds described in Japanese Patent Laid-Open No. 11-304206; coumarin compounds described in Japanese Patent Laid-Open Nos. 2000-43423 and 2001-96918; pyrimidine compounds described in Japanese Patent Laid-Open No. 2000-163799; naphthalocyanine compounds described in Japanese Patent Laid-Open No. 2000-228028; five-membered hetero ring compounds described in Japanese Patent Laid-Open No. 2000-335110;

bis-azole compounds described in Japanese Patent Laid-Open No. 2000-343824; amino pyridine compounds described in Japanese Patent Laid-Open No. 2000-343825; bis-pyridinium compounds described in Japanese Patent Laid-Open No. 2001-63211; oxonol compounds described in Japanese Patent Laid-Open Nos. 2001-71638 and 2001-328351; styryl compounds described in Japanese Patent Laid-Open Nos. 2001-71639 and 2002-2110; amino butadiene compounds described in Japanese Patent Laid-Open No. 2001-146074; metal chelate compounds described in Japanese Patent Laid-Open Nos. 2001-158862, 2001-214084, and 2002-36727; quinone or quinodimethane compounds described in Japanese Patent Laid-Open No. 2001-232944; hydrazone compounds described in Japanese Patent Laid-Open No. 2001-234154; triazine compounds described in Japanese Patent Laid-Open No. 2001-277720; carbostyryl compounds or naphthylidine compounds described in Japanese Patent Laid-Open No. 2001-287466; condensed heterocyclic compounds described in Japanese Patent Laid-Open No. 2001-301329; and stilbene compounds described in Japanese Patent Laid-Open No. 2002-2117.

Further, the optical recording media are proposed including an optical recording medium described in Japanese Patent Laid-Open No. 11-53758, which is formed of two layers: one is a recording layer primarily containing a porphyrin-based dye or cyanine-based dye as an organic dye for forming the recording layer and the other is a metal reflecting layer primarily containing silver; an optical recording medium described in Japanese Patent Laid-Open No. 11-203729 which attains writing in 2 wavelength regions by devising the constitution of a medium, that is, using a medium having a blue laser responsive dye layer containing a cyanine-based dye responsible to a blue laser and a red laser responsive dye layer; an optical recording medium using an indigoid-based dye compound described in Japanese Patent Laid-Open No. 11-78239 which attaining writing in two wavelength regions by mixing two types of dyes, that is, a dye for a blue laser and a dye for a red laser; an optical recording medium using a cyanoethene-based dye described in Japanese Patent Laid-Open No. 11-105423; and an optical recording medium using a squarylium-based dye compound described in Japanese Patent Laid-Open No. 11-110815.

On the other hand, as examples for using an organic dye film for writing within the blue region of 400 to 500 nm, Japanese Patent Laid-Open Nos. 7-304256 and 7-304257 have suggested to mix a molecular compound coordinated to the central metal of a porphyrin-based compound and a polymer or a polymer having a molecular structure having a central metal coordinated as a side chain, thereby shifting the Soret zone of the porphyrin-based compound toward a long wavelength range so as to correspond to an Ar laser of 488 nm, and simultaneously to reduce manufacturing cost by achieving film formation by spin coating. Furthermore, Japanese Patent Laid-Open Nos. 4-78576 and 4-89279 disclose polyene-based color compounds, which are, however, poor in light stability according to the studies by the present inventors, and required some modifications, for example, blending of a quencher or the like, to put them to practical use.

As the recent circumstances, since the prospect of putting a bluish-violet semiconductor laser of 400 to 410 nm wavelength to practical use is given, development of a high-capacity recordable optical recording medium using the laser has been aggressively made and particularly development of dyes having excellent light stability and high-speed recording characteristics has been desired.

However, the optical recording media mentioned above are actually insufficient to be subjected to the laser light having a wavelength of 400 to 410 nm. More specifically, the media using the organic dyes mentioned above have a problem in that when recorded signal data is read out, the read-out of a signal is not satisfactory performed, since the ratio of carrier to noise (C/N) is not always proper. Therefore, development of an optical recording medium capable of overcoming this problem and writing and reading high-density data by a laser beam of 400 to 410 nm wavelength has been urgent need.

As a result of studies conducted by the present inventors on recording materials suitable for an optical recording medium, the following two findings were obtained.

(1) Since a large capacity optical recording medium uses a laser beam of 300 to 500 nm in writing and reading data, it is important to control the absorption coefficient, refractive index, and reflectivity of the recording medium in the vicinity of the laser wavelength.

(2) As mentioned above, although large-capacity optical recording media using the laser have been aggressively developed and particularly the development of a dye having excellent light stability and good high-speed recording characteristics has been desired, the dye compounds mentioned above have not yet satisfied recording characteristics as a recording material capable of reading and writing data with a laser beam of the wavelength range and thus still need to be improved at present. Furthermore, as a favorable characteristic of a dye for use in a medium manufactured by a coating method, such as spin coating, which is a simple method for forming a recording film, the high solubility of the dye to a coating solvent must be considered.

Also, in general, to increase the storage capacity, higher-density recording must be performed. To attain this, it is necessary to increase the numerical aperture of an object lens in order to converge an optical beam for use in recording and generate a shorter-wavelength laser by an optical system. However, when an optical beam is converged, the minimum beam diameter is determined by its diffraction-limit.

In the meantime, since writing is made when the intensity of beam exceeds a certain threshold, the record pit obtained is smaller than the beam spot converged, as shown in FIG. 1(a). The periphery of the record pit corresponds to the skirts of the intensity peak. Under the present circumstances where a further shorter wavelength laser is developed, a photochemical reaction in the recording layer is facilitated even in the periphery of the record pit. In particular, in the wavelength range of the aforementioned bluish-violet laser, a photochemical reaction of an organic compound is likely to occur, producing a problem: a pit edge is degraded during writing time, decreasing signal characteristics. To explain more specifically, recoding data which must be essentially written in response to a rectangular wave [indicated by a solid line in FIG. 1(b)], as shown in FIG. 1(b), results in a broader tailed wave form (indicated by a broken line in FIG. 1(b) due to the deterioration of the pit edge. Furthermore, when regeneration is performed by the same bluish-violet laser wavelength as in recording, a photo reaction is facilitated even by weak light irradiation such as regeneration light. As a result, deterioration proceeds every time regeneration is performed. Against such a problem, Japanese Patent Laid-Open Nos. 7-304256 and 7-304257 take measures by varying the wavelength of recording light from that of regeneration light, virtually, using a longer wavelength light as regeneration light than recording light. As a result, the requirement for high-density recording has not yet sufficiently satisfied up to present. Furthermore, using recording light and regeneration light different in wavelength means that a recording device and a regeneration device must be separately prepared or means that two optical systems and control systems must be provided in a single apparatus, with the result that such an optical recording medium is limited in use and entails enlargement of the apparatus, increase of cost, and losing general versatility. Furthermore, in a conventional optical recording medium such as CD-R, on/off of writing can be determined based on whether or not reaching thermal threshold on physical characteristics such as melting point, sublimation, point, phase transition point or thermo-decomposition point of an organic dye film. However, such a contrast is made indistinctive by optical deterioration due to excitation of a bluish-violet laser. In particular, in a high-density recording system in which recording pits must be formed smaller than that of an optical beam, there is a possibility that the quality of a recording signal may significantly decrease.

Now, as a case where an organic dye film is used in recording in the visible light range of 400 to 700 nm, Published Japanese translations of PCT international publication No. 2002-501497 describes a writable and erasable optical recording medium using a perylene-based compound. Further, Japanese Patent Laid-Open No. 10-6645 describes a laser beam of 620 to 690 nm wavelength used on a medium using a perylene compound analogue in the recording layer. However, it was found that these compounds are still insufficient with respect to light stability and signal characteristics when a bluish-violet laser of 400 to 410 nm wavelength is used for writing.

Also, as an optical recording medium using an organic dye, on which recording can be made by a laser of 400 to 500 nm wavelength, Japanese Patent Laid-Open No. 2000-113504 describes an optical recording medium using a naphthalene imide compound. However, it was found that the compound was still unsatisfactory in light stability and the recording medium thus required further improvement.

DISCLOSURE OF THE INVENTION

An object of the present invention is to provide an optical recording medium which has a recording layer suitable for very high density recording and to which writing and reading can be satisfactorily performed by a laser beam in the wavelength range of 300 to 900 nm and particularly a bluish-violet laser beam selected from the wavelength range of 400 to 410 nm, and also to provide a novel compound preferably used in the optical recording medium.

The present inventors have conducted intensive studies with a view to solving the aforementioned problems, with the result that they have accomplished the present invention. More specifically, the present invention provides:

(1) An optical recording medium containing one or more compounds selected from imide compounds having a metallocene residue in a recording layer;

(2) An optical recording medium in which one or more compounds are selected from imide compounds in which a nitrogen atom of at least one imide group is substituted by a substituent having a metallocene residue and contained in a recording layer;

(3) An optical recording medium in which an imide compound is represented by a general formula (1)

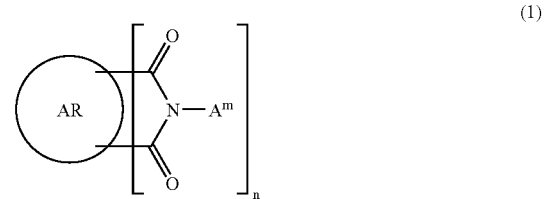

wherein a ring AR represents a substituted or unsubstituted aromatic ring residue or a residue formed by combining two or more aromatic ring residues via one or more linking groups; n represents the number of imide groups bonded to the ring AR; $A^m$ represents any one of substituents $A^1$ to $A^n$ bonded to a nitrogen atom of each imide group; and m represents an integer of from 1 to n, with the proviso that at least one substituent selected from the group consisting of $A^1$ to $A^n$ is one having at least one substituted or unsubstituted metallocene residue;

(4) An optical recording medium in which the at least one substituent selected from the group consisting of $A^1$ to $A^n$ is a substituted or unsubstituted aromatic ring group having a substituted or unsubstituted metallocene residue;

(5) An optical recording medium according to the aforementioned (4) in which the substituted or unsubstituted aromatic ring group is a substituted or unsubstituted phenyl group;

(6) An optical recording medium in which an imide compound is represented by a general formula (2):

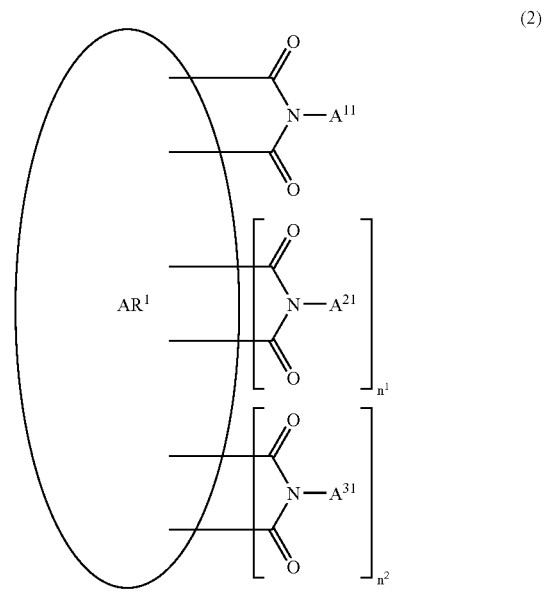

wherein a ring $AR^1$ represents an aromatic ring residue or a residue formed by combining two or more aromatic ring residues via one or more one linking groups; $n^1$ and $n^2$ each independently represent 0 or 1; $A^{11}$, $A^{21}$ and $A^{31}$ each represent a substituent bonded to a nitrogen atom of each imide group; and at least one substituent selected from the group consisting of $A^{11}$, $A^{21}$ and $A^{31}$ is one having one or more substituted or unsubstituted metallocene residue;

(7) An optical recording medium in which the at least one substituent selected from the group consisting of $A^{11}$ to $A^{31}$ is a substituted or unsubstituted aromatic ring group having a substituted or unsubstituted metallocene residue, (8) An optical recording medium in which a substituted or unsubstituted aromatic ring group is a substituted or unsubstituted phenyl group;

(9) An optical recording medium in which an imide compound is represented by a general formula (3);

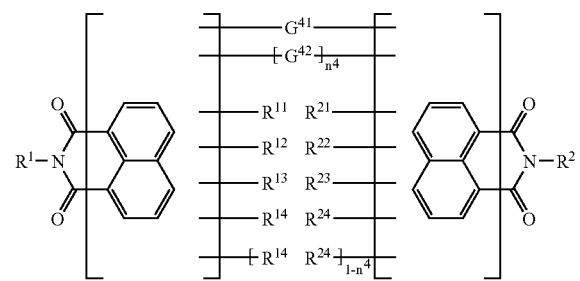

(3)

wherein $R^1$, $R^2$, $R^{11}$ to $R^{15}$, and $R^{21}$ to $R^{25}$ each independently represent a hydrogen or halogen atom; a group selected from nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, heteroarylthio, or substituted or unsubstituted metallocenyl; or, in a combination of $R^{11}$ to $R^{15}$ and/or a combination of $R^{21}$ to $R^{25}$, two or more substituents selected from each of the combinations may independently combine via a linking group within the same combination to form a cyclic structure together with carbon atoms to which they are attached; $G^{41}$ and $G^{42}$ each represent a bivalent linking group composed of at least one selected from a single bond, substituted or unsubstituted bivalent aliphatic hydrocarbon, or substituted or unsubstituted bivalent aromatic ring; $n^4$ represents 0 or 1; with the proviso that at least one of $R^1$ and $R^2$ represents a group in which a substituted or unsubstituted metallocene residue bonds to the nitrogen atom of the imide group via a bivalent linking group composed of at least one selected from substituted or unsubstituted bivalent aliphatic hydrocarbon, or substituted or unsubstituted bivalent aromatic ring;

(10) The optical recording medium according to any one of (1) to (8) in which an imide compound is represented by a general formula (4)

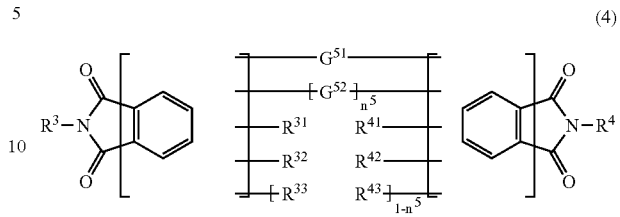

(4)

wherein $R^3$, $R^4$, $R^{31}$ to $R^{33}$, and $R^{41}$ to $R^{43}$ each independently represent a hydrogen or halogen atom; a group selected from nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, heteroarylthio, or substituted or unsubstituted metallocenyl; or, in a combination of $R^{31}$ to $R^{33}$ and/or a combination of $R^{41}$ to $R^{43}$, two or more substituents selected from each of the combinations may independently combine via a linking group within the same combination to form a cyclic structure together with carbon atoms to which they are attached; $G^{51}$ and $G^{52}$ represent a bivalent linking group composed of at least one selected from a single bond, substituted or unsubstituted bivalent aliphatic hydrocarbon, or substituted or unsubstituted bivalent aromatic ring; $n^5$ represents 0 or 1; with the proviso that at least one of $R^3$ and $R^4$ represents a group in which a substituted or unsubstituted metallocene residue bonds to the nitrogen atom of the imide group via a bivalent linking group composed of at least one selected from a substituted or unsubstituted bivalent aliphatic hydrocarbon, or substituted or unsubstituted bivalent aromatic ring;

(11) An optical recording medium in which an imide compound is represented by a general formula (5)

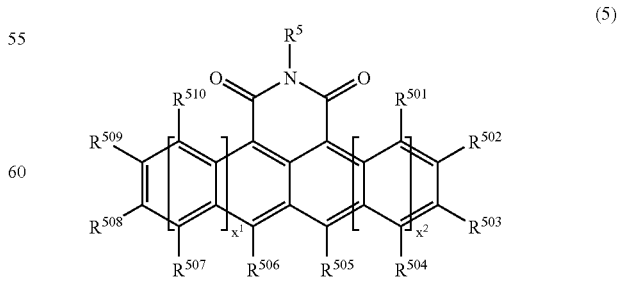

(5)

wherein $R^{501}$ to $R^{510}$ each independently represent a hydrogen or halogen atom; a group selected from nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, substituted or unsubstituted heteroarylthio, or substituted or unsubstituted metallocenyl; or, in a combination of $R^{501}$ to $R^{510}$, two or more substituents selected from the combination may independently combine via a linking group to form a cyclic structure together with carbon atoms to which they are attached; $R^5$ represents a group in which a substituted or unsubstituted metallocene residue bonds to the nitrogen atom of the imide group via a bivalent linking group composed of at least one selected from a substituted or unsubstituted bivalent aliphatic hydrocarbon, or substituted or unsubstituted bivalent aromatic ring; and $X^1$ and $X^2$ represent an integer of 0 to 2;

(12) An optical recording medium in which an imide compound is represented by a general formula (6)

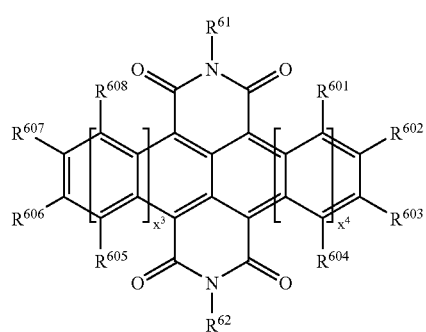

(6)

wherein $R^{601}$ to $R^{608}$ each independently represent a hydrogen or halogen atom; a group selected from nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, substituted or unsubstituted heteroarylthio, or substituted or unsubstituted metallocenyl; or, in a combination of $R^{601}$ to $R^{604}$ and/or a combination of $R^{605}$ to $R^{608}$, two or more substituents selected from each of the combinations may independently combine via a linking group within the same combination to form a cyclic structure together with carbon atoms to which they are attached; $R^{61}$ and $R^{62}$ represent a group in which a substituted or unsubstituted metallocene residue bonds to the nitrogen atom of the imide group via a bivalent linking group composed of at least one selected from a substituted or unsubstituted bivalent aliphatic hydrocarbon, or substituted or unsubstituted bivalent aromatic ring; and $X^3$ and $X^4$ represent an integer of 0 to 2;

(13) An optical recording medium in which an imide compound is a naphthalene diimide compound represented by a general formula (7):

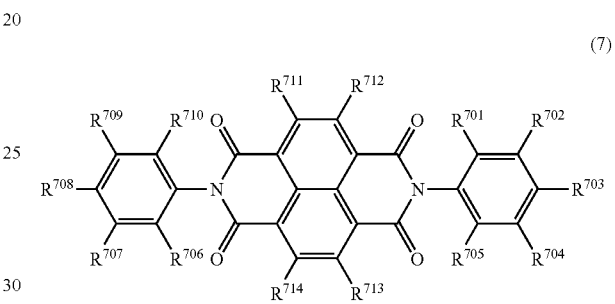

(7)

wherein $R^{701}$ to $R^{714}$ each independently represent a hydrogen or halogen atom; a group selected from nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, substituted or unsubstituted heteroarylthio, or substituted or unsubstituted metallocenyl; or, in a combination of $R^{701}$ to $R^{705}$ and/or a combination of $R^{706}$ to $R^{710}$, and/or combination of $R^{711}$ to $R^{715}$, two or more substituents selected from each of the combinations may independently combine via a linking group within the same combination to form a cyclic structure together with carbon atoms to which they are attached, with the proviso that any one or more groups selected from $R^{701}$ to $R^{710}$ represent substituted or unsubstituted metallocenyl group.

(14) An optical recording medium of the aforementioned compound (7) in which any one or more groups of $R^{711}$ to $R^{714}$ are halogen atoms;

(15) An optical recording medium in which an imide compound has a quinazoline residue;

(16) An optical recording medium in which an imide compound is represented by a general formula (8) as one of tautomeric structures:

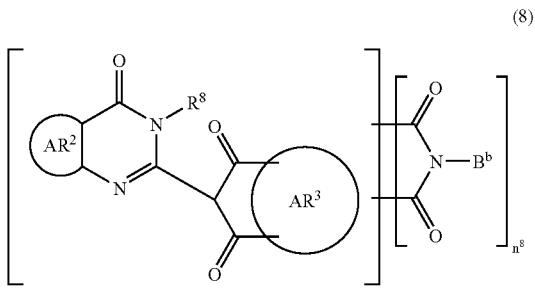

wherein a ring $AR^2$ and ring $AR^3$ represent a substituted or unsubstituted aromatic ring residue or a residue formed by combining two or more aromatic ring residues via one or more linking groups; $R^8$ represents a hydrogen atom or a substituent; $n^8$ represents the number of imide groups bonded to the ring $AR^2$ and/or ring $AR^3$; $B^b$ represents a substituent of $B^1$ to $B''^8$ bonded to a nitrogen atom of each imide group; and b represents an integer of from 1 to $n^8$, with the proviso that at least one substituent selected from $B^1$ to $B''^8$ is one having one or more substituted or unsubstituted metallocene residues.

(17) An optical recording medium in which an imide compound has a quinazoline-4-on residue represented by a general formula (9) as one of tautomeric structures:

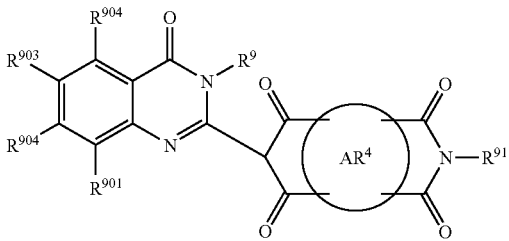

wherein a ring $AR^4$ represents a substituted or unsubstituted aromatic ring residue or a residue formed by combining two or more aromatic ring residues via one or more linking groups; $R^9$ represents hydrogen, substituted or unsubstituted alkyl, substituted or unsubstituted aralkyl, or substituted or unsubstituted aromatic ring; $R^{901}$ to $R^{904}$ each independently represent a hydrogen or halogen atom; a group selected from nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or. unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, heteroarylthio, or substituted or unsubstituted metallocenyl; or, in a combination of $R^{901}$ to $R^{904}$, two or more substituents selected from the combination may independently combine via a linking group to form a cyclic structure together with carbon atoms to which they are attached; and $R^{91}$ represents a group in which a substituted or unsubstituted metallocene residue bonds to the nitrogen atom of the imide group via a bivalent linking group composed of at least one group selected from a substituted or unsubstituted bivalent aliphatic hydrocarbon, or substituted or unsubstituted bivalent aromatic ring;

(18) An optical recording medium in which an imide compound has a quinazoline-4-on residue represented by a general formula (10) as one of tautomeric structures:

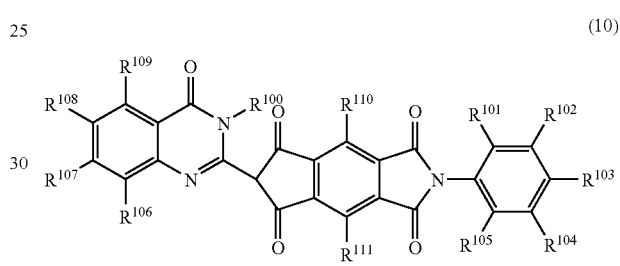

wherein $R^{100}$ represents hydrogen or substituted or unsubstituted alkyl, substituted or unsubstituted aralkyl or substituted or unsubstituted aromatic ring; $R^{101}$ to $R^{111}$ each independently represent a hydrogen or halogen atom; a group selected from nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, heteroarylthio, or substituted or unsubstituted metallocenyl; or, in a combination of $R^{101}$ to $R^{105}$, and/or a combination of $R^{106}$ to $R^{109}$, two or more substituents selected from each of the combinations may independently combine via a linking group in the same combination to form a cyclic structure together with carbon atoms to which they are attached, with the proviso that any one or more groups selected from $R^{101}$ to $R^{105}$ represent substituted or unsubstituted metallocenyl groups;

(19) An optical recording medium in which an imide compound has a quinazoline-4-on residue represented by a general formula (11) as one of tautomeric structures:

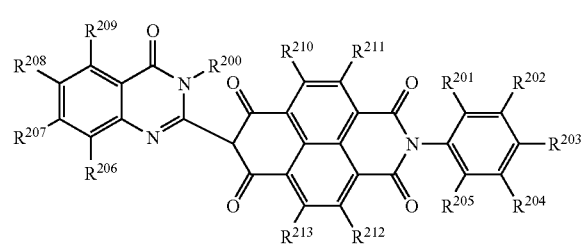

(11)

wherein $R^{200}$ represents hydrogen or substituted or unsubstituted alkyl, substituted or unsubstituted aralkyl, or substituted or unsubstituted aromatic ring; $R^{201}$ to $R^{213}$ each independently represent a hydrogen or halogen atom; a group selected from nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, heteroarylthio, or substituted or unsubstituted metallocenyl; or, in a combination of $R^{201}$ to $R^{205}$, and/or a combination of $R^{206}$ to $R^{209}$, and/or a combination of $R^{210}$ to $R^{211}$, and/or a combination of $R^{212}$ to $R^{213}$, two or more substituents selected from each of the combinations may independently combine via a linking group in the same combination to form a cyclic structure together with carbon atoms to which they are attached, with the proviso that any one or more groups selected from $R^{201}$ to $R^{205}$ represent substituted or unsubstituted metallocenyl group;

(20) An optical recording medium capable of writing and reading by a laser beam selected from the wavelength range of 300 to 900 nm;

(21) An optical recording medium capable of writing and reading by a laser beam selected from the wavelength range of 390 to 430 nm;

(22) An optical recording medium capable of writing and reading by a laser beam selected from the wavelength range of 400 to 410 nm;

(23) An imide compound represented by a general formula (1):

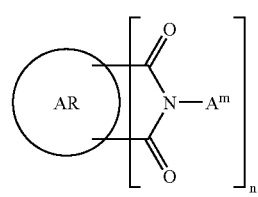

(1)

wherein a ring AR represents a substituted or unsubstituted aromatic ring residue or a residue formed by combining two or more aromatic ring residues via one or more linking groups; n represents the number of imide groups bonded to the ring AR; $A^m$ represents any one of substituents $A^1$ to $A^n$ bonded to a nitrogen atom of each imide group; and m represents an integer of from 1 to n, with the proviso that at least one substituent selected from the group consisting of $A^1$ to $A^n$ is one having at least one substituted or unsubstituted metallocene residue;

(24) A compound of the formula (1) in which the at least one substituent selected from substituents $A^1$ to $A^n$ is a substituted or unsubstituted aromatic ring group having a substituted or unsubstituted metallocene residue;

(25) A compound of the formula (1) in which the substituted or unsubstituted aromatic ring group is a substituted or unsubstituted phenyl;

(26) An imide compound represented by a formula (2):

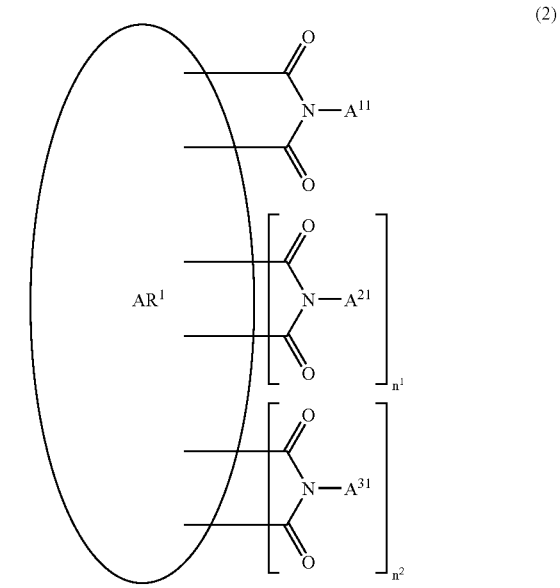

(2)

wherein a ring $AR^1$ represents an aromatic ring residue or a residue formed by combining two or more aromatic ring residues via one or more one linking groups; $n^1$ and $n^2$ each independently represent 0 or 1; $A^{11}$, $A^{21}$ and $A^{31}$ each represent a substituent bonded to a nitrogen atom of each imide group; and at least one substituent selected from the group consisting of $A^{11}$, $A^{21}$ and $A^{31}$ is one having one or more substituted or unsubstituted metallocene residue;

(27) A compound of the formula (2) in which the at least one substituent selected from substituents $A^{11}$, $A^{21}$ and $A^{31}$ is a substituted or unsubstituted aromatic ring group having a substituted or unsubstituted metallocene residue;

(28) A compound of the formula (2) in which the substituted or unsubstituted aromatic ring group is a substituted or unsubstituted phenyl;

(29) An imide compound represented by a formula (3):

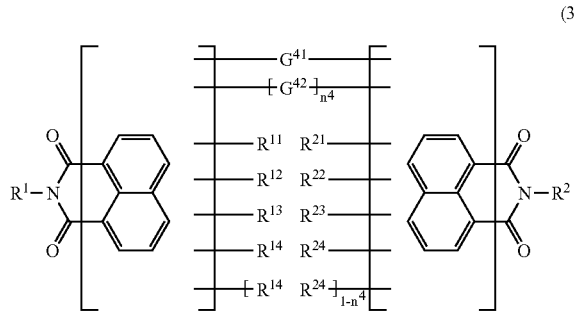

(3)

wherein $R^1$, $R^2$, $R^{11}$ to $R^{15}$, and $R^{21}$ to $R^{25}$ each independently represent a hydrogen or halogen atom; a group selected from nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, heteroarylthio, or substituted or unsubstituted metallocenyl; or, in a combination of $R^{11}$ to $R^{15}$ and/or a combination of $R^{21}$ to $R^{25}$, two or more substituents selected from each of the combinations may independently combine via a linking group within the same combination to form a cyclic structure together with carbon atoms to which they are attached; $G^{41}$ and $G^{42}$ each represent a bivalent linking group composed of at least one selected from a single bond, substituted or unsubstituted bivalent aliphatic hydrocarbon, or substituted or unsubstituted bivalent aromatic ring; $n^4$ represents 0 or 1; with the proviso that at least one of $R^1$ and $R^2$ represents a group in which a substituted or unsubstituted metallocene residue bonds to the nitrogen atom of the imide group via a bivalent linking group composed of at least one selected from substituted or unsubstituted bivalent aliphatic hydrocarbon, or substituted or unsubstituted bivalent aromatic ring;

(30) An imide compound represented by a general formula (4)

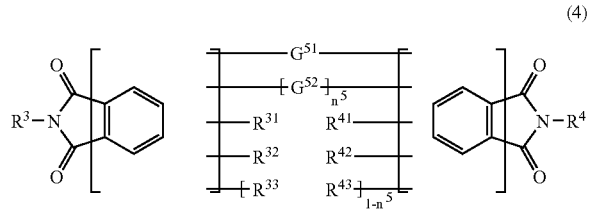

(4)

wherein $R^3$, $R^4$, $R^{31}$ to $R^{33}$, and $R^{41}$ to $R^{43}$ each independently represent a hydrogen or halogen atom; a group selected from nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, heteroarylthio, or substituted or unsubstituted metallocenyl; or, in a combination of $R^{31}$ to $R^{33}$ and/or a combination of $R^{41}$ to $R^{43}$, two or more substituents selected from each of the combinations may independently combine via a linking group within the same combination to form a cyclic structure together with carbon atoms to which they are attached; $G^{51}$ and $G^{52}$ represent a bivalent linking group composed of at least one selected from a single bond, substituted or unsubstituted bivalent aliphatic hydrocarbon, or substituted or unsubstituted bivalent aromatic ring; $n^5$ represents 0 or 1; with the proviso that at least one of $R^3$ and $R^4$ represents a group in which a substituted or unsubstituted metallocene residue bonds to the nitrogen atom of the imide group via a bivalent linking group composed of at least one selected from a substituted or unsubstituted bivalent aliphatic hydrocarbon, or substituted or unsubstituted bivalent aromatic ring;

(31) An imide compound represented by a formula (5)

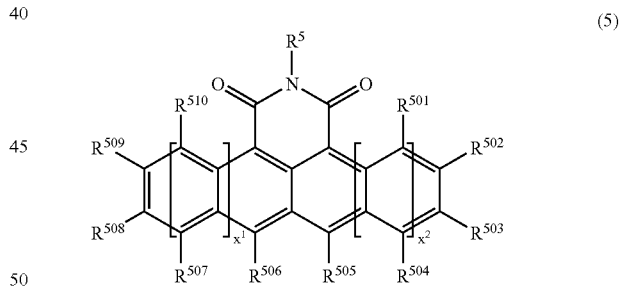

(5)

wherein $R^{501}$ to $R^{510}$ each independently represent a hydrogen or halogen atom; a group selected from nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, substituted or unsubstituted heteroarylthio, or substituted or unsubstituted metallocenyl; or, in a combination of $R^{501}$ to $R^{510}$, two or more substituents selected from the combination may independently combine via a linking group to form a cyclic structure together with carbon atoms to which they are attached; $R^5$ represents a group in which a substituted or unsubstituted metallocene residue bonds to the nitrogen atom of the imide group via a bivalent linking group composed of at least one selected from a substituted or unsubstituted bivalent aliphatic hydrocarbon, or substituted or unsubstituted bivalent aromatic ring; and $X^1$ and $X^2$ represent an integer of 0 to 2;

(32) An imide compound represented by a formula (6)

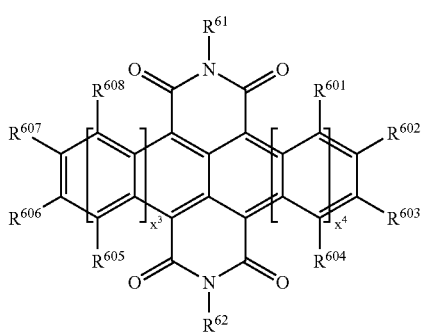

(6)

wherein $R^{601}$ to $R^{608}$ each independently represent a hydrogen or halogen atom; a group selected from nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, substituted or unsubstituted heteroarylthio, or substituted or unsubstituted metallocenyl; or, in a combination of $R^{601}$ to $R^{604}$ and/or a combination of $R^{605}$ to $R^{608}$, two or more substituents selected from each of the combinations may independently combine via a linking group within the same combination to form a cyclic structure together with carbon atoms to which they are attached; $R^{61}$ and $R^{62}$ represent a group in which a substituted or unsubstituted metallocene residue bonds to the nitrogen atom of the imide group via a bivalent linking group composed of at least one selected from a substituted or unsubstituted bivalent aliphatic hydrocarbon, or substituted or unsubstituted bivalent aromatic ring; and $X^3$ and $X^4$ represent an integer of 0 to 2;

(33) An imide compound represented by a formula (7)

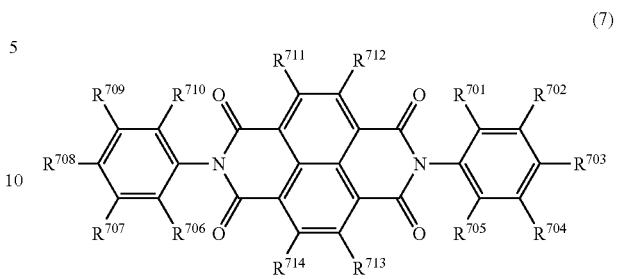

(7)

wherein $R^{701}$ to $R^{714}$ each independently represent a hydrogen or halogen atom; a group selected from nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, substituted or unsubstituted heteroarylthio, or substituted or unsubstituted metallocenyl; or, in a combination of $R^{701}$ to $R^{705}$ and/or a combination of $R^{706}$ to $R^{710}$, and/or combination of $R^{711}$ to $R^{715}$, two or more substituents selected from each of the combinations may independently combine via a linking group within the same combination to form a cyclic structure together with carbon atoms to which they are attached, with the proviso that any one or more groups selected from $R^{701}$ to $R^{710}$ represent substituted or unsubstituted metallocenyl group.

(34) A compound of the formula (7) in which any one or more groups of $R^{711}$ to $R^{714}$ is a halogen atom.

(35) An imide compound having a quinazoline residue.

(36) A compound represented by a general formula (8):

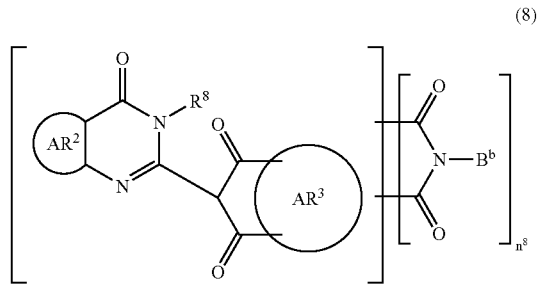

(8)

wherein a ring $AR^2$ and ring $AR^3$ represent a substituted or unsubstituted aromatic ring residue or a residue formed by combining two or more aromatic ring residues via one or more linking groups; $R^8$ represents a hydrogen atom or a substituent; $n^8$ represents the number of imide groups bonded to the ring $AR^2$ and/or ring $AR^3$; $B^b$ represents a substituent of $B^1$ to $B''^8$ bonded to a nitrogen atom of each imide group; and b represents an integer of from 1 to $n^{8,}$ with the proviso that at least one substituent selected from $B^1$ to $B''^8$ is one having one or more substituted or unsubstituted metallocene residues.

(37) A compound having a quinazoline-4-on residue represented by a general formula (9) as one of tautomeric structures:

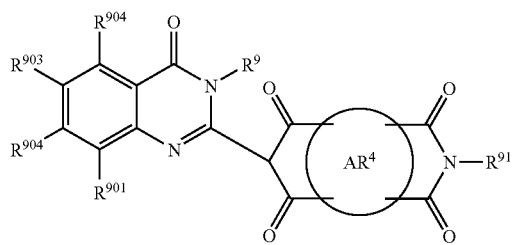

(9)

wherein a ring $AR^4$ represents a substituted or unsubstituted aromatic ring residue or a residue formed by combining two or more aromatic ring residues via one or more linking groups; $R^9$ represents hydrogen, substituted or unsubstituted alkyl, substituted or unsubstituted aralkyl, or substituted or unsubstituted aromatic ring; $R^{901}$ to $R^{904}$ each independently represent a hydrogen or halogen atom; a group selected from nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, heteroarylthio, or substituted or unsubstituted metallocenyl; or, in a combination of $R^{901}$ to $R^{904}$, two or more substituents selected from the combination may independently combine via a linking group to form a cyclic structure together with carbon atoms to which they are attached; and $R^{91}$ represents a group in which a substituted or unsubstituted metallocene residue bonds to the nitrogen atom of the imide group via a bivalent linking group composed of at least one group selected from a substituted or unsubstituted bivalent aliphatic hydrocarbon, or substituted or unsubstituted bivalent aromatic ring;

(38) A compound having a quinazoline-4-on residue represented by a general formula (10) as one of tautomeric structures:

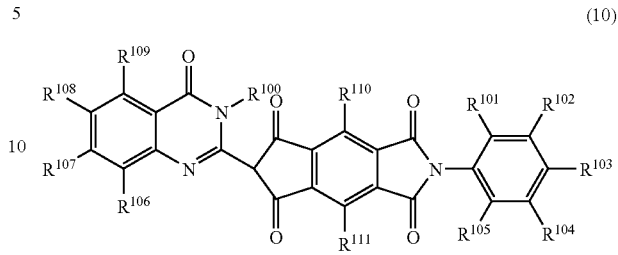

(10)

wherein $R^{100}$ represents hydrogen or substituted or unsubstituted alkyl, substituted or unsubstituted aralkyl or substituted or unsubstituted aromatic ring; $R^{101}$ to $R^{111}$ each independently represent a hydrogen or halogen atom; a group selected from nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, heteroarylthio, or substituted or unsubstituted metallocenyl; or, in a combination of $R^{101}$ to $R^{105}$, and/or a combination of $R^{106}$ to $R^{109}$, two or more substituents selected from each of the combinations may independently combine via a linking group in the same combination to form a cyclic structure together with carbon atoms to which they are attached, with the proviso that any one or more groups selected from $R^{101}$ to $R^{105}$ represent substituted or unsubstituted metallocenyl groups; and

(39) A compound having a quinazoline-4-on residue represented by a general formula (11) as one of tautomeric structures:

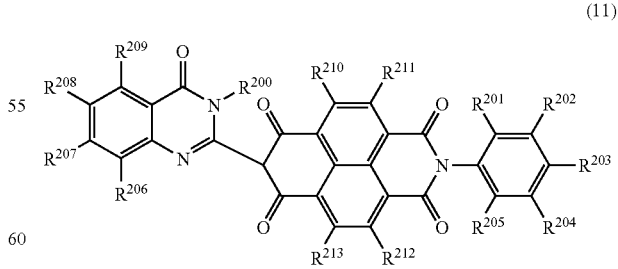

(11)

wherein $R^{200}$ represents hydrogen or substituted or unsubstituted alkyl, substituted or unsubstituted aralkyl, or substituted or unsubstituted aromatic ring; $R^{201}$ to $R^{213}$ each independently represent a hydrogen or halogen atom; a group selected from nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, heteroarylthio, or substituted or unsubstituted metallocenyl; or, in a combination of $R^{201}$ to $R^{205}$, and/or a combination of $R^{206}$ to $R^{209}$ and/or a combination of $R^{210}$ to $R^{211}$, and/or a combination of $R^{212}$ to $R^{213}$, two or more substituents selected from each of the combinations may independently combine via a linking group in the same combination to form a cyclic structure together with carbon atoms to which they are attached, with the proviso that any one or more groups selected from $R^{201}$ to $R^{205}$ represent substituted or unsubstituted metallocenyl group.

BEST MODE FOR CARRYING OUT THE INVENTION

The present invention relates to an optical recording medium characterized by containing an imide compound of the present invention in a recording layer thereof, and a novel optical recording medium capable of writing and reading by a laser beam selected from the wavelength range of 300 to 900 nm, particularly from 390 to 430 nm, and more particularly from 400 to 410 nm and a novel imide compound.

The optical recording medium according to the present invention is one capable of writing and reading data. However, herein, as an appropriate example, an optical recording medium of the present invention having a recording layer and a reflecting layer on a substrate will be explained. Note that, in the following explanation, as an optical recording medium, an optical disk, which has a supporting substrate having guide grooves and a reflecting film and a recording layer containing an organic dye as a main component formed on the guide grooves, to which a laser beam of a wavelength of 300 to 500 nm is applied to perform read and write of a signal, will be described. However, the optical recording medium of the present invention is not limited to such a structure and constitution, and may be applied to the media of a card-form, sheet-form and other forms, and having no reflecting layer, and applied to writing and reading performed by a shorter wavelength laser which will be developed in future.

Figure 1:
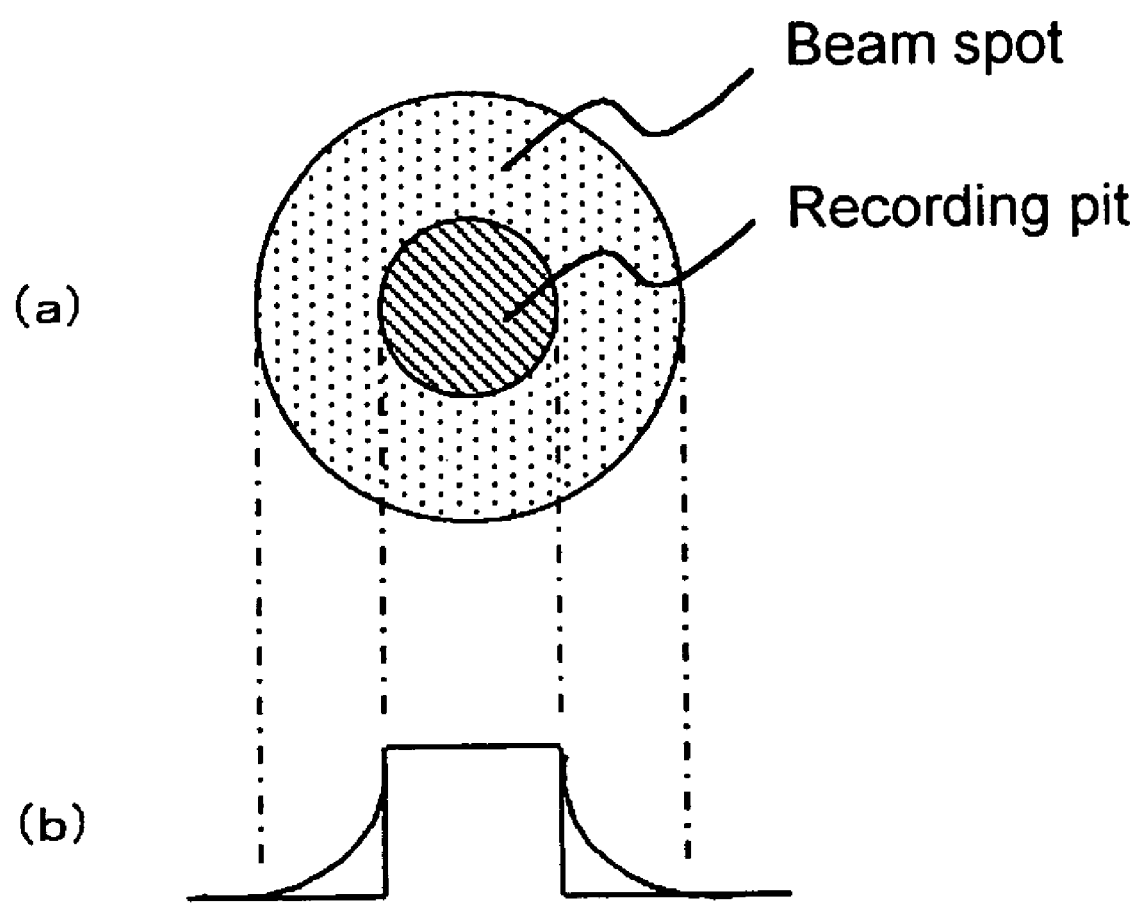
FIG. 1 is a conceptual diagram illustrating an object of the present invention.
Figure 2:
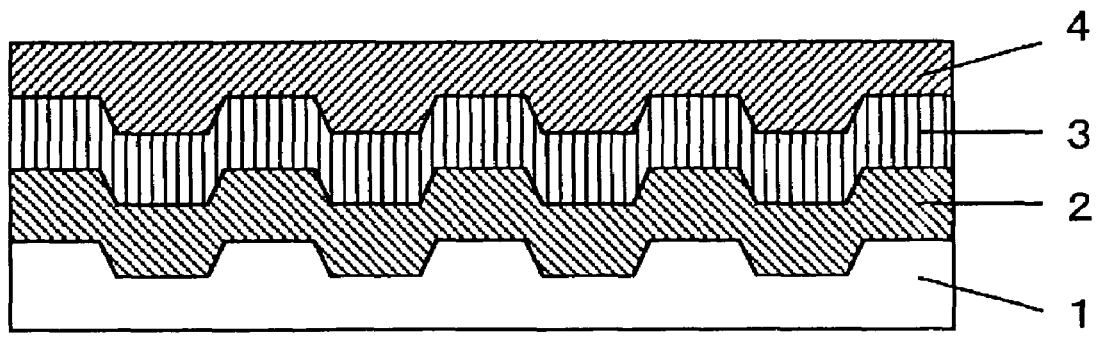
FIG. 2 is a schematic view showing a structure of an optical recording medium of the present invention.
Figure 3:
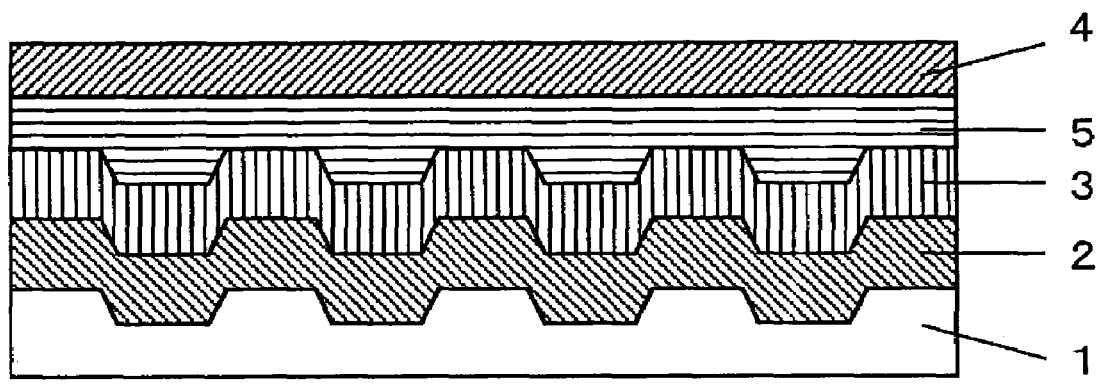
FIG. 3 is a schematic view showing another structure of an optical recording medium of the present invention.
Figure 4:
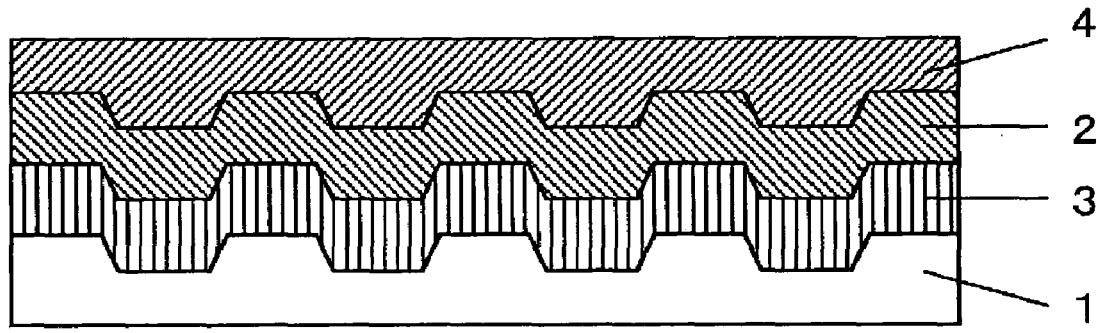
FIG. 4 is a schematic view showing still another structure of an optical recording medium of the present invention.

An optical recording medium of the present invention has, for example, either a four layered structure in which a substrate 1, a recording layer 2, a reflecting layer 3 and a protecting layer 4 are sequentially stacked as shown in FIG. 2 or a bonded structure as shown in FIG. 3. More specifically, the recording layer 2 is formed on the substrate 1 and the reflecting layer 3 is formed on and in close contact with the recording layer 2. Further on the resultant structure, the protecting layer 4 is bonded with an adhesion layer 5 interposed between them. Note that another layer may be present under or on the recording layer 2 and another layer may be present on the reflecting layer 3. Alternatively, as shown in FIG. 4, the substrate 1, reflecting layer 3, recording layer 2, and protecting layer 4 are sequentially stacked and read and write may be performed from the side of the protecting layer. As described in Japanese Patent Laid-Open No. 10-326435, a medium may have a structure in which the thickness of a light transmission layer is defined based on the numerical aperture (N.A.) of the optical system and the wavelength λ of a laser. Furthermore, an optical recording medium of the present invention may have a structure having two or more recording layers if necessary as described in Japanese Patent Laid-Open No. 11-203729.

Figure 5:
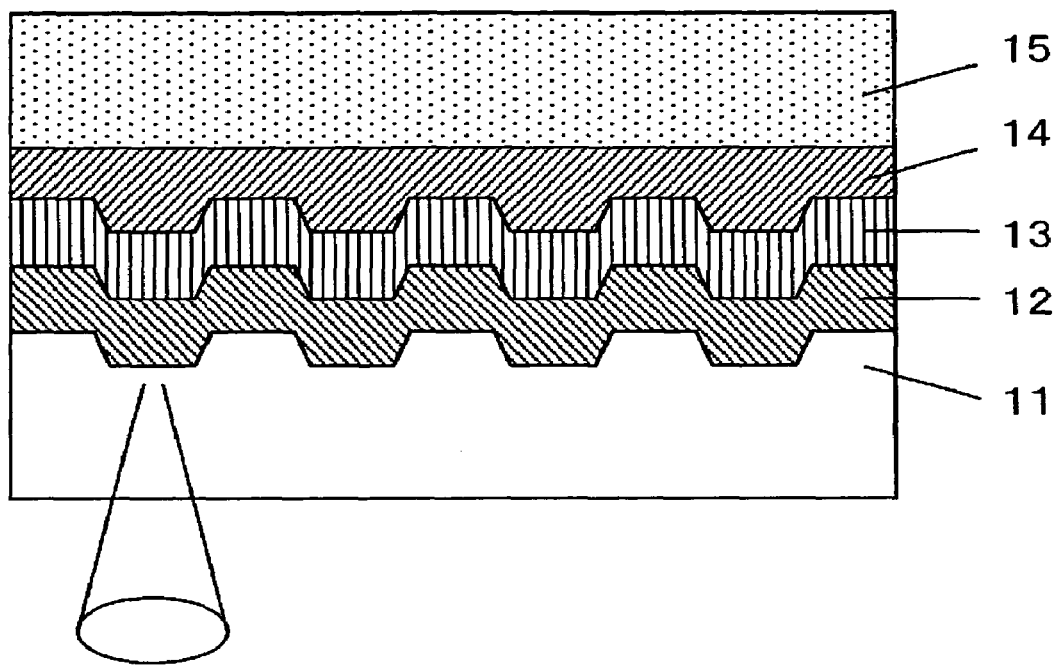
FIG. 5 is a schematic view showing a further structure of an optical recording medium of the present invention.

As an example where the present invention is applied to an optical disk, a structure as shown in FIG. 5 may be mentioned in which a substrate 11, a recoding layer 12, a reflecting layer 13 and a protecting layer 14 are stacked in this order and further a dummy substrate 15 is bonded on the protecting layer 14 also serving as an adhesion layer. Of course, a structure having no substrate 15 may be used and other layers may be present between the substrate 11 and the recording layer 12, between the recording layer 12 and the reflecting layer 13, between the reflecting layer 13 and the protecting layer 14, and between the protecting layer 14 and the dummy substrate 15. In the optical disk of FIG. 5, write and read may be performed from the side of the substrate 11.

Figure 6:
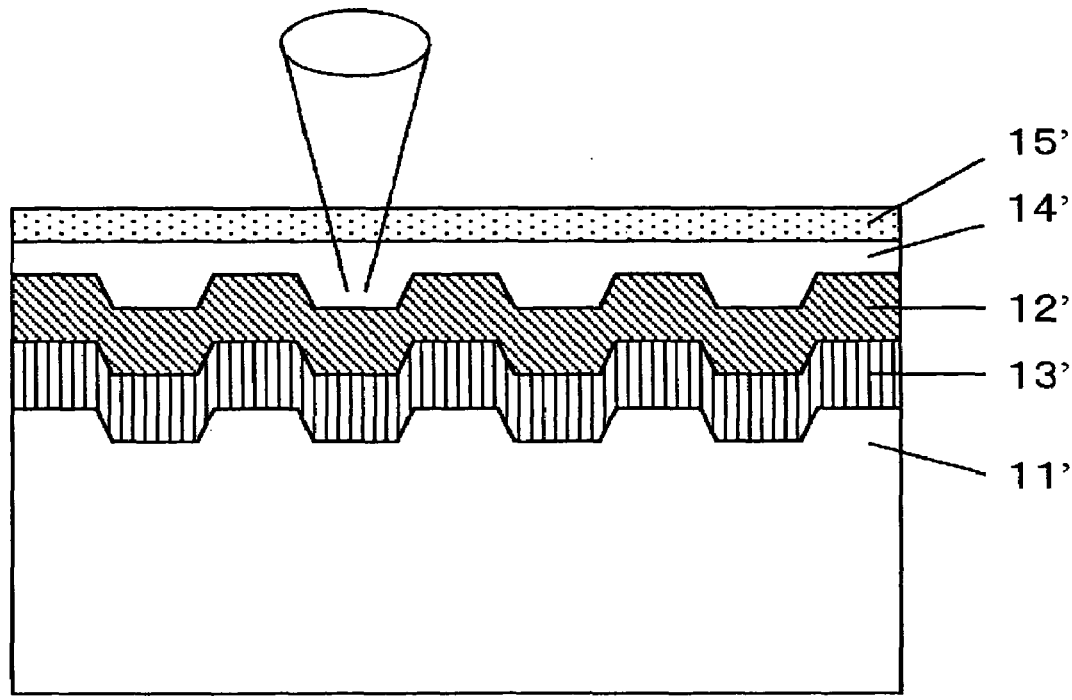
FIG. 6 is a schematic view showing still a further structure of an optical recording medium of the present invention.

Furthermore, as another embodiment, the constitution disclosed in Japanese Patent Laid-Open No. 10-302310 may be used. For example, as shown in FIG. 6, on the supporting substrate 11' having guide grooves therein, a reflecting layer 13' and a recording layer 12' containing an organic dye as a main component are stacked in this order. On the recording layer 12', a light transmission layer 15' is formed via a transparent protecting layer 14', which is optionally formed on the recording layer 12'. Write and read are performed from the side of the light transmission layer 15'. Note that guide grooves may be conversely formed on the side of the light transmission layer 15' and the transparent protecting layer 14', recording layer 12' and reflecting layer 13' may be stacked on the light transmission layer 15' and adhered to the supporting substrate 11'.

Figure 7:
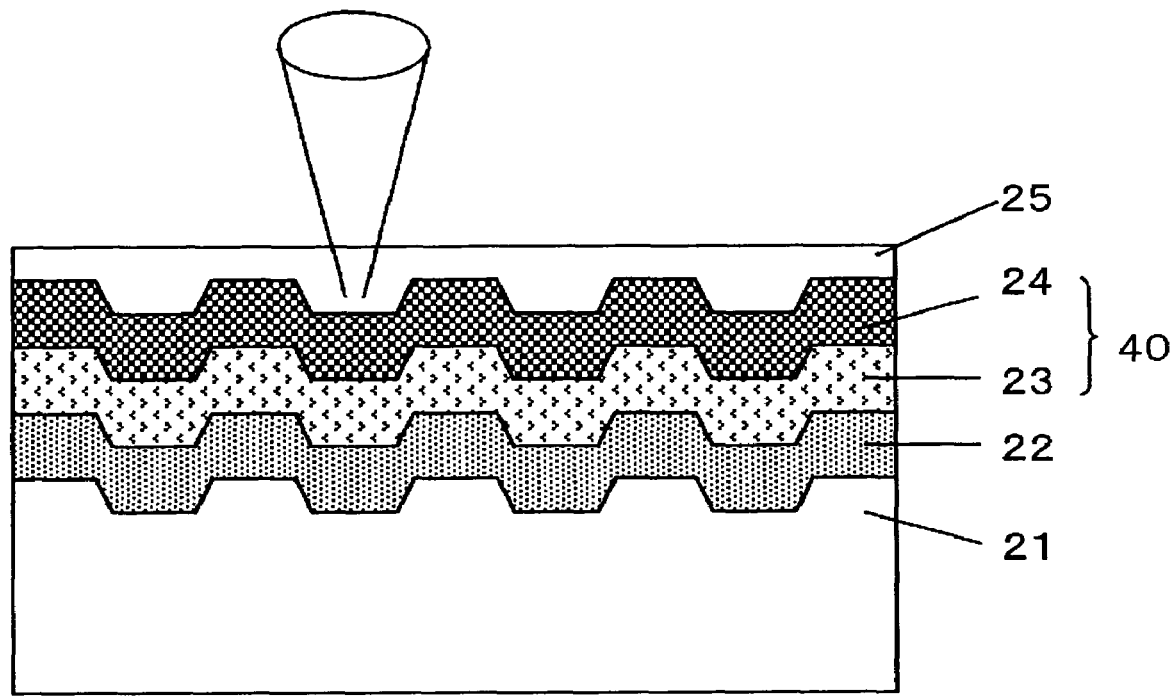
FIG. 7 is a schematic view showing even a further structure of an optical recording medium of the present invention.

Alternatively, as another embodiment, the structure disclosed in Japanese Patent Laid-Open No. 2002-175645 is known. For example, as shown in FIG. 7, on a supporting substrate 21 having guide grooves, a recording layer 22 containing an organic dye as a main component is formed in this order. On the recording layer 22, a nitride layer 23 and an oxide layer 24 are sequentially formed, thereby forming a dielectric layer 40. Further, on the dielectric layer 40, a light transmission layer 25 is formed by applying an adhesive agent between them, if necessary. The write and read of data is performed from the side of the light transmission layer 25. Note that, the structure may be conversely formed by forming guide grooves on the side of the light transmission layer 25, stacking a dielectric layer 40, which is formed by sequentially stacking the oxide layer 24 and the nitride layer 23, and the recording layer 22 and adhering to the supporting substrate 21. As described above, an optical recording medium providing an appropriate initial reflectivity can be obtained by obtaining an optical enhancement effect due to multiple interference given by forming a dielectric layer on a data recording layer without using a reflecting layer. A compound of the present invention can be applied to such a medium.

In the present invention, a recording layer is provided on a substrate. The recording layer of the present invention contains at least one type of imide-based compound according to the present invention, in particular, a compound represented by a general formula (1), as a recording dye. The recording dye is the one whose thermal decomposition and sublimation can be induced by laser beam irradiation, to cause a change of a recording layer or in the texture (formation of pits), thereby forming a portion varied in reflectivity. An optical recording medium of the present invention is capable of writing and reading data with the wavelength of a recording laser particularly selected from the wavelength range of 300 to 900 nm. More particularly, when a writing laser wavelength and reading laser wavelength selected from the range of 390 to 430 nm, and more particularly, from 400 to 410 nm is applied to the optical recording medium, good signal characteristics can be obtained.

An imide compound according to the present invention, since it can arbitrarily select the absorbing wavelength by selecting a substituent while maintaining the absorption constant, can provide a satisfactory optical constant required for the recording layer at the aforementioned laser wavelength. Furthermore, the imide compound is extremely useful organic dye having a high stability to light and excellent stability of reading light.

The present invention will be described in more detail below.

In an optical recording medium of the present invention, one or more types of imide compounds according to the present invention are contained in the recoding layer. As an imide compound according to the present invention, an imide compound having a metallocene residue, preferably, an imide compound having at least one imide group having a metallocene residue may be mentioned. More preferably, a compound represented by the following general formula (1) may be mentioned as a preferable example.

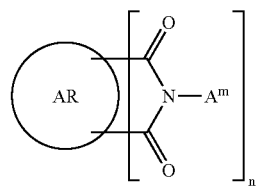

(1)

wherein a ring AR represents a substituted or unsubstituted aromatic ring residue or a residue formed by combining two or more aromatic ring residues via one or more linking groups; n represents the number of imide groups bonded to the ring AR; $A^m$ represents any one of substituents $A^1$ to $A^n$ bonded to a nitrogen atom of each imide group; and m represents an integer of from 1 to n, with the proviso that at least one substituent selected from the group consisting of $A^1$ to $A^n$ is one having at least one substituted or unsubstituted metallocene residue.

In the formula, as a ring constituting an aromatic ring residue represented by a ring AR, it is preferable to use a substituted or unsubstituted carbocyclic aromatic ring, or substituted or unsubstituted heterocyclic aromatic ring. It is more preferable to use a substituted or unsubstituted carbocyclic aromatic ring or substituted or unsubstituted heterocyclic aromatic ring having 3 to 60 carbon atoms, and further preferable to use a substituted or unsubstituted carbocyclic aromatic ring or substituted or unsubstituted heterocyclic aromatic ring having 3 to 26 carbon atoms.

Specific examples of an aromatic ring represented by a ring AR include carbocyclic aromatic rings such as benzene, naphthalene, pentalene, indacene, azuren, heptalene, biphenylene, phenanthrene, anthracene, fluoranthene, acenaphthylene, triphenylene, pyrene, chrysene, naphthacene, pleiadene, picene, perylene, pentaphene, pentacene, tetraphenylene, hexaphene, hexacene, rubicene, coronene, trinaphthylene, heptaphene, heptacene, pyranthrene, ovalene, and fullerene; and heterocyclic aromatic rings such as furan, thiophene, pyrrole, pyrazole, imidazole, oxazole, thiazole, pyridine, pyridazine, pyrimidine, pyrazine, quinoline, isoquinoline, quinoxaline, indolizine, indole, indazole, purine, phthalazine, naphthylidine, quinazoline, cinnoline, pteridine, carbazole, carboline, phenanthridine, acridine, perimidine, phenanthroline, phenazine, and furazan.

When a ring AR has a substituent, preferable examples of the substituent include a halogen atom and groups such as nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, substituted or unsubstituted heteroarylthio, and substituted or unsubstituted metallocenyl.

Examples of a halogen atom to substitute a ring AR include fluorine, chlorine, bromine, and iodine.

Specific examples of a substituted or unsubstituted alkyl group to substitute a ring AR include unsubstituted alkyl such as methyl, ethyl, n-propyl, isopropyl, n-butyl, isobutyl, sec-butyl, tert-butyl, n-pentyl, isopentyl, 2-methylbutyl, 1-methylbutyl, neopentyl, 1,2-dimethylpropyl, 1,1-dimethylpropyl, cyclopentyl, n-hexyl, 4-methylpentyl, 3-methylpentyl, 2-methylpentyl, 1-methylpentyl, 3,3-dimethylbutyl, 2,3-dimethylbutyl, 1,3-dimethylbutyl, 2,2-dimethylbutyl, 1,2-dimethylbutyl, 1,1-dimethylbutyl, 2-ethylbutyl, 1-ethylbutyl, 1,2,2-trimethylbutyl, 1,1,2-trimethylbutyl, 1-ethyl-2-methylpropyl, cyclohexyl,n-heptyl, 2-methylhexyl, 3-methylhexyl, 4-methylhexyl, 5-methylhexyl, 2,4-dimethylpentyl n-octyl, 2-ethylhexyl, 2,5-dimethylhexyl, 2,5,5-trimethylpentyl, 2,4-dimethylhexyl, 2,2,4-dimethylpentyl, 3,5,5-trimethylhexyl, n-nonyl, n-decyl, 4-ethyloctyl, 4-ethyl-4,5-methylhexyl, n-undecyl, n-dodecyl, 1,3,5,7-tetraethyloctyl, 4-butyloctyl, 6,6-diethyloctyl, n-tridecyl, 6-methyl-4-butyloctyl, n-tetradecyl, n-pentadecyl, 3,5-dimethylheptyl, 2,6-dimethylheptyl, 2,4-dimethylheptyl, 2,2,5,5,5-tetramethylhexyl, 1-cyclopentyl-2,2-dimethylpropyl, or 1-cyclohexyl-2,2-dimethylpropyl;

alkyl substituted by halogen such as chloromethyl, 1-chloroethyl, 2-chloroethyl, 2-bromoethyl, 2-iodoethyl, dichloromethyl, fluoromethyl, trifluoromethyl, pentafluoroethyl, 2,2,2-trifluoroethyl, 2,2,2-trichloroethyl, 1,1,1,3,3,3-hexafluoro-2-propyl, nonafluorobutyl, or perfluorodecyl;

alkyl substituted by hydroxyl such as hydroxymethyl, 2-hydroxyethyl, 3-hydroxypropyl, 4-hydroxybutyl, 2-hydroxy-3-methoxypropyl, 2-hydroxy-3-chloropropyl, 2-hydroxy-3-ethoxypropyl, 3-butyloxy-2-hydroxypropyl, 2-hydroxy-3-cyclohexyloxypropyl, 2-hydroxypropyl, 2-hydroxybutyl, or 4-hydroxydecalyl;

alkyl substituted by hydroxyalkoxy such as hydroxymethoxymethyl, hydroxyethoxyethyl, 2-(2'-hydroxy-1'-methylethoxy)-1-methylethyl, 2-(3'-fluoro-2'-hydroxypropyloxy)ethyl, 2-(3'-chloro-2'-hydroxypropyloxy)ethyl, or hydroxybutyloxycyclohexyl;

alkyl substituted by hydroxyalkoxyalkoxy such as hydroxymethoxymethoxymethyl, hydroxyethoxyethoxyethyl, [2'-(2'-hydroxy-1'-methylethoxy)-1'-methylethoxy]ethoxyethyl, [2'-(2'-fluoro-1'-hydroxyethoxy)-1'-methylethoxy]ethoxyethyl, [2'-(2'-chloro-1'-hydroxyethoxy)-1'-methylethoxy]ethoxyethyl;

alkyl substituted by cyano such as cyanomethyl, 2-cyanoethyl, 3-cyanopropyl, 4-cyanobutyl, 2-cyano-3-methoxypropyl, 2-cyano-3-chloropropyl, 2-cyano-3-ethoxypropyl, 3-butyloxy-2-cyanopropyl, 2-cyano-3-cyclohexylpropyl, 2-cyanopropyl, or 2-cyanobutyl;

alkyl substituted by alkoxy such as methoxymethyl, ethoxymethyl, n-propyloxymethyl, n-butyloxymethyl, methoxyethyl, ethoxyethyl, n-propyloxyethyl, n-butyloxyethyl, n-hexyloxyethyl, (4-methylpentyloxy)ethyl, (1,3-dimethylbutyloxy)ethyl, (2-ethylhexyloxy)ethyl, n-octyloxyethyl, (3,5,5-trimethylhexyloxy)ethyl, (2-methyl-1-isopropylpropyloxy)ethyl, (3-methyl-1-isopropylbutyloxy)ethyl, 2-ethoxy-1-methylethyl, 3-methoxybutyl, (3,3,3-trifluoropropyloxy)ethyl, or (3,3,3-trichloropropyloxy)ethyl;

alkyl substituted by alkoxyalkoxy such as methoxymethoxymethyl, methoxyethoxyethyl, ethoxyethoxyethyl, n-propyloxyethoxyethyl, n-butyloxyethoxyethyl, cyclohexyloxyethoxyethyl, decalyloxypropyloxyethoxy, (1,2-dimethylpropyloxy)ethoxyethyl, (3-methyl-1-isobutylbutyloxy)ethoxyethyl, (2-methoxy-1-methylethoxy)ethyl, (2-butyloxy-1-methylethoxy)ethyl, 2-(2'-ethoxy-1'-methylethoxy)-1-methylethyl, (3,3,3-trifluoropropyloxy)ethoxyethyl, or (3,3,3-trichloropropyloxy)ethoxyethyl;

alkyl substituted by alkoxyalkoxyalkoxy such as methoxymethoxymethoxymethyl, methoxyethoxyethoxyethyl, ethoxyethoxyethoxyethyl, n-butyloxyethoxyethoxyethyl, cyclohexyloxyethoxyethoxyethyl, n-propyloxypropyloxypropyloxyethyl, (2,2,2-trifluoroethoxy)ethoxyethoxyethyl, or (2,2,2-trichloroethoxy)ethoxy-ethoxyethyl;

alkyl substituted by acyl such as formylmethyl, 2-oxobutyl, 3-oxobutyl, 4-oxobutyl, 2,6-dioxocyclohexan-1-yl, 2-oxo-5-tert-butylcyclohexan-1-yl;

alkyl substituted by acyloxy such as formyloxymethyl, acetoxyethyl, n-propionyloxyethyl, n-butanoyloxyethyl, valeryloxyethyl, (2-ethylhexanoyloxy)ethyl, (3,5-trimethylhexanoyloxy)ethyl, (3,5,5-trimethylhexanoyloxy)hexyl, (3-fluorobutyryloxy)ethyl, or (3-chlorobutyryloxy)ethyl;

alkyl substituted by acyloxyalkoxy such as formyloxymethoxymethyl, acetoxyethoxyethyl, n-propionyloxyethoxyethyl, valeryloxyethoxyethyl, (2-ethylhexanoyloxy)ethoxyethyl, (3,5,5-trimethylhexanoyl)oxybutyloxyethyl, (3,5,5-trimethylhexanoyloxy)ethoxyethyl, (2-fluoropropionyloxy)ethoxyethyl, or (2-chloropropionyloxy)ethoxyethyl;

alkyl substituted by acyloxyalkoxyalkoxy such as acetoxymethoxymethoxymethyl, acetoxyethoxyethoxyethyl, n-propionyloxy-ethoxyethoxyethyl, valeryloxyethoxyethoxyethyl, (2-ethylhexanoyloxy)-ethoxyethoxyethyl, (3,5,5-trimethylhexanoyloxy)ethoxyethoxyethyl, (2-fluoropropionyloxy)ethoxyethoxyethyl, or (2-chloropropionyloxy)ethoxyethoxyethyl;

alkyl substituted by alkoxycarbonyl such as methoxycarbonylmethyl, ethoxycarbonylmethyl, n-butyloxycarbonylmethyl, methoxycarbonylethyl, ethoxycarbonylethyl, n-butyloxycarbonylethyl, (4-ethylcyclohexyloxy-carbonyl)cyclohexyl, (2,2,3,3-tetrafluoropropyloxycarbonyl)methyl, or (2,2,3,3-tetrachloropropyloxycarbonyl)methyl;

alkyl substituted by aryloxycarbonyl such as phenyloxycarbonylmethyl, (2-methylphenyloxycarbonyl)methyl, (3-methylphenyloxycarbonyl)methyl, (4-methylphenyloxycarbonyl)methyl, (4-tert-butylphenyloxycarbonyl)methyl, phenyloxycarbonylethyl, (4-tert-butylphenyloxycarbonyl)ethyl, (1-naphthyl-oxycarbonyl)methyl, (2-naphthyloxycarbonyl)methyl, (2-phenylphenyloxy-carbonyl)ethyl, (3-phenylphenyloxycarbonyl)ethyl, or (4-phenylphenyloxycarbonyl)ethyl;

alkyl substituted by aralkyloxycarbonyl such as benzyloxycarbonylmethyl, benzyloxycarbonylethyl, phenethyloxycarbonylmethyl, or (4-cyclohexyloxy-benzyloxycarbonyl)methyl;

alkyl substituted by alkenyloxycarbonyl such as vinyloxycarbonylmethyl, vinyloxycarbonylethyl, allyloxycarbonylmethyl, cyclopentadienyloxycarbonylmethyl, or octenoxycarbonylmethyl;

alkyl substituted by alkoxycarbonyloxy such as methoxycarbonyloxymethyl, methoxycarbonyloxyethyl, ethoxycarbonyloxyethyl, butyloxycarbonyloxyethyl, (2,2,2-trifluoroethoxycarbonyloxy)ethyl, or (2,2,2-trichloroethoxycarbonyloxy)ethyl;

alkyl substituted by alkoxyalkoxycarbonyloxy such as methoxymethoxycarbonyloxymethyl, methoxyethoxycarbonyloxyethyl, ethoxyethoxycarbonyloxyethyl, n-butyloxyethoxycarbonyloxyethyl, (2,2,2-trifluoroethoxy)ethoxycarbonyloxyethyl, or (2,2,2-trichloroethoxy)ethoxycarbonyloxyethyl;

alkyl substituted by dialkylamino such as dimethylaminomethyl, diethylaminomethyl, di-n-butylaminomethyl, di-n-hexylaminomethyl, di-n-octylaminomethyl, di-n-decylaminomethyl, N-isoamyl-N-methylaminomethyl, piperidinomethyl, di(methoxymethyl)aminomethyl, di(methoxyethyl)aminomethyl, di(ethoxymethyl)aminomethyl, di(ethoxyethyl)aminomethyl, di(n-propyloxyethyl)aminomethyl, di(n-butyloxyethyl)aminomethyl, bis(2-cyclohexyloxyethyl)aminomethyl, dimethylaminoethyl, diethylaminoethyl, di-n-butylaminoethyl, di-n-hexylaminoethyl, di-n-octylaminoethyl, di-n-decylaminoethyl, N-isoamyl-N-methylaminoethyl, piperidinoethyl, di(methoxymethyl)aminoethyl, di(methoxyethyl)aminoethyl, di(ethoxymethyl)aminoethyl, di(ethoxyethyl)aminoethyl, di(n-propyloxyethyl)aminoethyl, di(n-butyloxyethyl)aminoethyl, bis(2-cyclohexyloxyethyl)aminoethyl, dimethylaminopropyl, diethylaminopropyl, di-n-butylaminopropyl, di-n-hexylaminopropyl, di-n-octylaminopropyl, di-n- decylaminopropyl, N-isoamyl-N-methylaminopropyl, piperidinopropyl, di(methoxymethyl)aminopropyl, di(methoxyethyl)aminopropyl, di(ethoxymethyl)aminopropyl, di(ethoxyethyl)aminopropyl, di(n-propyloxyethyl)aminopropyl, di(n-butyloxyethyl)aminopropyl, bis(2-cyclohexyloxyethyl)aminopropyl, dimethylaminobutyl, diethylaminobutyl, di-n-butylaminobutyl, di-n-hexylaminobutyl, di-n-octylaminobutyl, di-n-decylaminobutyl, N-isoamyl-N-methylaminobutyl, piperidinobutyl, di(methoxymethyl)aminobutyl, di(methoxyethyl)aminobutyl, di(ethoxymethyl)aminobutyl, di(ethoxyethyl)aminobutyl, di(n-propyloxyethyl)aminobutyl, di(n-butyloxyethyl)aminobutyl, or bis(2-cyclohexyloxyethyl)aminobutyl;

alkyl substituted by acylamino such as acetylaminomethyl, acetylaminoethyl, n-propionylaminoethyl, n-butanoylaminoethyl, cyclohexylcarbonylaminoethyl, 4-methylcyclohexylcarbonylaminoethyl, or succiniminoethyl;

alkyl substituted by alkylsulfonamino such as methylsulfonaminomethyl, methylsulfonaminoethyl, ethylsulfonaminoethyl, n-propylsulfonaminoethyl, or n-octylsulfonaminoethyl;

alkyl substituted by alkylsulfonyl such as methylsulfonylmethyl, ethylsulfonylmethyl, butylsulfonylmethyl, methylsulfonylethyl, ethylsulfonylethyl, n-butylsulfonylethyl, 2-ethylhexylsulfonylethyl, 2,2,3,3-tetrafluoropropylsulfonylmethyl, or 2,2,3,3-tetrachloropropylsulfonylmethyl;

alkyl substituted by arylsulfonyl such as phenylsulfonylmethyl, phenylsulfonylethyl, phenylsulfonylpropyl, phenylsulfonylbutyl, 2-methylphenylsulfonylmethyl, 3-methylphenylsulfonylmethyl, 4-methylphenylsulfonylmethyl, 4-methylphenylsulfonylethyl, 4-methylphenylsulfonylpropyl, 4-methylphenylsulfonylbutyl, 2,4-dimethylphenylsulfonylmethyl, 2,6-dimethylphenylsulfonylmethyl, 2,4-dimethylphenylsulfonylethyl, 2,4-dimethylphenylsulfonylpropyl, or 2,4-dimethylphenylsulfonylbutyl; and alkyl substituted by heterocycle such as thiadiazolinomethyl, pyrrolinomethyl, pyrrolidinomethyl, pyrazolidinomethyl, imidazolidinomethyl, oxazolyl, triazolinomethyl, morpholinomethyl, indolinomethyl, benzimidazolinomethyl, carbazolinomethyl.

The substituted or unsubstituted aralkyl group to substitute a ring AR is an aralkyl group which may have an alkyl group as mentioned above as a substituent or may have the same substituent as the alkyl group as mentioned above may have. Specific examples include substituted or unsubstituted aralkyl groups such as benzyl, phenethyl, α-methylbenzyl, α,α-dimethylbenzyl, 1-naphthylmethyl, 2-naphthylmethyl, furfuryl, 2-methylbenzyl, 3-methylbenzyl, 4-methylbenzyl, 4-ethylbenzyl, 4-isopropylbenzyl, 4-tert-butylbenzyl, 4-n-hexylbenzyl, 4-n-nonylbenzyl, 3,4-dimethylbenzyl, 3-methoxybenzyl, 4-methoxybenzyl, 4-ethoxybenzyl, 4-n-butyloxybenzyl, 4-n-hexyloxybenzyl, 4-n-nonyloxybenzyl, 3-fluorobenzyl, 4-fluorobenzyl, 2-chlorobenzyl, and 4-chlorobenzyl.

As examples of substituted or unsubstituted aromatic ring group to substitute a ring AR, there are an unsubstituted carbocyclic aromatic ring group and heterocyclic aromatic ring group, a carbocyclic aromatic ring group or heterocyclic aromatic ring group having an alkyl group as mentioned above as a substituent, or carbocyclic aromatic ring group or heterocyclic aromatic ring group having the same substituent as the alkyl group as mentioned above may have. Specific examples include aromatic ring groups such as a substituted or unsubstituted carbocyclic aromatic group such as phenyl, 4-methylphenyl, 3-methylphenyl, 2-methylphenyl, 4-ethylphenyl, 3-ethylphenyl, 2-ethylphenyl, 4-n-propylphenyl, 4-isopropylphenyl, 2-isopropylphenyl, 4-n-butylphenyl, 4-isobutylphenyl, 4-sec-butylphenyl, 2-sec-butylphenyl, 4-tert-butylphenyl, 3-tert-butylphenyl, 2-tert-butylphenyl, 4-n-pentylphenyl, 4-isopentylphenyl, 4-neopentylphenyl, 4-tert-pentylphenyl, 4-n-hexylphenyl, 4-(2'-ethylbutyl)phenyl, 4-n-heptylphenyl, 4-n-octylphenyl, 4-(2'-ethylhexyl)phenyl, 4-n-nonylphenyl, 4-n-decylphenyl, 4-n-undecylphenyl, 4-n-dodecylphenyl, 4-n-tetradecylphenyl, 4-cyclohexylphenyl, 4-(4'-methylcyclohexyl)phenyl, 4-(4'-tert-butylcyclohexyl)phenyl, 3-cyclohexylphenyl, 2-cyclohexylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,4,5-trimethylphenyl, 2,3,5,6-tetramethylphenyl, 2,4-diethylphenyl, 2,6-diethylphenyl, 2,5-diisopropylphenyl, 2,6-diisopropylphenyl, 2,6-diisobutylphenyl, 2,4-di-tert-butylphenyl, 2,5-di-tert-butylphenyl, 4,6-di-tert-butyl-2-methylphenyl, 5-tert-butyl-2-methylphenyl, 4-tert-butyl-2,6-dimethylphenyl, 1-naphthyl, 2-naphthyl, 1,2,3,4-tetrahydro-5-naphthyl, 1,2,3,4-tetrahydro-6-naphthyl, 4-ethyl-1-naphthyl, 6-n-butyl-2-naphthyl, 5-indanyl, 4-methoxyphenyl, 3-methoxyphenyl, 2-methoxyphenyl, 4-ethoxyphenyl, 3-ethoxyphenyl, 2-ethoxyphenyl, 4-n-propyloxyphenyl, 3-n-propyloxyphenyl, 4-isopropyloxyphenyl, 2-isopropyloxyphenyl, 4-n-butyloxyphenyl, 4-isobutyloxyphenyl, 2-sec-butyloxyphenyl, 4-n-pentyloxyphenyl, 4-isopentyloxyphenyl, 2-isopentyloxyphenyl, 4-neopentyloxyphenyl, 2-neopentyloxyphenyl, 4-n-hexyloxyphenyl, 4-(2'-ethylbutyl)oxyphenyl, 4-n-heptyloxyphenyl, 4-n-octyloxyphenyl, 4-n-nonyloxyphenyl, 4-n-decyloxyphenyl, 4-n-undecyloxyphenyl, 4-n-dodecyloxyphenyl, 4-n-tetradecyloxyphenyl, 4-cyclohexyloxyphenyl, 2-cyclohexyloxyphenyl, 2,3-dimethoxyphenyl, 2,4-dimethoxyphenyl, 2,5-dimethoxyphenyl, 3,4-dimethoxyphenyl, 3,5-dimethoxyphenyl, 3,5-diethoxyphenyl, 2-methoxy-4-methylphenyl, 2-methoxy-5-methylphenyl, 2-methyl-4-methoxyphenyl, 3-methyl-4-methoxyphenyl, 3-methyl-5-methoxyphenyl, 2-methoxy-1-naphthyl, 4-methoxy-1-naphthyl, 4-n-butyloxy-1-naphthyl, 5-ethoxy-1-naphthyl, 6-methoxy-2-naphthyl, 6-ethoxy-2-naphthyl, 6-n-butyloxy-2-naphthyl, 6-n-hexyloxy-2-naphthyl, 7-methoxy-2-naphthyl, 7-n-butyloxy-2-naphthyl, 4-phenylphenyl, 3-phenylphenyl, 2-phenylphenyl, 4-(4'-methylphenyl)phenyl, 4-(3'-methylphenyl)phenyl, 4-(4'-ethylphenyl)phenyl, 4-(4'-isopropylphenyl)-phenyl, 4-(4'-tert-butylphenyl)phenyl, 4-(4'-n-hexylphenyl)phenyl, 4-(4'-n-octylphenyl)phenyl, 4-(4'-methoxyphenyl)phenyl, 4-(4'-n-butyloxyphenyl)-phenyl, 2-(2'-methoxyphenyl)phenyl, 4-(4'-chlorophenyl)phenyl, 3-methyl-4-phenylphenyl, 3-methoxy-4-phenylphenyl, 9-phenyl-2-fluorenyl, 9,9-diphenyl-2-fluorenyl, 9-methyl-9-phenyl-2-fluorenyl, 9-ethyl-9-phenyl-2-fluorenyl, 4-fluorophenyl, 3-fluorophenyl, 2-fluorophenyl, 4-chlorophenyl, 3-chlorophenyl, 2-chlorophenyl, 4-bromophenyl, 2-bromophenyl, 4-trifluoromethylphenyl, 2,3-difluorophenyl, 2,4-difluorophenyl, 2,5-difluorophenyl, 2,6-difluorophenyl, 3,4-difluorophenyl, 3,5-difluorophenyl, 2,3-dichlorophenyl, 2,4-dichlorophenyl, 2,5-dichlorophenyl, 3,4-dichlorophenyl, 3,5-dichlorophenyl, 2,5-dibromophenyl, 2,4,6-trichlorophenyl, 2-fluoro-4-methylphenyl, 2-fluoro-5-methylphenyl, 3-fluoro-2-methylphenyl, 3-fluoro-4-methylphenyl, 2-methyl-4-fluorophenyl, 2-methyl-5-fluorophenyl, 3-methyl-4-fluorophenyl, 2-chloro-4-methylphenyl, 2-chloro-5-methylphenyl, 2-chloro-6-methylphenyl, 3-chloro-4-methylphenyl, 2-methyl-3-chlorophenyl, 2-methyl-4-chlorophenyl, 3-methyl-4-chlorophenyl, 2-chloro-4,6-dimethylphenyl, 2,4-dichloro-1-naphthyl, 1,6-dichloro-2-naphthyl, 2-methoxy-4-fluorophenyl, 3-methoxy-4- fluorophenyl, 2-fluoro-4-methoxyphenyl, 2-fluoro-4-ethoxyphenyl, 2-fluoro-6-methoxyphenyl, 3-fluoro-4-methoxyphenyl, 3-fluoro-4-ethoxyphenyl, 2-chloro-4-methoxyphenyl, 3-chloro-4-methoxyphenyl, 2-methoxy-5-chlorophenyl, 3-methoxy-4-chlorophenyl, 3-methoxy-6-chlorophenyl, 5-chloro-2,4-dimethoxyphenyl, 2-hydroxyphenyl, 3-hydroxyphenyl, 4-hydroxyphenyl, 2-nitrophenyl, 3-nitrophenyl, 4-nitrophenyl, 2-cyanophenyl, 3-cyanophenyl, 4-cyanophenyl, 2-methyl-5-nitrophenyl, 3,5-dinitrophenyl, or 2-hydroxy-4-nitrophenyl; and a substituted or unsubstituted heterocyclic aromatic group such as 4-pyridyl, 3-pyridyl, 2-pyridyl, 4-methyl-2-pyridyl, 5-methyl-2-pyridyl, 6-methyl-2-pyridyl, 4,6-dimethyl-2-pyridyl, 4-methyl-5-nitro-2-pyridyl, 3-hydroxy-2-pyridyl, 6-fluoro-3-pyridyl, 6-methoxy-3-pyridyl, 6-methoxy-2-pyridyl, 2-pyrimidyl, 4-pyrimidyl, 5-pyrimidyl, 2,6-dimethyl-4-pyrimidyl, 4-quinolyl, 3-quinolyl, 4-methyl-2-quinolyl, 3-furyl, 2-furyl, 3-thienyl, 2-thienyl, 4-methyl-3-thienyl, 5-methyl-2-thienyl, 3-methyl-2-thienyl, 2-oxazolyl, 2-thiazolyl, 2-thiadiazolyl, 2-benzoxazolyl, 2-benzothiazolyl, or 2-benzoimidazolyl; and substituted or unsubstituted metallocenyl such as ferrocenyl, cobaltocenyl, nickelocenyl, dichlorotitanocenyl, trichlorotitaniumcyclopentadienyl, bis(trifluoromethanesulfonato)titanocenyl, dichlorozirconocenyl, dimethylzirconocenyl, diethoxyzirconocenyl, bis(cyclopentadienyl) chromium, bis(cyclopentadienyl)dichloromolybdenum, bis(cyclopentadienyl)dichlorohafnium, bis(cyclopentadienyl)dichloroniobium, bis(cyclopentadienyl)ruthenium, bis(cyclopentadienyl)vanadium, bis(cyclopentadienyl)dichlorovanadium, octamethylferrocenyl, octamethylcobaltocenyl, or octamethylnickelocenyl.

The substituted or unsubstituted alkoxy group to substitute a ring AR is an alkoxy group which may have an alkyl group as mentioned above as a substituent or an alkoxy group which may have the same substituent as the alkyl group as mentioned above may have. Specific examples include straight, branched, or cyclic unsubstituted alkoxy such as methoxy, ethoxy, n-propyloxy, isopropyloxy, n-butyloxy, isobutyloxy, tert-butyloxy, sec-butyloxy, n-pentyloxy, isopentyloxy, tert-pentyloxy, sec-pentyloxy, cyclopentyloxy, n-hexyloxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,3-dimethylbutyloxy, 1,1,2-trimethylpropyloxy, 1,2,2-trimethylpropyloxy, 1-ethylbutyloxy, 2-ethylbutyloxy, 1-ethyl-2-methylpropyloxy, cyclohexyloxy, methylcyclopentyloxy, n-heptyloxy, 1-methylhexyloxy, 2-methylhexyloxy, 3-methylhexyloxy, 4-methylhexyloxy, 5-methylhexyloxy, 1,1-dimethylpentyloxy, 1,2-dimethylpentyloxy, 1,3-dimethylpentyloxy, 1,4-dimethylpentyloxy, 2,2-dimethylpentyloxy, 2,3-dimethylpentyloxy, 2,4-dimethylpentyloxy, 3,3-dimethylpentyloxy, 3,4-dimethylpentyloxy, 1-ethylpentyloxy, 2-ethylpentyloxy, 3-ethylpentyloxy, 1,1,2-trimethylbutyloxy, 1,1,3-trimethylbutyloxy, 1,2,3-trimethylbutyloxy, 1,2,2-trimethylbutyloxy, 1,3,3-trimethylbutyloxy, 2,3,3-trimethylbutyloxy, 1-ethyl-1-methylbutyloxy, 1-ethyl-2-methylbutyloxy, 1-ethyl-3-methylbutyloxy, 2-ethyl-1-methylbutyloxy, 2-ethyl-3-methylbutyloxy, 1-n-propylbutyloxy, 1-isopropylbutyloxy, 1-isopropyl-2-methylpropyloxy, methylcyclohexyloxy, n-octyloxy, 1-methylheptyloxy, 2-methylheptyloxy, 3-methylheptyloxy, 4-methylheptyloxy, 5-methylheptyloxy, 6-methylheptyloxy, 1,1-dimethylhexyloxy, 1,2-dimethylhexyloxy, 1,3-dimethylhexyloxy, 1,4-dimethylhexyloxy, 1,5-dimethylhexyloxy, 2,2-dimethylhexyloxy, 2,3-dimethylhexyloxy, 2,4-dimethylhexyloxy, 2,5-dimethylhexyloxy, 3,3-dimethylhexyloxy, 3,4-dimethylhexyloxy, 3,5-dimethylhexyloxy, 4,4-dimethylhexyloxy, 4,5-dimethylhexyloxy, 1-ethylhexyloxy, 2-ethylhexyloxy, 3-ethylhexyloxy, 4-ethylhexyloxy, 1-n-propylpentyloxy, 2-n-propylpentyloxy, 1-isopropylpentyloxy, 2-isopropylpentyloxy, 1-ethyl-1-methylpentyloxy, 1-ethyl-2-methylpentyloxy, 1-ethyl-3-methylpentyloxy, 1-ethyl-4-methylpentyloxy, 2-ethyl-1-methylpentyloxy, 2-ethyl-2-methylpentyloxy, 2-ethyl-3-methylpentyloxy, 2-ethyl-4-methylpentyloxy, 3-ethyl-1-methylpentyloxy, 3-ethyl-2-methylpentyloxy, 3-ethyl-3-methylpentyloxy, 3-ethyl-4-methylpentyloxy, 1,1,2-trimethylpentyloxy, 1,1,3-trimethylpentyloxy, 1,1,4-trimethylpentyloxy, 1,2,2-trimethylpentyloxy, 1,2,3-trimethylpentyloxy, 1,2,4-trimethylpentyloxy, 1,3,4-trimethylpentyloxy, 2,2,3-trimethylpentyloxy, 2,2,4-trimethylpentyloxy, 2,3,4-trimethylpentyloxy, 1,3,3-trimethylpentyloxy, 2,3,3-trimethylpentyloxy, 3,3,4-trimethylpentyloxy, 1,4,4-trimethylpentyloxy, 2,4,4-trimethylpentyloxy, 3,4,4-trimethylpentyloxy, 1-n-butylbutyloxy, 1-isobutylbutyloxy, 1-sec-butylbutyloxy, 1-tert-butylbutyloxy, 2-tert-butylbutyloxy, 1-n-propyl-1-methylbutyloxy, 1-n-propyl-2-methylbutyloxy, 1-n-propyl-3-methylbutyloxy, 1-isopropyl-1-methylbutyloxy, 1-isopropyl-2-methylbutyloxy, 1-isopropyl-3-methylbutyloxy, 1,1-diethylbutyloxy, 1,2-diethylbutyloxy, 1-ethyl-1,2-dimethylbutyloxy, 1-ethyl-1,3-dimethylbutyloxy, 1-ethyl-2,3-dimethylbutyloxy, 2-ethyl-1,1-dimethylbutyloxy, 2-ethyl-1,2-dimethylbutyloxy, 2-ethyl-1,3-dimethylbutyloxy, 2-ethyl-2,3-dimethylbutyloxy, 1,1,3,3-tetramethylbutyloxy, 1,2-dimethylcyclohexyloxy, 1,3-dimethylcyclohexyloxy, 1,4-dimethylcyclohexyloxy, ethylcyclohexyloxy, n-nonyloxy, 3,5,5-trimethylhexyloxy, n-decyloxy, n-undecyloxy, n-dodecyloxy, 1-adamantyloxy, or n-pentadecyloxy;

alkoxy substituted by alkoxy such as methoxymethoxy, methoxyethoxy, ethoxyethoxy, n-propyloxyethoxy, isopropyloxyethoxy, n-butyloxyethoxy, isobutyloxyethoxy, tert-butyloxyethoxy, sec-butyloxyethoxy, n-pentyloxyethoxy, isopentyloxyethoxy, tert-pentyloxyethoxy, sec-pentyloxyethoxy, cyclopentyloxyethoxy, n-hexyloxyethoxy, ethylcyclohexyloxyethoxy, n-nonyloxyethoxy, (3,5,5-trimethylhexyloxy)ethoxy, (3,5,5-trimethylhexyloxy)butyloxy, n-decyloxyethoxy, n-undecyloxyethoxy, n-dodecyloxyethoxy, 3-methoxypropyloxy, 3-ethoxypropyloxy, 3-(n-propyloxy)propyloxy, 2-isopropyloxypropyloxy, 2-methoxybutyloxy, 2-ethoxybutyloxy, 2-(n-propyloxy)butyloxy, 4-isopropyloxybutyloxy, decalyloxyethoxy, or adamantyloxyethoxy;

straight, branched, or cyclic alkoxy substituted by alkoxyalkoxy such as methoxymethoxymethoxy, ethoxymethoxymethoxy, propyloxymethoxymethoxy, butyloxymethoxymethoxy, methoxyethoxymethoxy, ethoxyethoxymethoxy, propyloxyethoxymethoxy, butyloxyethoxymethoxy, methoxypropyloxymethoxy, ethoxypropyloxymethoxy, propyloxypropyloxymethoxy, butyloxypropyloxymethoxy, methoxybutyloxymethoxy, ethoxybutyloxymethoxy, propyloxybutyloxymethoxy, butyloxybutyloxymethoxy, methoxymethoxyethoxy, ethoxymethoxyethoxy, propyloxymethoxyethoxy, butyloxymethoxyethoxy, methoxyethoxyethoxy, ethoxyethoxyethoxy, propyloxyethoxyethoxy, butyloxyethoxyethoxy, methoxypropyloxyethoxy, ethoxypropyloxyethoxy, propyloxypropyloxyethoxy, butyloxypropyloxyethoxy, methoxybutyloxyethoxy, ethoxybutyloxyethoxy, propyloxybutyloxyethoxy, butyloxybutyloxyethoxy, methoxymethoxypropyloxy, ethoxymethoxypropyloxy, propyloxymethoxypropyloxy, butyloxymethoxypropyloxy, methoxyethoxypropyloxy, ethoxyethoxypropyloxy, propyloxyethoxypropyloxy, butyloxyethoxypropyloxy, methoxypropyloxypropyloxy, ethoxypropyloxypropyloxy, propyloxypropyloxypropyloxy, butyloxypropyloxypropyloxy, methoxybutyloxypropyloxy, ethoxybutyloxypropyloxy, propylbutyloxypropyloxy, butyloxybutyloxypropyloxy, methoxymethoxybutyloxy, ethoxymethoxybutyloxy, propyloxymethoxybutyloxy, butyloxymethoxybutyloxy, methoxyethoxybutyloxy, ethoxyethoxybutyloxy, propyloxyethoxybutyloxy, butyloxyethoxybutyloxy, methoxypropyloxybutyloxy, ethoxypropyloxybutyloxy, propyloxypropyloxybutyloxy, butyloxypropyloxybutyloxy, methoxybutyloxybutyloxy, ethoxybutyloxybutyloxy, propyloxybutyloxybutyloxy, butyloxybutyloxybutyloxy, (4-ethylcyclohexyloxy)ethoxyethoxy, (2-ethyl-1-hexyloxy)ethoxypropyloxy, or [4-(3,5,5-trimethylhexyloxy)butyloxy]ethoxy;

alkoxy substituted by alkoxycarbonyl such as methoxycarbonylmethoxy, ethoxycarbonylmethoxy, n-propyloxycarbonylmethoxy, isopropyloxycarbonylmethoxy, or (4'-ethylcyclohexyloxy)carbonylmethoxy;

alkoxy substituted by acyl such as acetylmethoxy, ethylcarbonylmethoxy, n-octylcarbonylmethoxy, or phenacyloxy; and alkoxy substituted by acyloxy such as acetyloxymethoxy, acetyloxyethoxy, acetyloxyhexyloxy, or n-butanoyloxycyclohexyloxy;

alkoxy substituted by alkylamino such as methylaminomethoxy, 2-methylaminoethoxy, 2-(2-methylaminoethoxy)ethoxy, 4-methylaminobutyloxy, 1-methylaminopropan-2-yloxy, 3-methylaminopropyloxy, 2-methylamino-2-methylpropyloxy, 2-ethylaminoethoxy, 2-(2-ethylaminoethoxy)ethoxy, 3-ethylaminopropyloxy, 1-ethylaminopropyloxy, 2-isopropylaminoethoxy, 2-(n-butylamino)ethoxy, 3-(n-hexylamino)propyloxy, or 4-(cyclohexylamino)butyloxy;

alkoxy substituted by alkylaminoalkoxy such as methylaminomethoxymethoxy, methylaminoethoxyethoxy, methylaminoethoxypropyloxy, ethylaminoethoxypropyloxy, or 4-(2'-isobutylaminopropyloxy)butyloxy;

alkoxy substituted by dialkylamino such as dimethylaminomethoxy, 2-dimethylaminoethoxy, 2-(2-dimethylaminoethoxy)ethoxy, 4-dimethylaminobutyloxy, 1-dimethylaminopropan-2-yloxy, 3-dimethylaminopropyloxy, 2-dimethylamino-2-methylpropyloxy, 2-diethylaminoethoxy, 2-(2-diethylaminoethoxy)ethoxy, 3-diethylaminopropyloxy, 1-diethylaminopropyloxy, 2-diisopropylaminoethoxy, 2-(di-n-butylamino)ethoxy, 2-piperidylethoxy, or 3-(di-n-hexylamino)propyloxy;

alkoxy substituted by dialkylaminoalkoxy such as dimethylaminomethoxymethoxy, dimethylaminoethoxyethoxy, dimethylaminoethoxypropyloxy, diethylaminoethoxypropyloxy, or 4-(2'-diisobutylaminopropyloxy)butyloxy;

alkoxy substituted by alkylthio such as methylthiomethoxy, 2-methylthioethoxy, 2-ethylthioethoxy, 2-n-propylthioethoxy, 2-isopropylthioethoxy, 2-n-butylthioethoxy, 2-isobutylthioethoxy, or (3,5,5-trimethylhexylthio)hexyloxy;

alkoxy substituted by metallocenyl such as ferrocenylmethoxy, ferrocenylethoxy, ferrocenylpropyloxy, ferrocenylbutyloxy, ferrocenylpentyloxy, ferrocenylhexyloxy, ferrocenylheptyloxy, ferrocenyloctyloxy, ferrocenyinonyloxy, ferrocenyldecyloxy, cobaltocenylmethoxy, cobaltocenylethoxy, cobaltocenylpropyloxy, cobaltocenylbutyloxy, cobaltocenylpentyloxy, cobaltocenylhexyloxy, cobaltocenylheptyloxy, cobaltocenyloctyloxy, cobaltocenylnonyloxy, cobaltocenyldecyloxy, nickelocenylmethoxy, nickelocenylethoxy, nickelocenylpropyloxy, nickelocenylbutyloxy, nickelocenylpentyloxy, nickelocenylhexyloxy, nickelocenylheptyloxy, nickelocenyloctyloxy, nickelocenylnonyloxy, nickelocenyldecyloxy, dichlorotitanocenylmethoxy, trichlorotitaniumcyclopentadienylmethoxy, bis(trifluoromethanesulfonato)titanocenylmethoxy, dichlorozirconocenylmethoxy, bis(cyclopentadienyl)chromiummethoxy, bis(cyclopentadienyl)dichlorohafniummethoxy, bis(cyclopentadienyl)dichloroniobiummethoxy, bis(cyclopentadienyl)rutheniummethoxy, bis(cyclopentadienyl)vanadiummethoxy, bis(cyclopentadienyl)dichlorovanadiummethoxy, or bis(cyclopentadienyl)osmiummethoxy. Preferable examples include alkoxy groups of 1 to 12 carbon atoms such as methoxy, ethoxy, n-propyloxy, isopropyloxy, n-butyloxy, isobutyloxy, sec-butyloxy, tert-butyloxy, n-pentyloxy, isopentyloxy, neopentyloxy, 2-methylbutyloxy, 2-ethylhexyloxy, 3,5,5-trimethylhexyloxy, decalyloxy, methoxyethoxy, ethoxyethoxy, methoxyethoxyethoxy, ethoxyethoxyethoxy, and ferrocenylmethoxy.

The substituted or unsubstituted aralkyloxy group to substitute a ring AR is an aralkyloxy group which may have an alkyl group as mentioned above as a substituent or an aralkyloxy group which may have the same substituent as the alkyl group as mentioned above may have. Specific examples include aralkyloxy groups such as benzyloxy, 4-nitrobenzyloxy, 4-cyanobenzyloxy, 4-hydroxybenzyloxy, 2-methylbenzyloxy, 3-methylbenzyloxy, 4-methylbenzyloxy, 4-trifluoromethylbenzyloxy, 1-naphtylmethoxy, 2-naphtylmethoxy, 4-cyano-1-naphtylmethoxy, 4-hydroxy-1-naphtylmethoxy, 6-hydroxy-2-naphthylmethoxy, 4-methyl-1-naphtylmethoxy, 6-methyl-2-naphthylmethoxygroup, 4-trifluoromethyl-1-naphthylmethoxy, and fluorene-9-yl ethoxy.

The substituted or unsubstituted aryloxy group to substitute a ring AR is an aryloxy group which may have an alkyl group as mentioned above as a substituent or an aryloxy group which may have the same substituent as the alkyl group as mentioned above may have. Specific examples include aryloxy groups such as phenoxy, 2-methylphenoxy, 4-methylphenoxy, 4-tert-butylphenoxy, 2-methoxyphenoxy, 4-isopropylphenoxy, naphthyloxy, ferrocenyloxy, cobaltocenyloxy, nickelocenyloxy, octamethylferrocenyloxy, octamethylcobaltocenyloxy, and octamethylnickelocenyloxy.

As examples of the substituted or unsubstituted alkylthio group to substitute a ring AR, an alkylthio group which may have an alkyl group as mentioned above as a substituent or an alkylthio group which may have the same substituent as the alkyl group as mentioned above may have. Specific examples include alkylthio groups such as methylthio, ethylthio, n-propylthio, isopropylthio, n-butylthio, isobutylthio, sec-butylthio, tert-butylthio, n-pentylthio, isopentylthio, neopentylthio, 2-methylbutylthio, methylcarboxylethylthio, 2-ethylhexylthio, 3,5,5-trimethylhexylthio, and decalylthio.

As examples of the substituted or unsubstituted aralkylthio group to substitute a ring AR, an aralkylthio group which may have an alkyl group as mentioned above as a substituent or an aralkylthio group which may have the same substituent as the alkyl group as mentioned above may have. Specific examples include aralkylthio groups such as benzylthio, 4-cyanobenzylthio, 4-hydroxybenzylthio, 2-methylbenzylthio, 3-methylbenzylthio, 4-methylbenzylthio, 4-trifluoromethylbenzylthio, 1-naphthylmethylthio, 4-nitro-1-naphthylmethylthio, 4-cyano-1-naphthylmethylthio, 4-hydroxy-1-naphthylmethylthio, 4-methyl-1-naphthylmethylthio, 4-trifluoromethyl-1-naphthylmethylthio, and fluorene-9-yl ethylthio.

As examples of the substituted or unsubstituted arylthio group to substitute a ring AR, an arylthio group which may have an alkyl group as mentioned above as a substituent or an arylthio group which may have the same substituent as the alkyl group as mentioned above may have. Specific examples include arylthio groups such as phenylthio, 4-methylphenylthio, 2-methoxyphenylthio, 4-tert-butylphenylthio, naphthylthio, ferrocenylthio, cobaltocenylthio nickelocenylthio, octamethylferrocenylthio, octamethylcobaltocenylthio, and octamethylnickelocenylthio.

As examples of the substituted or unsubstituted amino group to substitute a ring AR, an amino group which may have an alkyl group as mentioned above as a substituent or an alkylamino group which may have the same substituent as the alkyl group as mentioned above may have. Specific examples include monoalkylamino groups such as amino, methylamino, ethylamino, propylamino, butylamino, pentylamino, hexylamino, heptylamino, octylamino, 2-ethylhexylamino, cyclohexylamino, 3,5,5-trimethylhexylamino, nonylamino, and decylamino; dialkylamino groups such as dimethylamino, diethylamino, methylethylamino, dibutylamino, piperidino, morpholino, di(acetyloxyethyl)amino, and di(propionyloxyethyl)amino;

aralkylamino groups which may have an alkyl group as mentioned above as a substituent or an aralkylamino group which may have the same substituent as the alkyl group as mentioned above may have, specific examples including monoaralkyl amino groups such as benzylamino, phenetylamino, 3-phenylpropylamino, 4-ethybenzylamino, 4-isopropylbenzylamino; and diaralkyl amino groups such as dibenzylamino, diphenetylamino, bis(4-ethylbenzyl)amino, and bis(4-isopropylbenzyl)amino;

arylamino groups which may have an alkyl group as mentioned above as a substituent or an arylamino group which may have the same substituent as the arylamino group as mentioned above may have, specific examples including monoarylamino such as phenylamino, 1-naphthylamino, 2-naphthylamino, 2-methylphenylamino, 3-methylphenylamino, 4-methylphenylamino, 2,4-dimethylphenylamino, 2,6-dimethylphenylamino, 4-ethylphenylamino, 4-isopropylphenylamino, 4-methoxyphenylamino, 4-chlorophenylamino, 4-acetylphenylamino, 4-methoxycarbonylphenylamino, 4-ethoxycarbonylphenylamino, or 4-propyloxycarbonylphenylamino;

diarylamino such as N,N-diphenylamino, N,N-di(3-methylphenyl)amino, N,N-di(4-methylphenyl)amino, N,N-di(4-ethylphenyl)amino, N,N-di(4-tert-butylphenyl)amino, N,N-di(4-n-hexylphenyl)amino, N, N-di(4-methoxyphenyl)amino, N, N-di(4-ethoxyphenyl)amino, N,N-di(4-n-butyloxyphenyl)amino, N, N-di(4-n-hexyloxyphenyl)amino, N,N-di(1-naphthyl)amino, N,N-di(2-naphthyl)amino, N-phenyl-N-(3-methylphenyl)amino, N-phenyl-N-(4-methylphenyl)amino, N-phenyl-N-(4-n-octylphenyl)amino, N-phenyl-N-(4-methoxyphenyl)amino, N-phenyl-N-(4-ethoxyphenyl)amino, N-phenyl-N-(4-n-hexyloxyphenyl)amino, N-phenyl-N-(4-fluorophenyl)amino, N-phenyl-N-(1-naphthyl)amino, N-phenyl-N-(2-naphthyl)amino, or N-phenyl-N-(4-phenylphenyl)amino;

acylamino groups which may have an alkyl group as mentioned above as a substituent or an acylamino group which may have the same substituent as that the alkyl group as mentioned above may have, specific examples including acylamino groups such as formylamino, acetylamino, propionylamino, benzoylamino, phenylacetylamino, and toluoylamino;

alkoxycarbonylamino groups which may have an alkyl group as mentioned above as a substituent or an alkoxycarbonylamino group which may have the same substituent as the alkyl group as mentioned above may have, specific examples including alkoxycarbonyl groups such as methoxycarbonylamino, ethoxycarbonylamino, propoxycarbonylamino, and butoxycarbonylamino;

aralkyloxycarbonylamino groups which may have an alkyl group as mentioned above as a substituent or an aralkyloxycarbonylamino group which may have the same substituent as the alkyl group as mentioned above may have, specific examples including aralkyloxycarbonylamino groups such as benzyloxycarbonylamino, and phenetyloxycarbonylamino;

aromatic ring oxycarbonylamino groups which may have an alkyl group as mentioned above as a substituent or an aromatic ring oxycarbonylamino group which may have the same substituent as the alkyl group as mentioned above may have, specific examples including aromatic ring oxycarbonylamino groups such as phenoxycarbonylamino, tolyloxycarbonylamino, and pyridyloxycarbonylamino; and alkenyloxycarbonylamino groups which may have an alkyl group as mentioned above as a substituent and an alkenyloxycarbonylamino group which may have the same substituent as the alkyl group as mentioned above may have, specific examples including alkenyloxycarbonylamino groups such as a vinyloxycarbonylamino, aryloxycarbonylamino, and butenoxycarbonylamino.

As examples of the substituted or unsubstituted acyl group to substitute a ring AR, an acyl group which may have an alkyl group as mentioned above as a substituent or an acyl group which may have the same substituent as the alkyl group as mentioned above may have, may be mentioned. Specific examples include acyl groups such as formyl, methylcarbonyl, ethylcarbonyl, n-propylcarbonyl, isopropylcarbonyl, n-butylcarbonyl, isobutylcarbonyl, sec-butylcarbonyl, tert-butylcarbonyl, n-pentylcarbonyl, isopentylcarbonyl, neopentylcarbonyl, 2-methylbutylcarbonyl, benzoyl, 2-methylbenzoyl, 3-methylbenzoyl, 4-methylbenzoyl, 4-ethylbenzoyl, 4-n-propylbenzoyl, 4-tert-butylbenzoyl, 4-nitrobenzylcarbonyl, 3-n-butoxy-2-naphthoyl, cinnamoyl, ferrocenecarbonyl, and 1-methylferrocene-1'-carbonyl.

As examples of the substituted or unsubstituted acyloxy group to substitute a ring AR, an acyloxy group which may have an alkyl group as mentioned above as a substituent or an acyloxy group which may have the same substituent as the alkyl group as mentioned above may have, may be mentioned. Specific examples include acyloxy groups such as formyloxy, methylcarbonyloxy, ethylcarbonyloxy, n-propylcarbonyloxy, iosopropylcarbonyloxy, n-butylcarbonyloxy, isobutylcarbonyloxy, sec-butylcarbonyloxy, tert-butylcarbonyloxy, n-pentylcarbonyloxy, isopentylcarbonyloxy, neopentylcarbonyloxy, 2-methylbutylcarbonyloxy, benzoyloxy, 2-metylbenzoyloxy, 3-methylbenzoyloxy, 4-methylbenzoyloxy, 4-ethylbenzoyloxy, 4-n-propylbenzoyloxy, 4-tert-butylbenzoyloxy, 4-nitrobenzylcarbonyloxy, 3-n-butoxy-2-naphtoyloxy, cinnamoyloxy, ferrocenecarbonyloxy, 1-methylferrocene-1'-carbonyloxy, cobaltcenecarobonyloxy, and nickelocenecarbonyloxy.

As examples of the substituted or unsubstituted alkoxycarbonyl group to substitute a ring AR, an alkoxycarbonyl group which may have an alkyl group as mentioned above as a substituent and an alkoxycarbonyl group which may have the same substituent as the alkyl group as mentioned above may have, may be mentioned. Specific examples include alkoxycarbonyl such as methoxycarbonyl, ethoxycarbonyl, n-propyloxycarbonyl, isopropyloxycarbonyl, n-butyloxycarbonyl, isobutyloxycarbonyl, sec-butyloxycarbonyl, tert-butyloxycarbonyl, n-pentyloxycarbonyl, isopentyloxycarbonyl, neopentyloxycarbonyl, 2-ethylhexyloxycarbonyl, 3,5,5-trimethylhexyloxycarbonyl, decalyloxycarbonyl, cyclohexyloxycarbonyl, 2-chloroethoxycarbonyl, hydroxymethoxycarbonyl, or 2-hydroxyethoxycarbonyl;

alkoxycarbonyl substituted by alkoxy groups such as methoxymethoxycarbonyl, methoxyethoxycarbonyl, ethoxyethoxycarbonyl, n-propyloxyethoxycarbonyl, n-butyloxyethoxycarbonyl, n-pentyloxyethoxycarbonyl, n-hexyloxyethoxyethyl, n-butyloxybutyloxycarbonyl, n-hexyloxybutyloxycarbonyl, hydroxymethoxymethoxycarbonyl, or hydroxyethoxyethoxycarbonyl;

alkoxycarbonyl substituted by alkoxyalkoxy groups such as methoxymethoxymethoxycarbonyl, methoxyethoxyethoxycarbonyl, ethoxyethoxyethoxycarbonyl, n-propyloxyethoxyethoxycarbonyl, n-butyloxyethoxyethoxycarbonyl, n-pentyloxyethoxyethoxycarbonyl, or n-hexyloxyethoxyethoxycarbonyl; and alkoxycarbonyl substituted by metallocenyl such as ferrocenylmethoxycarbonyl, ferrocenylethoxycarbonyl, ferrocenylpropyloxycarbonyl, ferrocenylbutyloxycarbonyl, ferrocenylpentyloxycarbonyl, ferrocenylhexyloxycarbonyl, ferrocenylheptyloxycarbonyl, ferrocenyloctyloxycarbonyl, ferrocenyinonyloxycarbonyl, ferrocenylbutyidecylcarbonyl, cobaltocenylmethoxycarbonyl, cobaltocenylethoxycarbonyl, cobaltocenylpropyloxycarbonyl, cobaltocenylbutyloxycarbonyl, cobaltocenylpentyloxycarbonyl, cobaltocenylhexyloxycarbonyl, cobaltocenylheptyloxycarbonyl, cobaltocenyloctyloxycarbonyl, cobaltocenylnonyloxycarbonyl, cobaltocenylbutyldecylcarbonyl, nickelocenylmethoxycarbonyl, nickelocenylethoxycarbonyl, nickelocenylpropyloxycarbonyl, nickelocenylbutyloxycarbonyl, nickelocenylpentyloxycarbonyl, nickelocenylhexyloxycarbonyl, nickelocenylheptyloxycarbonyl, nickelocenyloctyloxycarbonyl, nickelocenylnonyloxycarbonyl, nickelocenylbutyldecylcarbonyl, dichlorotitanocenylmethoxycarbonyl, trichlorotitaniumcyclopentadienylmethoxycarbonyl, bis(trifluoromethanesulfonato)titanocenylmethoxycarbonyl, dichlorozirconocenylmethoxycarbonyl, dimethylzirconocenylmethoxycarbonyl, diethoxyzirconocenylmethoxycarbonyl, bis(cyclopentadienyl)chromiummethoxycarbonyl, bis(cyclopentadienyl)dichlorohafniummethoxycarbonyl, bis(cyclopentadienyl)dichloroniobiummethoxycarbonyl, bis(cyclopentadienyl)rutheniummethoxycarbonyl, bis(cyclopentadienyl)vanadiummethoxycarbonyl, bis(cyclopentadienyl)dichlorovanadiummethoxycarbonyl, or bis(cyclopentadienyl)osmiummethoxycarbonyl.

As examples of the substituted or unsubstituted aralkyloxycarbonyl group to substitute a ring AR, an aralkyloxycarbonyl group which may have an alkyl group as mentioned above as a substituent and an aralkyloxycarbonyl group which may have the same substituent as the alkyl group as mentioned above may have, may be mentioned. Specific examples include aralkyloxycarbonyl groups such as benzyloxycarbonyl, 4-nitrobenzyloxycarbonyl, 4-cyanobenzyloxycarbonyl, 4-hydroxybenzyloxycarbonyl, 2-methylbenzyloxycarbonyl, 3-methylbenzyloxycarbonyl, 4-methylbenzyloxycarbonyl, 4-trifluoromethylbenzyloxycarbonyl, 1-naphthylmethoxycarbonyl, 2-naphthylmethoxycarbonyl, 4-cyano-1-naphthylmethoxycarbonyl, 4-hydroxy-1-naphthylmethoxycarbonyl, 6-hydroxy-2-naphthylmethoxycarbonyl, 4-methyl-1-naphthylmethoxycarbonyl, 6-methyl-2-naphthylmethoxycarbonyl, 4-trifluoromethyl-1-naphthylmethoxycarbonyl, and fluorene-9-yl-ethoxycarbonyl.

The substituted or unsubstituted aryloxycarbonyl group to substitute a ring AR is an aryloxycarbonyl group which may have an alkyl group as mentioned above as a substituent or an aryloxycarbonyl group which may have the same substituent as the alkyl group as mentioned above may have. Specific examples include aryloxycarbonyl groups such as phenyloxycarbonyl, 2-methylphenyloxycarbonyl, 4-methylphenyloxycarbonyl, 4-tert-butylphenyloxycarbonyl, 2-methoxyphenyloxycarbonyl, 4-isopropylphenyloxycarbonyl, naphthyloxycarbonyl, ferrocenyloxycarbonyl, cobaltocenyloxycarbonyl, nickelocenyloxycarbonyl, octamethylferrocenyloxycarbonyl, octamethylcobaltocenyloxycarbonyl, and octamethylnickelocenyloxycarbonyl.

As examples of the substituted or unsubstituted alkenyloxycarbonyl group to substitute a ring AR, an alkenyloxycarbonyl group which may have an alkyl group as mentioned above as a substituent or an alkenyloxycarbonyl group which may have the same substituent as the alkyl group as mentioned above may have, may be mentioned. Preferable examples include alkenyloxycarbonyl groups having from 3 to 11 carbon atoms such as vinyloxycarbonyl, propenyloxycarbonyl, 1-butenyloxycarbonyl, iso-butenyloxycarbonyl, 1-pentenyloxycarbonyl, 2-pentenyloxycarbonyl, cyclopentadienyloxycarbonyl, 2-methyl-1-butenyloxycarbonyl, 3-methyl-1-butenyloxycarbonyl, 2-methyl-2-butenyloxycarbonyl, 2,2-dicyanovinyloxycarbonyl, 2-cyano-2-methylcarboxyvinyloxycarbonyl, 2-cyano-2-methylsulfonevinyloxycarbonyl, styryloxycarbonyl, and 4-phenyl-2-butenyloxycarbonyl.

As examples of the substituted aminocarbonyl group to substitute a ring AR, a substituted aminocarbonyl group which may have an alkyl group as mentioned above as a substituent or a substituted aminocarbonyl group which may have the same substituent as the alkyl group as mentioned above may have, may be mentioned. Preferable examples include substituted aminocarbonyl groups such as monosubstituted aminocarbonyl such as monoalkylaminocarbonyl having 2 to 11 carbon atoms such as methylaminocarbonyl, ethylaminocarbonyl, propylaminocarbonyl, butylaminocarbonyl, pentylaminocarbonyl, hexylaminocarbonyl, heptylaminocarbonyl, octylaminocarbonyl, (2-ethylhexyl)aminocarbonyl, cyclohexylaminocarbonyl, (3,5,5-trimethylhexyl)aminocarbonyl, nonylaminocarbonyl, or decylaminocarbonyl;

monoaralkylaminocarbonyl having 8 to 11 carbon atoms such as benzylaminocarbonyl, phenethylaminocarbonyl, (3-phenylpropylaminocarbonyl, (4-ethylbenzyl)aminocarbonyl, (4-isopropylbenzyl)aminocarbonyl, (4-methylbenzyl)aminocarbonyl, (4-ethylbenzyl)aminocarbonyl, (4-allylbenzyl)aminocarbonyl, [4-(2-cyanoethyl)benzyl]aminocarbonyl, or [4-(2-acetoxyethyl)benzyl]aminocarbonyl;

monoarylaminocarbonyl having 7 to 11 carbon atoms such as anilinocarbonyl, naphthylaminocarbonyl, toluidinocarbonyl, xylidinocarbonyl, ethylanilinocarbonyl, isopropylanilinocarbonyl, methoxyanilinocarbonyl, ethoxyanilinocarbonyl, chloroanilinocarbonyl, acetylanilinocarbonyl, methoxycarbonylanilinocarbonyl, ethoxycarbonylanilinocarbonyl, propoxycarbonylanilinocarbonyl, 4-methylanilinocarbonyl, or 4-ethylanilinocarbonyl;

monoalkenylaminocarbonyl having 3 to 11 carbon atoms such as vinylaminocarbonyl, allylaminocarbonyl, butenylaminocarbonyl, pentenylaminocarbonyl, hexenylaminocarbonyl, cyclohexenylaminocarbonyl, octadienylaminocarbonyl, or adamantenylaminocarbonyl;

dialkylaminocarbonyl having 3 to 17 carbon atoms such as dimethylaminocarbonyl, diethylaminocarbonyl, methylethylaminocarbonyl, dipropylaminocarbonyl, dibutylaminocarbonyl, di-n-hexylaminocarbonyl, dicyclohexylaminocarbonyl, dioctylaminocarbonyl, pyrrolidinocarbonyl, piperidinocarbonyl, morpholinocarbonyl, bis(methoxyethyl)aminocarbonyl, bis(ethoxyethyl)aminocarbonyl, bis(propoxyethyl)aminocarbonyl, bis(butoxyethyl)aminocarbonyl, di(acetyloxyethyl)aminocarbonyl, di(hydroxyethyl)aminocarbonyl, N-ethyl-N-(2-cyanoethyl)aminocarbonyl, or di(propionyloxyethyl)aminocarbonyl;

diaralkylaminocarbonyl having 15 to 21 carbon atoms such as dibenzylaminocarbonyl, diphenethylaminocarbonyl, bis(4-ethylbenzyl)aminocarbonyl, or bis(4-isopropylbenzyl)aminocarbonyl;

diarylaminocarbonyl having 13 to 15 carbon atoms such as diphenylaminocarbonyl, ditolylaminocarbonyl, or N-phenyl-N-tolylaminocarbonyl; and dialkenylaminocarbonyl having 5 to 13 carbon atoms such as divinylaminocarbonyl, diallylaminocarbonyl, dibutenylaminocarbonyl, dipentenylaminocarbonyl, dihexenylaminocarbonyl, or N-vinyl-N-allylaminocarbonyl;

disubstituted aminocarbonyl having 4 to 11 carbon atoms and having a substituent selected from substituted or unsubstituted alkyl, aralkyl, aryl, and alkenyl such as N-phenyl-N-allylaminocarbonyl, N-(2-acetyloxyethyl)-N-ethylaminocarbonyl, N-tolyl-N-methylaminocarbonyl, N-vinyl-N-methylaminocarbonyl, or N-benzyl-N-allylaminocarbonyl.

As examples of the substituted or unsubstituted alkenyl group to substitute a ring AR, an alkenyl group which may have an alkyl group as mentioned above as a substituent or an alkenyl group which may have the same substituent as the alkyl group as mentioned above may have, may be mentioned. Preferable examples include alkenyl groups having from 2 to 10 carbon atoms such as vinyl, propenyl, 1-butenyl, iso-butenyl, 1-pentenyl, 2-pentenyl, 2-methyl1-butenyl, 3-methyl-1-butenyl, 2-methyl-2-butenyl, 2,2-dicyanovinyl, 2-cyano-2-methylcarboxylvinyl, 2-cyano-2-methylsulfonevinyl, styryl, and 4-phenyl-2-butenyl.

As examples of the substituted or unsubstituted alkenyloxy group to substitute a ring AR, an alkenyloxy group which may have an alkyl group as mentioned above as a substituent or an alkenyloxy group which may have the same substituent as the alkyl group as mentioned above may have, may be mentioned. Preferable examples include alkenyloxy groups having from 2 to 10 carbon atoms such as vinyloxy, propenyloxy, 1-butenyloxy, iso-butenyloxy, 1-pentenyloxy, 2-pentenyloxy, 2-methyl-1-butenyloxy, 3-methyl-1-butenyloxy, 2-methyl-2-butenyloxy, cyclopentadienyloxy, 2,2-dicyanovinyloxy, 2-cyano-2-methylcarboxylvinyloxy, 2-cyano-2-methylsulfonevinyloxy, styryloxy, 4-phenyl-2-butenyloxy, and cinnamylalkoxy.

As examples of the substituted or unsubstituted alkenylthio group to substitute a ring AR, an alkenylthio group which may have an alkyl group as mentioned above as a substituent or an alkenylthio group which may have the same substituent as the alkyl group as mentioned above may have, may be mentioned. Preferable examples include alkenylthio groups having from 2 to 10 carbon atoms such as vinylthio, allylthio, butenylthio, hexanedienylthio, cyclopentadienylthio, styrylthio, cyclohexenylthio, and decenylthio.

As examples of the substituted or unsubstituted heteroaryl group to substitute a ring AR, a heteroaryl group which may have an alkyl group as mentioned above as a substituent or a heteroaryl group which may have the same substituent as the alkyl group as mentioned above may have, may be mentioned. Preferable examples include unsubstituted heteroaryl such as furanyl, pyrrolyl, 3-pyrrolino, pyrazolyl, imidazolyl, oxazolyl, thiazolyl, 1,2,3-oxadiazolyl, 1,2,3-triazolyl, 1,2,4-triazolyl, 1,3,4-thiadiazolyl, pyridinyl, pyridazinyl, pyrimidinyl, pyrazinyl, piperazinyl, triazinyl, benzofuranyl, indolyl, thionaphthenyl, benzimidazolyl, benzothiazolyl, benzotriazol-2-yl, benzotriazol-1-yl, purinyl, quinolinyl, isoquinolinyl, coumarinyl, cinnolinyl, quinoxalinyl, dibenzofuranyl, carbazolyl, phenanthrolinyl, phenothiazinyl, flavonyl, phthalimidyl, or naphthylimidyl;

or heteroaryl substituted by following substituents:

halogen such asfluorine, chlorine, bromine, or iodide;

cyano;

alkyl such as methyl, ethyl, propyl, butyl, pentyl, hexyl, heptyl, octyl, decyl, methoxymethyl, ethoxyethyl, ethoxyethyl, or trifluoromethyl;

aralkyl such as benzyl or phenethyl;

aryl such as phenyl, tolyl, naphthyl, xylyl, mesyl, chlorophenyl, or methoxyphenyl;

alkoxy such as methoxy, ethoxy, propoxy, butoxy, pentoxy, hexyloxy, heptyloxy, octyloxy, nonyloxy, decyloxy, 2-ethylhexyloxy, 3,5,5-trimethylhexyloxy, ferrocenemethoxy, cobaltocenemethoxy, or nickelocenemethoxy;

aralkyloxy such as benzyloxy or phenethyloxy;

aryloxy such as phenoxy, tolyloxy, naphthoxy, xylyloxy, mesityloxy, chlorophenoxy, or methoxyphenoxy;

alkenyl such as vinyl, allyl, butenyl, butadienyl, pentenyl, cyclopentadienyl, or octenyl;

alkenyloxy such as vinyloxy, allyloxy, butenyloxy, butadienyloxy, pentenyloxy, cyclopentadienyloxy, or octenyloxy;

alkylthio such as methylthio, ethylthio, propylthio, butylthio, pentylthio, hexylthio, heptylthio, octylthio, decylthio, methoxymethylthio, ethoxyethylthio, ethoxyethylthio, or trifluoromethylthio;

aralkylthio such as benzylthio or phenethylthio;

arylthio such as phenylthio, tolylthio, naphthylthio, xylylthio, mesylthio, chlorophenylthio, or methoxyphenylthio;

dialkylamino such as dimethylamino, diethylamino, dipropylamino, or dibutylamino;

acyl such as acetyl, propionyl, butanoyl, ferrocenecarbonyl, cobaltocenecarbonyl, or nickelocenecarbonyl;

alkoxycarbonyl such as methoxycarbonyl, ethoxycarbonyl, ferrocenemethoxycarbonyl, 1-methylferrocen-1'-ylmethoxycarbonyl, cobaltocenylmethoxycarbonyl, or nickelocenylmethoxycarbonyl;

aralkyloxycarbonyl such as benzyloxycarbonyl or phenethyloxycarbonyl;

aryloxycarbonyl such as phenoxycarbonyl, tolyloxycarbonyl, naphthoxycarbonyl, xylyloxycarbonyl, mesyloxycarbonyl, chlorophenoxycarbonyl, or methoxyphenoxycarbonyl;

alkenyloxycarbonyl such as vinyloxycarbonyl, allyloxycarbonyl, butenyloxycarbonyl, butadienyloxycarbonyl, cyclopentadienyloxy, pentenyloxycarbonyl, or octenyloxycarbonyl;

alkylaminocarbonyl such as monoalkylaminocarbonyl having 2 to 10 carbon atoms such as methylaminocarbonyl, ethylaminocarbonyl, propylaminocarbonyl, butylaminocarbonyl, pentylaminocarbonyl, hexylaminocarbonyl, heptylaminocarbonyl, octylaminocarbonyl, nonylaminocarbonyl, 3,5,5-trimethylhexylaminocarbonyl, or 2-ethylhexylaminocarbonyl, and dialkylaminocarbonyl having 3 to 20 carbon atoms such as dimethylaminocarbonyl, diethylaminocarbonyl, dipropylaminocarbonyl, dibutylaminocarbonyl, dipentylaminocarbonyl, dihexylaminocarbonyl, diheptylaminocarbonyl, dioctylaminocarbonyl, piperidinocarbonyl, morpholinocarbonyl, 4-methylpiperazinocarbonyl, or 4-ethylpiperazinocarbonyl;

heterocycle such as furanyl, pyrrolyl, 3-pyrrolino, pyrrolidino, 1,3-oxolanyl, pyrazolyl, 2-pyrazolinyl, pyrazolidinyl, imidazolyl, oxazolyl, thiazolyl, 1,2,3-oxadiazolyl, 1,2,3-triazolyl, 1,2,4-triazolyl, 1,3,4-thiadiazolyl, 4H-pyranyl, pyridinyl, piperidinyl, dioxanyl, morpholinyl, pyridazinyl, pyrimidinyl, pyrazinyl, piperazinyl, triazinyl, benzofuranyl, indolyl, thionaphthenyl, benzimidazolyl, benzothiazolyl, purinyl, quinolinyl, isoquinolinyl, coumarinyl, cinnolinyl, quinoxalinyl, dibenzofuranyl, carbazolyl, phenanthrolinyl, phenothiazinyl, or flavonyl; and metallocenyl such as ferrocenyl, cobaltocenyl, nickelocenyl, ruthenocenyl, osmocenyl, or titanocenyl.

As examples of the substituted or unsubstituted heteroaryloxy group to substitute a ring AR, a heteroaryloxy group which may have an alkyl group as mentioned above as a substituent or heteroaryloxy group which may have the same substituent as the alkyl group as mentioned above may have, may be mentioned. Preferable examples include unsubstituted heteroaryloxy such as furanyloxy, pyrrolyloxy, 3-pyrrolinoxy, pyrazolyloxy, imidazolyloxy, oxazolyloxy, thiazolyloxy, 1,2,3-oxadiazolyloxy, 1,2,3-triazolyloxy, 1,2,4-triazolyloxy, 1,3,4-thiadiazolyloxy, pyridinyloxy, pyridazinyloxy, pyrimidinyloxy, pyrazinyloxy, piperazinyloxy, triazinyloxy, benzofuranyloxy, indolyloxy, thionaphthenyloxy, benzimidazolyloxy, benzothiazolyloxy, benzotriazol-2-yloxy, benzotriazol-1-yloxy, purinyloxy, quinolinyloxy, isoquinolinyloxy, coumarinyloxy, cinnolinyloxy, quinoxalinyloxy, dibenzofuranyloxy, carbazolyloxy, phenanthrolinyloxy, phenothiazinyloxy, flavonyloxy, phthalimidyloxy, or naphthylimidyloxy;

or heteroaryloxy substituted by following substituents:
halogen such as fluorine, chlorine, bromine, or iodide;
cyano;
alkyl such as methyl, ethyl, propyl, butyl, pentyl, hexyl, heptyl, octyl, decyl, methoxymethyl, ethoxyethyl, ethoxyethyl, or trifluoromethyl;
aralkyl such as benzyl or phenethyl;
aryl such as phenyl, tolyl, naphthyl, xylyl, mesyl, chlorophenyl, or methoxyphenyl;
alkoxy such as methoxy, ethoxy, propoxy, butoxy, pentoxy, hexyloxy, heptyloxy, octyloxy, nonyloxy, decyloxy, 2-ethylhexyloxy, 3,5,5-trimethylhexyloxy, ferrocenemethoxy, cobaltocenemethoxy, or nickelocenemethoxy;
aralkyloxy such as benzyloxy or phenethyloxy;
aryloxy such as phenoxy, tolyloxy, naphthoxy, xylyloxy, mesityloxy, chlorophenoxy, or methoxyphenoxy;
alkenyl such as vinyl, allyl, butenyl, butadienyl, pentenyl, cyclopentadienyl, or octenyl;
alkenyloxy such as vinyloxy, allyloxy, butenyloxy, butadienyloxy, pentenyloxy, cyclopentadienyloxy, or octenyloxy;

alkylthio such as methylthio, ethylthio, propylthio, butylthio, pentylthio, hexylthio, heptylthio, octylthio, decylthio, methoxymethylthio, ethoxyethylthio, ethoxyethylthio, or trifluoromethylthio;
aralkylthio such as benzylthio or phenethylthio;
arylthio such as phenylthio, tolylthio, naphthylthio, xylylthio, mesylthio, chlorophenylthio, or methoxyphenylthio;
dialkylamino such as dimethylamino, diethylamino, dipropylamino, or dibutylamino;
acyl such as acetyl, propionyl, butanoyl, ferrocenecarbonyl, cobaltocenecarbonyl, or nickelocenecarbonyl;
alkoxycarbonyl such as methoxycarbonyl, ethoxycarbonyl, ferrocenemethoxycarbonyl, 1-methylferrocen-1'-ylmethoxycarbonyl, cobaltocenylmethoxycarbonyl, or nickelocenylmethoxycarbonyl;
aralkyloxycarbonyl such as benzyloxycarbonyl or phenethyloxycarbonyl;
aryloxycarbonyl such as phenoxycarbonyl, tolyloxycarbonyl, naphthoxycarbonyl, xylyloxycarbonyl, mesyloxycarbonyl, chlorophenoxycarbonyl, or methoxyphenoxycarbonyl;
alkenyloxycarbonyl such as vinyloxycarbonyl, allyloxycarbonyl, butenyloxycarbonyl, butadienyloxycarbonyl, cyclopentadienyloxy, pentenyloxycarbonyl, or octenyloxycarbonyl;
alkylaminocarbonyl such as monoalkylaminocarbonyl having 2 to 10 carbon atoms such as methylaminocarbonyl, ethylaminocarbonyl, propylaminocarbonyl, butylaminocarbonyl, pentylaminocarbonyl, hexylaminocarbonyl, heptylaminocarbonyl, octylaminocarbonyl, nonylaminocarbonyl, 3,5,5-trimethylhexylaminocarbonyl, or 2-ethylhexylaminocarbonyl, and dialkylaminocarbonyl having 3 to 20 carbon atoms such as dimethylaminocarbonyl, diethylaminocarbonyl, dipropylaminocarbonyl, dibutylaminocarbonyl, dipentylaminocarbonyl, dihexylaminocarbonyl, diheptylaminocarbonyl, dioctylaminocarbonyl, piperidinocarbonyl, morpholinocarbonyl, 4-methylpiperazinocarbonyl, or 4-ethylpiperazinocarbonyl;

heterocycle such as furanyl, pyrrolyl, 3-pyrrolino, pyrrolidino, 1,3-oxolanyl, pyrazolyl, 2-pyrazolinyl, pyrazolidinyl, imidazolyl, oxazolyl, thiazolyl, 1,2,3-oxadiazolyl, 1,2,3-triazolyl, 1,2,4-triazolyl, 1,3,4-thiadiazolyl, 4H-pyranyl, pyridinyl, piperidinyl, dioxanyl, morpholinyl, pyridazinyl, pyrimidinyl, pyrazinyl, piperazinyl, triazinyl, benzofuranyl, indolyl, thionaphthenyl, benzimidazolyl, benzothiazolyl, purinyl, quinolinyl, isoquinolinyl, coumarinyl, cinnolinyl, quinoxalinyl, dibenzofuranyl, carbazolyl, phenanthrolinyl, phenothiazinyl, or flavonyl; and metallocenyl such as ferrocenyl, cobaltocenyl, nickelocenyl, ruthenocenyl, osmocenyl, or titanocenyl.

As examples of the substituted or unsubstituted heteroaryloxycarbonyl group to substitute a ring AR, a heteroaryloxycarbonyl group which may have an alkyl group as mentioned above as a substituent or a heteroaryloxycarbonyl group which may have the same substituent as the alkyl group as mentioned above may have, may be mentioned. Preferable examples include unsubstituted heteroaryloxycarbonyl such as furanyloxycarbonyl, pyrrolyloxycarbonyl, 3-pyrrolinoxycarbonyl, pyrazolyloxycarbonyl, imidazolyloxycarbonyl, oxazolyloxycarbonyl, thiazolyloxycarbonyl, 1,2,3-oxadiazolyloxycarbonyl, 1,2,3-triazolyloxycarbonyl, 1,2,4-triazolyloxycarbonyl, 1,3,4-thiadiazolyloxycarbonyl, pyridinyloxycarbonyl, pyridazinyloxycarbonyl, pyrimidinyloxycarbonyl, pyrazinyloxycarbonyl, piperazinyloxycarbonyl, triazinyloxycarbonyl, benzofuranyloxycarbonyl, indolyloxycarbonyl, thionaphthenyloxycarbonyl, benzimidazolyloxycarbonyl, benzothiazolyloxycarbonyl, benzotriazol-2-yloxycarbonyl, benzotriazol-1-yloxycarbonyl, purinyloxycarbonyl, quinolinyloxycarbonyl, isoquinolinyloxycarbonyl, coumarinyloxycarbonyl, cinnolinyloxycarbonyl, quinoxalinyloxycarbonyl, dibenzofuranyloxycarbonyl, carbazolyloxycarbonyl, phenanthrolinyloxycarbonyl, phenothiazinyloxycarbonyl, flavonyloxycarbonyl, phthalimidyloxycarbonyl, or naphthylimidyloxycarbonyl;

or heteroaryloxycarbonyl substituted by following substituents:

halogen such as fluorine, chlorine, bromine, or iodide;

cyano;

alkyl such as methyl, ethyl, propyl, butyl, pentyl, hexyl, heptyl, octyl, decyl, methoxymethyl, ethoxyethyl, ethoxyethyl, or trifluoromethyl;

aralkyl such as benzyl or phenethyl;

aryl such as phenyl, tolyl, naphthyl, xylyl, mesyl, chlorophenyl, or methoxyphenyl;

alkoxy such as methoxy, ethoxy, propoxy, butoxy, pentoxy, hexyloxy, heptyloxy, octyloxy, nonyloxy, decyloxy, 2-ethylhexyloxy, 3,5,5-trimethylhexyloxy, ferrocenemethoxy, cobaltocenemethoxy, or nickelocenemethoxy;

aralkyloxy such as benzyloxy or phenethyloxy;

aryloxy such as phenoxy, tolyloxy, naphthoxy, xylyloxy, mesityloxy, chlorophenoxy, or methoxyphenoxy;

alkenyl such as vinyl, allyl, butenyl, butadienyl, pentenyl, cyclopentadienyl, or octenyl;

alkenyloxy such as vinyloxy, allyloxy, butenyloxy, butadienyloxy, pentenyloxy, cyclopentadienyloxy, or octenyloxy;

alkylthio such as methylthio, ethylthio, propylthio, butylthio, pentylthio, hexylthio, heptylthio, octylthio, decylthio, methoxymethylthio, ethoxyethylthio, ethoxyethylthio, or trifluoromethylthio;

aralkylthio such as benzylthio or phenethylthio;

arylthio such as phenylthio, tolylthio, naphthylthio, xylylthio, mesylthio, chlorophenylthio, or methoxyphenylthio;

dialkylamino such as dimethylamino, diethylamino, dipropylamino, or dibutylamino;

acyl such as acetyl, propionyl, butanoyl, ferrocenecarbonyl, cobaltocenecarbonyl, or nickelocenecarbonyl;

alkoxycarbonyl such as methoxycarbonyl, ethoxycarbonyl, ferrocenemethoxycarbonyl, 1-methylferrocen-1'-ylmethoxycarbonyl, cobaltocenylmethoxycarbonyl, or nickelocenylmethoxycarbonyl;

aralkyloxycarbonyl such as benzyloxycarbonyl or phenethyloxycarbonyl;

aryloxycarbonyl such as phenoxycarbonyl, tolyloxycarbonyl, naphthoxycarbonyl, xylyloxycarbonyl, mesyloxycarbonyl, chlorophenoxycarbonyl, or methoxyphenoxycarbonyl;

alkenyloxycarbonyl such as vinyloxycarbonyl, allyloxycarbonyl, butenyloxycarbonyl, butadienyloxycarbonyl, cyclopentadienyloxy, pentenyloxycarbonyl, or octenyloxycarbonyl;

alkylaminocarbonyl such as monoalkylaminocarbonyl having 2 to 10 carbon atoms such as methylaminocarbonyl, ethylaminocarbonyl, propylaminocarbonyl, butylaminocarbonyl, pentylaminocarbonyl, hexylaminocarbonyl, heptylaminocarbonyl, octylaminocarbonyl, nonylaminocarbonyl, 3,5,5-trimethylhexylaminocarbonyl, or 2-ethylhexylaminocarbonyl, and dialkylaminocarbonyl having 3 to 20 carbon atoms such as dimethylaminocarbonyl, diethylaminocarbonyl, dipropylaminocarbonyl, dibutylaminocarbonyl, dipentylaminocarbonyl, dihexylaminocarbonyl, diheptylaminocarbonyl, dioctylaminocarbonyl, piperidinocarbonyl, morpholinocarbonyl, 4-methylpiperazinocarbonyl, or 4-ethylpiperazinocarbonyl;

heterocycle such as furanyl, pyrrolyl, 3-pyrrolino, pyrrolidino, 1,3-oxolanyl, pyrazolyl, 2-pyrazolinyl, pyrazolidinyl, imidazolyl, oxazolyl, thiazolyl, 1,2,3-oxadiazolyl, 1,2,3-triazolyl, 1,2,4-triazolyl, 1,3,4-thiadiazolyl, 4H-pyranyl, pyridinyl, piperidinyl, dioxanyl, morpholinyl, pyridazinyl, pyrimidinyl, pyrazinyl, piperazinyl, triazinyl, benzofuranyl, indolyl, thionaphthenyl, benzimidazolyl, benzothiazolyl, purinyl, quinolinyl, isoquinolinyl, coumarinyl, cinnolinyl, quinoxalinyl, dibenzofuranyl, carbazolyl, phenanthrolinyl, phenothiazinyl, or flavonyl; and metallocenyl such as ferrocenyl, cobaltocenyl, nickelocenyl, ruthenocenyl, osmocenyl, or titanocenyl.

As examples of the substituted or unsubstituted heteroarylthio group to substitute a ring AR, a heteroarylthio group which may have an alkyl group as mentioned above as a substituent or a heteroarylthio group which may have the same substituent as the alkyl group as mentioned above may have, may be mentioned. Preferable examples include unsubstituted heteroarylthio such as furanylthio, pyrrolylthio, 3-pyrrolinothio, pyrazolylthio, imidazolylthio, oxazolylthio, thiazolylthio, 1,2,3-oxadiazolylthio, 1,2,3-triazolylthio, 1,2,4-triazolylthio, 1,3,4-thiadiazolylthio, pyridinylthio, pyridazinylthio, pyrimidinylthio, pyrazinylthio, piperazinylthio, triazinylthio, benzofuranylthio, indolylthio, thionaphthenylthio, benzimidazolylthio, benzothiazolylthio, benzotriazol-2-ylthio, benzotriazol-1-ylthio, purinylthio, quinolinylthio, isoquinolinylthio, coumarinylthio, cinnolinylthio, quinoxalinylthio, dibenzofuranylthio, carbazolylthio, phenanthrolinylthio, phenothiazinylthio, flavonylthio, phthalimidylthio, or naphthylimidylthio;

or heteroarylthio substituted by following substituents:

halogen such as fluorine, chlorine, bromine, or iodide;

cyano;

alkyl such as methyl, ethyl, propyl, butyl, pentyl, hexyl, heptyl, octyl, decyl, methoxymethyl, ethoxyethyl, ethoxyethyl, trifluoromethyl;

aralkyl such as benzyl or phenethyl;

aryl such as phenyl, tolyl, naphthyl, xylyl, mesyl, chlorophenyl, or methoxyphenyl;

alkoxy such as methoxy, ethoxy, propoxy, butoxy, pentoxy, hexyloxy, heptyloxy, octyloxy, nonyloxy, decyloxy, 2-ethylhexyloxy, 3,5,5-trimethylhexyloxy, ferrocenemethoxy, cobaltocenemethoxy, or nickelocenemethoxy;

aralkyloxy such as benzyloxy or phenethyloxy;

aryloxy such as phenoxy, tolyloxy, naphthoxy, xylyloxy, mesityloxy, chlorophenoxy, or methoxyphenoxy;

alkenyl such as vinyl, allyl, butenyl, butadienyl, pentenyl, cyclopentadienyl, or octenyl;

alkenyloxy such as vinyloxy, allyloxy, butenyloxy, butadienyloxy, pentenyloxy, cyclopentadienyloxy, or octenyloxy;

alkylthio such as methylthio, ethylthio, propylthio, butylthio, pentylthio, hexylthio, heptylthio, octylthio, decylthio, methoxymethylthio, ethoxyethylthio, ethoxyethylthio, or trifluoromethylthio;

aralkylthio such as benzylthio or phenethylthio;

arylthio such as phenylthio, tolylthio, naphthylthio, xylylthio, mesylthio, chlorophenylthio, or methoxyphenylthio;

dialkylamino such as dimethylamino, diethylamino, dipropylamino, or dibutylamino;

acyl such as acetyl, propionyl, butanoyl, ferrocenecarbonyl, cobaltocenecarbonyl, or nickelocenecarbonyl;

alkoxycarbonyl such as methoxycarbonyl, ethoxycarbonyl, ferrocenemethoxycarbonyl, 1-methylferrocen-1'-yl-methoxycarbonyl, cobaltocenylmethoxycarbonyl, or nickelocenylmethoxycarbonyl;

aralkyloxycarbonyl such as benzyloxycarbonyl or phenethyloxycarbonyl;

aryloxycarbonyl such as phenoxycarbonyl, tolyloxycarbonyl, naphthoxycarbonyl, xylyloxycarbonyl, mesyloxycarbonyl, chlorophenoxycarbonyl, or methoxyphenoxycarbonyl;

alkenyloxycarbonyl such as vinyloxycarbonyl, allyloxycarbonyl, butenyloxycarbonyl, butadienyloxycarbonyl, cyclopentadienyloxy, pentenyloxycarbonyl, or octenyloxycarbonyl;

alkylaminocarbonyl such as monoalkylaminocarbonyl having 2 to 10 carbon atoms such as methylaminocarbonyl, ethylaminocarbonyl, propylaminocarbonyl, butylaminocarbonyl, pentylaminocarbonyl, hexylaminocarbonyl, heptylaminocarbonyl, octylaminocarbonyl, nonylaminocarbonyl, 3,5,5-trimethylhexylaminocarbonyl, or 2-ethylhexylaminocarbonyl, and dialkylaminocarbonyl having 3 to 20 carbon atoms such as dimethylaminocarbonyl, diethylaminocarbonyl, dipropylaminocarbonyl, dibutylaminocarbonyl, dipentylaminocarbonyl, dihexylaminocarbonyl, diheptylaminocarbonyl, dioctylaminocarbonyl, piperidinocarbonyl, morpholinocarbonyl, 4-methylpiperazinocarbonyl, or 4-ethylpiperazinocarbonyl;

heterocycle such as furanyl, pyrrolyl, 3-pyrrolino, pyrrolidino, 1,3-oxolanyl, pyrazolyl, 2-pyrazolinyl, pyrazolidinyl, imidazolyl, oxazolyl, thiazolyl, 1,2,3-oxadiazolyl, 1,2,3-triazolyl, 1,2,4-triazolyl, 1,3,4-thiadiazolyl, 4H-pyranyl, pyridinyl, piperidinyl, dioxanyl, morpholinyl, pyridazinyl, pyrimidinyl, pyrazinyl, piperazinyl, triazinyl, benzofuranyl, indolyl, thionaphthenyl, benzimidazolyl, benzothiazolyl, purinyl, quinolinyl, isoquinolinyl, coumarinyl, cinnolinyl, quinoxalinyl, dibenzofuranyl, carbazolyl, phenanthrolinyl, phenothiazinyl, or flavonyl;

metallocenyl such as ferrocenyl, cobaltocenyl, nickelocenyl, ruthenocenyl, osmocenyl, or titanocenyl.

As examples of the substituted or unsubstituted metallocenyl group to substitute a ring AR, a metallocenyl group which may have an alkyl group as mentioned above as a substituent, a metallocenyl group which may have the same substituent as the alkyl group as mentioned above may have, or a metallocenyl group having a phosphino group having a substituent, may be mentioned. Specific examples include metallocenyl groups represented by a formula (12) below:

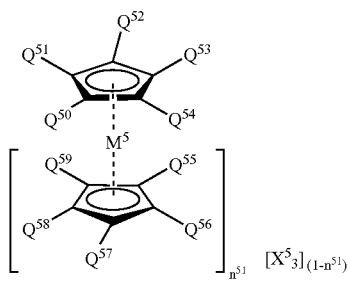

(12)

wherein $M^5$ represents a monovalent or bivalent transition metal atom; $Q^{50}$ to $Q^{59}$ each represent independently a single bond, a halogen atom, substituted or unsubstituted alkyl, substituted or unsubstituted aralkyl, substituted or unsubstituted aromatic ring, substituted or unsubstituted alkenyl, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted amino, or phosphino having a substituent; or, two or more substituents selected from $Q^{50}$ to $Q^{59}$ each may independently be bonded via a linking group to form a cyclic structure together with carbon atoms to which they are attached; $X^5$ represents a halogen atom or CO; $n^{51}$ represents 0 or 1, with the proviso that at least one of $Q^{50}$ to $Q^{59}$ is a single bond.

A monovalent or bivalent transition metal represented by $M^5$ is not particularly restricted as long as it is a metal constituting metallocene, but preferably includes Fe, Co, Ni, Ru, Rh, Pd, Ir, Pt, Os, Mn Cr, W, V, Sc, Y, La, Ce, Pr, Nd, Sm, Gd, Er, Tm and Yb; more preferably metal atoms of group VIII, and most preferably, Fe.

Specific examples represented by $Q^{50}$ to $Q^{59}$, of halogen, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted amino, substituted or unsubstituted alkenyl, are the same groups as those mentioned above which may substitute AR.

The phosphino group having a substituent represented by $Q^{50}$ to $Q^{59}$ is a phosphino group which may have an alkyl group as mentioned above as a substituent or a phosphino group which may have the same substituent as the alkyl group as mentioned above may have. Specific examples include dialkylphosphino groups such as dimethylphosphino, diethylphosphino, dipropylphosphino, dibutylphosphino, dipentylphosphino, and dihexylphosphino; alkylarylphosphino groups such as P-methyl-P-phenylphosphino; and diarylphosphino groups such as diphenylphosphino, and phenyl-3,5-xylylphosphino.

Examples of a halogen atom represented by $X^5$ include fluorine, chlorine, bromine and iodine.

Furthermore, two or more substituents selected from the substituents on a ring AR each independently may bond to each other via a linking group (referred to as "T") to form a cyclic structure with each atom at the position substituted by each substituent. Specific examples of the cyclic structure thus formed include carbocyclic aliphatic, heterocyclic aliphatic, carbocyclic aromatic and heterocyclic aromatic rings, and a planar or cubic cyclic structure desirably formed by appropriately combining these.

Examples of the residue formed by combining two or more aromatic ring residues represented by ring AR via one or more linking groups T include a residue formed by selecting two or more aromatic rings from substituted or unsubstituted carbocyclic aromatic ring or substituted or unsubstituted heterocyclic aromatic ring and combining them via one or more linking groups.

Examples of the linking group T for combining two or more aromatic rings include a single bond or a group formed by appropriately combining elements selected from carbon atom, hetero atoms such as nitrogen, oxygen, sulfur, phosphorus, a metal atom and a semimetal atom, and hydrogen atom. Preferably, examples of the linking group include bi- to decavalent linking groups formed by combining one or more linking groups selected from bivalent linking groups such as —O—, —S—, —C(=O)—, —C(=S)—, —S(=O)—, —SO$_2$—, —C(R$^{L1}$)(R$^{L2}$)—, —C(R$^{L1}$)=C(R$^{L2}$)—, —C≡C—, —N=C(R$^{L1}$)—, —N(R$^{L1}$)— where R$^{L1}$ and R$^{L2}$ represent hydrogen, substituted or unsubstituted alkyl, substituted or unsubstituted aralkyl, or substituted or unsubstituted aryl, a substituted or unsubstituted bivalent aliphatic hydrocarbon group and substituted or unsubstituted bivalent aromatic ring;

trivalent linking groups such as a nitrilo group, boron atom, and phosphorus atom;

tetravalent linking groups such as a spiro carbon atom, and spiro silicon atom;

bi- to octavalent metal atoms such as a representative metal atom and transition metal atom; and bi- to decavalent linking groups such as a bi- to decavalent substituted or unsubstituted metallocene residue.

Examples of the substituted or unsubstituted bivalent aliphatic hydrocarbon group preferably include linear, branched, or cyclic bivalent saturated aliphatic hydrocarbon or unsaturated aliphatic hydrocarbon having 1 to 20 carbon atoms. They may have, between C—C bond in a substituent substituting to the bivalent aliphatic hydrocarbon group, an oxygen atom, a sulfur atom that may have oxygen atom, a substituted or unsubstituted imino group, a carbonyl group, a thiacarbonyl group, and a metal atom. Preferable examples of bivalent aliphatic hydrocarbon groups include substituted or unsubstituted alkylene having 1 to 16 carbon atoms such as methylene, ethylene, 1,2-dichloroethylene, trimethylene, tetramethylene, pentamethylene, cyclopentylene, hexamethylene, cyclohexylene, heptamethylene, octamethylene, nonamethylene, decamethylene, undecamethylene, dodecamethylene, tridecamethylene, tetradecamethylene, and pentadecamethylene; substituted or unsubstituted alkenylene groups having 2 to 10 carbon atoms such as vinylene, 1,2-dichlorovinylene, propenylene, 1-butenylene, 1-pentenylene, 2-pentenylene, and decanylene; and substituted or unsubstituted alkynylene groups having 2 to 12 carbon atoms such as ethynylene, propynylene, 1,3-butadiynylene, 1,2-bisethyleneoxycarbonylethyne, 1,2-bispropyleneoxycarbonylethyne, and 1,2-bisbutyleneoxycarbonylethyne.

Examples of a ring constituting a substituted or unsubstituted bivalent aromatic ring group include substituted or unsubstituted carbocyclic aromatic rings and heterocyclic aromatic rings as mentioned above. Preferable examples of the substituted or unsubstituted bivalent aromatic ring group include bivalent aromatic hydrocarbon such as phenylene, naphthylene, indenylene, anthracenylene, fluorenylene, azulenylene, naphthacenylene, chrysenylene, pyrenylene, or perylenylene;

bivalent heterocycle such as furanylene, pyrrolylene, 3-pyrrolynylene, pyrrolidinylene, 1,3-oxolanylene, pyrazolylene, 2-pyrazolinylene, pyrazolidinylene, imidazolylene, oxazolylene, thiazolylene, 1,2,3-oxadiazolylene, 1,2,3-triazolylene, 1,2,4-triazolylene, 1,3,4-thiadiazolylene, 4H-pyranylene, pyridinylene, piperidinylene, dioxanylene, morpholinylene, pyridazinylene, pyrimidinylene, pyrazinylene, piperazinylene, triazinylene, benzofuranylene, indolylene, thionaphthenylene, benzimidazolylene, benzothiazolylene, purinylene, quinolinylene, isoquinolylene, coumarinylene, cinnolinylene, quinoxalinylene, dibenzofuranylene, carbazolylene, phenanthronylene, phenothiadinylene, flavonylene, or perimidylene;

bivalent metallocenylene such as ferrocenylene, cobaltocenylene, nickelocenylene, dichlorotitanocenylene, trichlorotitanium cyclopentadienylene, bis(trifluoromethanesulfonato)titanocenylene, dichlorozirconocenylene, dimethylzirconocenylene, diethoxyzirconocenylene, bis(cyclopentadienylene)chromium, bis(cyclopentadienylene)dichloromolybdenum, bis(cyclopentadienylene)dichlorohafnium, bis(cyclopentadienylene)dichloroniobium, bis(cyclopentadienylene)ruthenium, bis(cyclopentadienylene)vanadium, bis(cyclopentadienylene)dichlorovanadium, octamethylferrocenylene, octamethylcobaltocenylene, or octamethylnickelocenylene.

Examples of bi- to octavalent metal atoms include representative metal atoms of IIA to VIA, IB and IIB groups in the periodic table and transition metal atoms having from 2 to 8 valences of IIIA to VIII groups in the periodic table. Preferable examples include Be, Mg, Ca, Sr, Ba, Ra, Al, Ga, In, Tl, Ge, Sn, Pb, Sb, Bi, Po, Sc, Y, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd, Hg, La, Ce, Pr, Nd, Pm, Sm, Eu, Gd, Tb, Dy, Ho, Er, Tm, Yb, Lu, Ac, Th, Pa, U, Np, Pu, Am, Cm, Bk, Cf, Es, Fm, Md, No, and Lr.

Examples of a substituted or unsubstituted metallocene residue having 2 to 10 valences are metallocene residues represented by the following general formula (13):

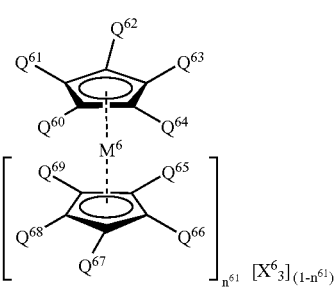

(13)

wherein $M^6$ represents a monovalent or bivalent transition metal atom; $Q^{60}$ to $Q^{69}$ each represent independently a single bond, a halogen atom, substituted or unsubstituted alkyl, substituted or unsubstituted aralkyl, substituted or unsubstituted aromatic ring, substituted or unsubstituted alkenyl, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted amino or, phosphino having a substituent; $X^6$ represents a halogen atom or CO; $n^6$ represents 0 or 1, with the proviso that at least two or more of $Q^{60}$ to $Q^{69}$ are single bonds.

Specific examples of a monovalent or bivalent transition metal atom represented by $M^6$ are the same as those represented by $M^5$ of the formula (12) mentioned above.

Specific examples represented by $Q^{60}$ to $Q^{69}$, of a halogen atom, substituted or unsubstituted alkyl, substituted or unsubstituted aralkyl, substituted or unsubstituted aromatic ring, substituted or unsubstituted alkenyl, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted amino, or phosphino group having a substituent, are those represented by $Q^{50}$ to $Q^{59}$ of the formula (12) mentioned above.

Specific examples of a halogen atom represented by $X^6$ are those represented by $X^5$ of the formula (12) mentioned above.

Preferable examples of linkage mediated by the linking group T include those represented by formula (15) and/or formula (16):

$$R^{r1}-T^1-R^{r2} \quad (15)$$

(16)

wherein $R^{r1}$ to $R^{r2}$ and $R^{r3}$ to $R^{r5}$ each independently represent either an substituent on the ring AR or an aromatic cyclic residue constituting a ring AR; $T^1$ is a bivalent linking group; and $T^2$ is a trivalent linking group.

Specific examples of a linking group represented by $T^1$ preferably include a group represented by any one of the following formulas (17):

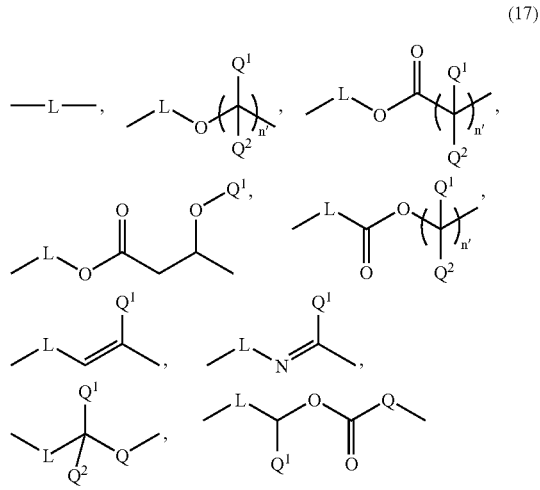
(17)

wherein L is a single bond, substituted or unsubstituted bivalent aliphatic hydrocarbon, substituted or unsubstituted bivalent aromatic ring, or —C(-Q)=N—; $Q^1$ and $Q^2$ each independently represent a hydrogen or halogen atom; a group selected from nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, or substituted or unsubstituted amino; $Q^3$ denotes a group represented by any one of —O-$Q^5$-, —C(=O)—O-$Q^5$-, and —O—C(=O)-$Q^5$-; $Q^5$ is a single bond, substituted or unsubstituted bivalent aliphatic hydrocarbon, or substituted or unsubstituted bivalent aromatic ring; $Q^4$ is represented by any one of —$CQ_2$-, —$CQ_2CQ_2$-, —CQ=CQ-, —$CQ_2$-C(=O)—, —$CQ_2CQ_2$-C(=O)—, where Q is the same as that mentioned above; and n is an integer of 0 to 4.

In the formula, examples of a linking group of substituted or unsubstituted bivalent aliphatic hydrocarbon group or substituted or unsubstituted bivalent aromatic ring group represented by L and $Q^5$ include the same groups as those mentioned in AR of the formula (1).

In the formula, with respect to —C(-Q)=N— represented by L, specific examples of substituent Q include halogen, nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, or substituted or unsubstituted amino as mentioned above.

Specific examples represented by $Q^1$ and $Q^2$, of the substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, and substituted or unsubstituted amino include the aforementioned substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, and substituted or unsubstituted amino; and $Q^1$ and $Q^2$ are preferably a hydrogen atom, and alkyl groups having from 1 to 4 carbon atoms such as methyl, ethyl, propyl, and butyl.

Specific examples of a linking group represented by $T^1$ include a group represented by the following formula (18) or (19):

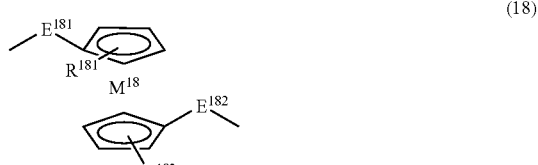
(18)

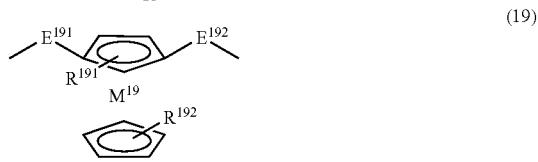
(19)

wherein $E^{181}$, $E^{182}$, $E^{191}$ and $E^{192}$ represent linking groups; $R^{181}$, $R^{182}$, $R^{191}$, and $R^{192}$ each independently represent a hydrogen or halogen atom, substituted or unsubstituted alkyl, substituted or unsubstituted alkoxy, or substituted phosphino; and $M^{18}$ and $M^{19}$ represent a bivalent transition metal atom.

In the general formulas (18) and (19), specific examples of linking groups represented by $E^{181}$, $E^{182}$, $E^{191}$ and $E^{192}$ include those represented by the formulas (17) mentioned above.

Specific examples of a halogen atom, substituted or unsubstituted alkyl, substituted or unsubstituted alkoxy, and substituted phosphino represented by $R^{181}$ $R^{182}$ $R^{191}$, and $R^{192}$ include the same halogen atom, substituted or unsubstituted alkyl, and substituted or unsubstituted alkoxy as mentioned above.

Specific examples of bivalent transition metal atoms represented by $M^{18}$ and $M^{19}$ include the same metal atoms as those represented by $M^5$ of the formula (12).

Specific examples of a linking group represented by $T^2$ preferably include groups represented by the following formula (20) or (21):

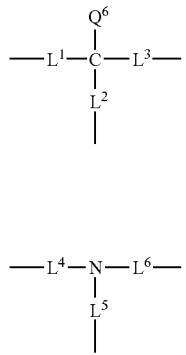

(20)

(21)

wherein $L^1$ to $L^6$ each independently represent a linking group; $Q^6$ represents a hydrogen or halogen atom; a group selected from nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, and substituted or unsubstituted amino.

Specific examples of a linking group represented by $L^1$ to $L^6$ include groups represented by formulas (17) mentioned above.

Specific examples represented by $Q^6$, of a halogen atom, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, and substituted or unsubstituted amino include the same halogen atom, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, and substituted or unsubstituted amino as mentioned above.

In the formula (1), n representing the number of imide groups binding to ring AR denotes generally from 1 to 10, preferably from 1 to 3, and more preferably from 1 to 2.

Specific examples of $A^1$ to $A^n$ represented by $A^m$ include the same halogen atom, nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, and substituted or unsubstituted metallocenyl as those substituting for a ring AR.

Specific examples of substituted or unsubstituted metallocene residue contained in at least one of substituents $A^1$ to $A^n$ include metallocene residues represented by a general formula (14):

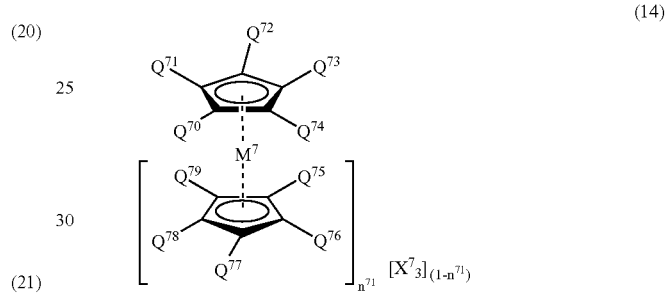

(14)

wherein $M^7$ represents monovalent to bivalent transition metal atom; $Q^{70}$ to $Q^{79}$ each independently represent a single bond, a halogen atom, substituted or unsubstituted alkyl, substituted or unsubstituted aralkyl, substituted or unsubstituted aromatic ring, substituted or unsubstituted alkenyl, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted amino, or phosphino having a substituent; $X^7$ represents a halogen atom or CO; $n^7$ represents 0 or 1, with the proviso that at least one of $Q^{70}$ to $Q^{79}$ is a single bond.

Specific examples of a monovalent and bivalent transition metal atoms represented by $M^7$ are the same metal atoms as the transition metals represented by $M^5$ of the formula (12) mentioned above.

Specific examples represented by $Q^{70}$ to $Q^{79}$, of a halogen atom, substituted or unsubstituted alkyl, substituted or unsubstituted aralkyl, substituted or unsubstituted aromatic ring, substituted or unsubstituted alkenyl, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted amino, and phosphino group having a substituent represented by $Q^{70}$ to $Q^{79}$ are the same as of the formula (12) mentioned above.

Specific examples of a monovalent and bivalent transition metal atom represented by $X^7$ are the same halogen atoms represented by $X^5$ of the formula (12) mentioned above.

Note that at least one substituent selected from the substituents $A^1$ to $A^n$ is preferably a group formed by bonding a substituted or unsubstituted metallocene group represented by the formula (14) mentioned above to a nitrogen atom of an imide group via a bivalent linking group composed of at least one selected from the substituted or unsubstituted bivalent aliphatic hydrocarbon or substituted or unsubstituted bivalent aromatic ring groups; and more preferably, at least one substituent selected from the substituents $A^1$ to $A^n$ is preferably a group formed by bonding a substituted or unsubstituted metallocene group to a nitrogen atom of an imide group via a substituted or unsubstituted bivalent aromatic ring group.

A preferable form of an imide compound according to the present invention includes a compound represented by the following general formula (2):

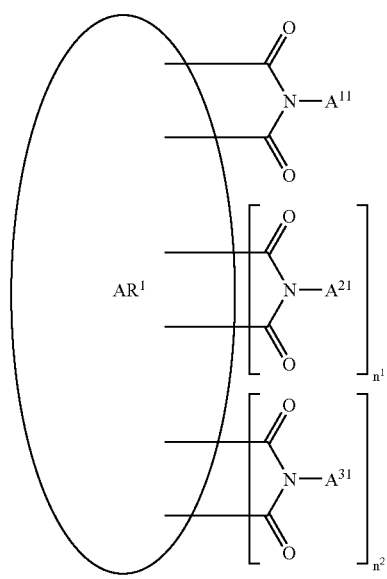

(2)

wherein a ring $AR^1$ represents an aromatic ring residue or a residue formed by combining two or more aromatic ring residues via one or more one linking groups; $n^1$ and $n^2$ each independently represent 0 or 1; $A^{11}$, $A^{21}$ and $A^{31}$ each represent a substituent bonded to a nitrogen atom of an imide group, with the proviso that at least one substituent selected from the group consisting of $A^{11}$, $A^{21}$ and $A^{31}$ is one having one or more substituted or unsubstituted metallocene residue.

Specific examples of an aromatic ring residue represented by ring $AR^1$ are the same groups as the aforementioned aromatic ring residues represented by ring AR of the formula (1).

Specific examples of linking groups in the residue formed by combining two or more aromatic ring residues via one or more linking groups are the same groups as linking group T of the formula (1).

In the formula, preferable examples of $n^1$ and $n^2$ include a combination of $n^1=1$ and $n^2=0$ and a combination of $n^1=0$ and $n^2=1$.

Specific examples of substituents each bonded to an imide group and represented by $A^{11}$, $A^{21}$ or $A^{31}$ are the same groups as substituents represented by $A^m$ in the formula (1).

A preferable form of an imide compound according to the present invention includes a compound represented by the following general formula (3):

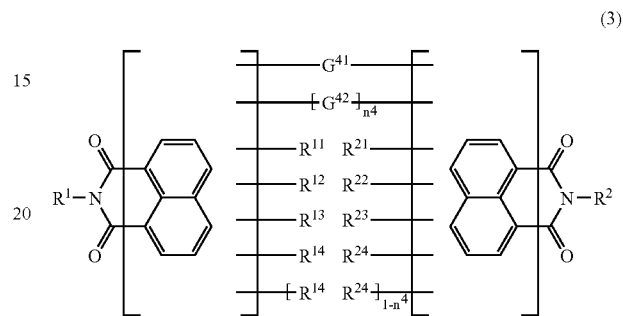

(3)

wherein $R^1$, $R^2$, $R^{11}$ to $R^{15}$, and $R^{21}$ to $R^{25}$ each independently represent a hydrogen or halogen atom; a group selected from nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, substituted or unsubstituted heteroarylthio, or substituted or unsubstituted metallocenyl; or, in a combination of $R^{11}$ to $R^{15}$ and/or a combination of $R^{21}$ to $R^{25}$, two or more substituents selected from each of the combinations may independently combine via a linking group within the same combination to form a cyclic structure together with carbon atoms to which they are attached; $G^{41}$ and $G^{42}$ represent a bivalent linking group selected from a single bond, substituted or unsubstituted bivalent aliphatic hydrocarbon, or substituted or unsubstituted bivalent aromatic ring; $n^4$ represents 0 or 1, with the proviso that at least one of $R^1$ and $R^2$ represents a group in which a substituted or unsubstituted metallocene residue bonds to the nitrogen atom of the imide group via a bivalent linking group composed of at least one selected from a substituted or unsubstituted bivalent aliphatic hydrocarbon group and substituted or unsubstituted bivalent aromatic ring group.

Specific examples represented by $R^1$, $R^2$, $R^{11}$ to $R^{15}$, and $R^{21}$ to $R^{25}$, of halogen, nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, substituted or unsubstituted heteroarylthio, and substituted or unsubstituted metallocenyl are the same groups as the substituents substituting a ring AR of the formula (1) mentioned above.

Specific examples of the linking group where, in the combinations of $R^{11}$ to $R^{15}$ and/or $R^{21}$ to $R^{25}$, two or more substituents selected from each of the combinations each independently combine via a linking group within the same combination to form a cyclic structure together with carbon atoms to which they are attached, are the same linking groups as those of $T^1$ of the formula (15) and $T^2$ of the formula (16).

Furthermore, in bivalent linking groups represented by $G^{41}$ and $G^{42}$, examples of the substituted or unsubstituted bivalent aliphatic hydrocarbon, and substituted or unsubstituted bivalent aromatic ring are the same linking groups as those of $T^1$ of the formula (15).

Preferable examples of the bivalent linking groups represented by $G^{41}$ and $G^{42}$ include a single bond, ethynylene, 1,4-phenylene, 1,3-phenylene, 5-bromo-1,3-phenylene, 1,4-(2,3,5,6-tetramethyl)phenylene, 4,4'-biphenylene, and 1,4-naphthylene. Furthermore, these groups may be appropriately combined to form a new bivalent linking.

Examples of alkyl, aralkyl or aromatic ring substituted by a substituted or unsubstituted metallocene residue of $R^1$ and $R^2$ include the aforementioned substituted or unsubstituted alkyl, substituted or unsubstituted aralkyl, and substituted or unsubstituted aromatic ring substituted by generally 1 to 10, preferably 1 to 5 metallocene groups of the formula (14). Furthermore, preferable examples of $R^1$ and $R^2$ include the aforementioned substituted or unsubstituted aromatic ring substituted by 1 to 3 metallocene groups of the formula (14).

Specifically preferable examples of $R^1$ and $R^2$ include aryl substituted by a ferrocenylphenyl such as 2-ferrocenylphenyl, 3-ferrocenylphenyl, 4-ferrocenylphenyl, 2,4-diferrocenylphenyl, 3,5-diferrocenylphenyl, 2,6-diferrocenylphenyl, 2,4,6-triferrocenylphenyl, 2-(3-ferrocenyl)ferrocenylphenyl, 3-(3-ferrocenyl) ferrocenylphenyl, and 4-(3-ferrocenyl) ferrocenylphenyl; or aryl substituted by a ferrocenyl group and bonded by an alkyl such as methyl, ethyl, n-propyl, isopropyl, and 2,4-dimethyl-3-pentyl; an alkoxy group such as methoxy, ethoxy, n-propoxy, isopropoxy, and 2,4-dimethyl-3-pentyloxy group; or an aryloxy group such as 9,9-dimethylfluoreneoxy group.

Particularly, a phenyl group having a metallocenyl group, such as a ferrocenyl group bonded to at least the positions 2 and/or 4, is preferable since it has an excellent stability to regeneration light. Particularly, the phenyl group having a metallocenyl group, such as a ferrocenyl group bonded to the position 2, is more preferable since it can provide a stable dye film and excellent in heat and moisture resistance.

Furthermore, a preferable form of an imide compound according to the present invention include a compound represented by the following general formula (4):

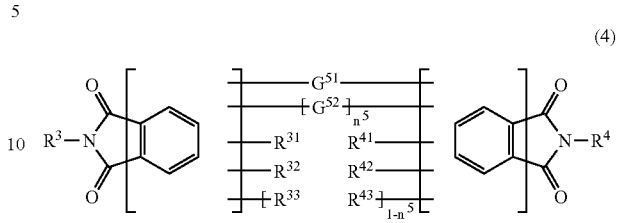

(4)

wherein $R^3$, $R^4$, $R^{31}$ to $R^{33}$, and $R^{41}$ to $R^{43}$ each independently represent a hydrogen or halogen atom; a group selected from nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, substituted or unsubstituted heteroarylthio, or substituted or unsubstituted metallocenyl; or, in a combination of $R^{31}$ to $R^{33}$ and/or a combination of $R^{41}$ to $R^{43}$, two or more substituents selected from each of the combinations may independently combine via a linking group within the same combination to form a cyclic structure together with carbon atoms to which they are attached; $G^{51}$ and $G^{52}$ represent a bivalent linking group selected from a single bond, substituted or unsubstituted bivalent aliphatic hydrocarbon group, and substituted or unsubstituted bivalent aromatic ring group; $n^5$ represents 0 or 1, with the proviso that at least one of $R^3$ and $R^4$ represents alkyl, aralkyl or aromatic ring substituted by a substituted or unsubstituted metallocene residue.

Specific examples represented by $R^3$, $R^4$, $R^{31}$ to $R^{33}$, and $R^{41}$ to $R^{43}$, of halogen, nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, substituted or unsubstituted heteroarylthio, or substituted or unsubstituted metallocenyl are the same groups as the substituents substituting a ring AR of the formula (1) mentioned above.

Examples of the linking group where, in a combination of $R^{31}$ to $R^{33}$ and/or a combination of $R^{41}$ to $R^{43}$, two or more substituents selected from each of the combinations may independently combine via a linking group within the same combination to form a cyclic structure together with carbon atoms to which they are attached are the same linking groups as those of $T^1$ of the formula (15) and $T^2$ of the formula (16).

Furthermore, in bivalent linking groups represented by $G^{51}$ and $G^{52}$, examples of a substituted or unsubstituted bivalent aliphatic hydrocarbon and substituted or unsubstituted bivalent aromatic ring are the same linking groups as those of $G^{41}$ and $G^{42}$ of the formula (3) mentioned above.

Examples of alkyl, aralkyl or aromatic ring substituted by a substituted or unsubstituted metallocene residue of $R^3$ and $R^4$ include the same groups as alkyl, aralkyl, or aromatic ring substituted by a substituted or unsubstituted metallocene group represented by $R^1$ and $R^2$. Furthermore, preferable examples of $R^3$ and $R^4$ include the same group as $R^1$ and $R^2$ of the formula (3).

Moreover, a preferable form of an imide compound according to the present invention includes a compound represented by the following general formula (5):

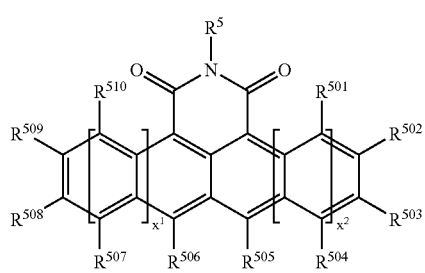

(5)

wherein $R^{501}$ to $R^{510}$ each independently represent a hydrogen or halogen atom; a group selected from nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, substituted or unsubstituted heteroarylthio, or substituted or unsubstituted metallocenyl; or, two or more substituents selected from the combination of $R^{501}$ to $R^{510}$ may each independently combine via a linking group to form a cyclic structure together with carbon atoms to which they are attached; $R^5$ represents a group in which a substituted or unsubstituted metallocene residue bonds to the nitrogen atom of the imide group via a bivalent linking group composed of at least one selected from a substituted or unsubstituted bivalent aliphatic hydrocarbon or substituted or unsubstituted bivalent aromatic ring; and $X^1$ and $X^2$ represent an integer of 0 to 2.

Specific examples represented by $R^{501}$ to $R^{510}$, of halogen, nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, substituted or unsubstituted heteroarylthio, and substituted or unsubstituted metallocenyl are the same as the substituents substituting a ring AR of the formula (1) mentioned above.

Examples of the linking group where, two or more substituents selected from the combination of $R^{501}$ to $R^{510}$ may each independently combine via a linking group to form a cyclic structure together with carbon atoms to which they are attached are the same linking groups as those of $T^1$ of the formula (15) and $T^2$ of the formula (16).

Examples of alkyl, aralkyl or aromatic ring substituted by a substituted or unsubstituted metallocene residue represented by $R^5$ include alkyl, aralkyl, or aromatic ring substituted by a substituted or unsubstituted metallocene group represented by $R^1$ and $R^2$ of the formula (3). Further preferable examples of $R^5$ include the same groups of $R^1$ and $R^2$ of the formula (3).

In a compound represented by the formula (5), two or more molecules independent of each other may be combined via a linking group T to form a single molecule. Preferable linking groups include those formed by appropriately combining carbonyl, substituted or unsubstituted imino, substituted or unsubstituted phenylene, and oxa.

A preferable form of an imide compound according to the present invention includes a compound represented by the following general formula (6):

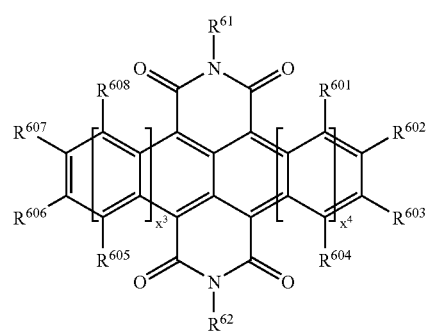

(6)

wherein $R^{601}$ to $R^{608}$ each independently represent a hydrogen or halogen atom; a group selected from nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, substituted or unsubstituted heteroarylthio, or substituted or unsubstituted metallocenyl; or, in a combination of $R^{601}$ to $R^{604}$ and/or a combination of $R^{605}$ to $R^{608}$, two or more substituents selected from each of the combinations may independently combine via a linking within the same combination to form a cyclic structure together with carbon atoms to which they are attached; $R^{61}$ and $R^{62}$ represent a group in which a substituted or unsubstituted metallocene residue bonds to the nitrogen atom of the imide group via a bivalent linking group composed of at least one selected from a substituted or unsubstituted bivalent aliphatic hydrocarbon and substituted or unsubstituted bivalent aromatic ring; and $X^3$ and $X^4$ represent an integer of 0 to 2.

Specific examples represented by $R^{601}$ to $R^{608}$, of halogen atom, nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, substituted or unsubstituted heteroarylthio, or substituted or unsubstituted metallocenyl are the same groups as substituents substituting a ring AR of the formula (1) mentioned above.

Examples of the linking group where, in a combination of $R^{601}$ to $R^{604}$ and/or a combination of $R^{605}$ to $R^{608}$, two or more substituents selected from each of the combinations may independently combine via a linking group within the same combination to form a cyclic structure together with carbon atoms to which they are attached, are the same linking groups as those of $T^1$ of the formula (15) and $T^2$ of the formula (16).

Examples of alkyl, aralkyl or aromatic ring substituted by a substituted or unsubstituted metallocene residue represented by $R^{61}$ and $R^{62}$ include the same alkyl, aralkyl, or aromatic ring substituted by substituted or unsubstituted metallocene residue represented by $R^1$ and $R^2$ of the formula (3). Further preferable examples of $R^{61}$ and $R^{62}$ include the same groups as $R^1$ and $R^2$ of the formula (3).

Furthermore, a preferable form of an imide compound according to the present invention includes a compound represented by the general formula (7) below:

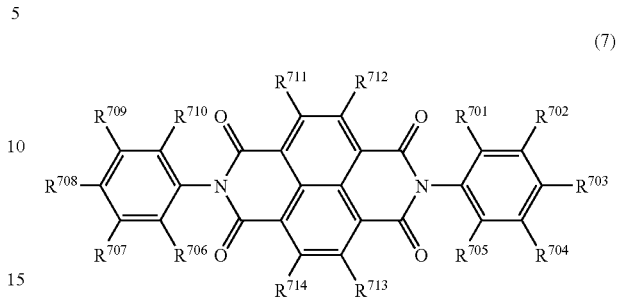

(7)

wherein $R^{701}$ to $R^{714}$ each independently represent a hydrogen or halogen atom; a group selected from nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, substituted or unsubstituted heteroarylthio, or substituted or unsubstituted metallocenyl; or, in a combination of $R^{701}$ to $R^{705}$ and/or a combination of $R^{706}$ to $R^{710}$, and/or combination of $R^{711}$ to $R^{715}$, two or more substituents selected from each of the combinations each may independently combine via a linking group within the same combination to form a cyclic structure together with carbon atoms to which they are attached, with the proviso that any one or more groups selected from $R^{701}$ to $R^{710}$ represent substituted or unsubstituted metallocenyl.

Specific examples represented by $R^{701}$ to $R^{714}$, of halogen, nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, substituted or unsubstituted heteroarylthio, or substituted or unsubstituted metallocenyl are the same substituents as those for a ring AR of the formula (1) mentioned above.

Examples of the linking group where, in a combination of $R^{701}$ to $R^{705}$ and/or a combination of $R^{706}$ to $R^{710}$, and/or combination of $R^{711}$ to $R^{715}$, two or more substituents selected from each of the combinations each may independently combine via a linking group within the same combination to form a cyclic structure together with carbon atoms to which they are attached are the same linking groups as those of $T^1$ of the formula (15) and $T^2$ of the formula (16).

Examples of a substituted or unsubstituted metallocene group represented by $R^{701}$ to $R^{710}$ include the same groups as a substituted or unsubstituted metallocene residue represented by $R^1$ and $R^2$ of the formula (3).

A preferable form of an imide compound according to the present invention includes an imide compound having a quinazoline residue, more preferably, an imide compound having a quinazoline-4-on (or called quinazolone). Specific examples include, as a tautomeric structure, a compound represented by the general formula (8):

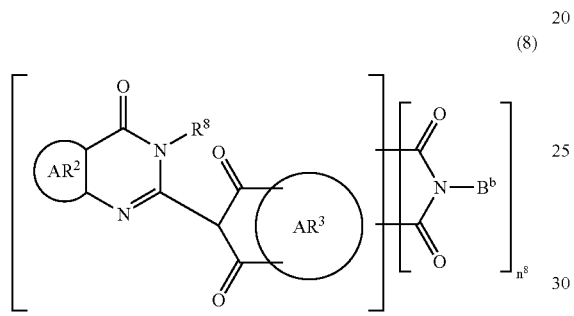

(8)

wherein a ring $AR^2$ and ring $AR^3$ represent a substituted or unsubstituted aromatic ring residue or a residue formed by combining two or more aromatic ring residues via one or more linking groups; $R^8$ represents a hydrogen atom or a substituent; $n^8$ represents the number of imide groups bonded to the ring AR2 and/or ring AR3; $B^b$ represents a substituent of $B^1$ to $B''^8$ bonded to a nitrogen atom of each imide group; and b represents an integer of from 1 to $n^8$, with the proviso that at least one substituent selected from $B^1$ to $B''^8$ is one having one or more substituted or unsubstituted metallocene residues.

Specific examples of an aromatic ring residue or a residue formed by combining two or more aromatic ring residues via one or more linking groups, represented by a ring $AR^2$ and ring $AR^3$, include the same residues as an aromatic ring residue or a residue formed by combining two or more aromatic ring residues represented by a ring AR. As a linking group, the same linking group as linking group T of the formula (1) may be mentioned.

The number of imide groups represented by $n^8$ is preferably 1 or 2, and more preferably 1.

Specific examples of a substituent bonded to the nitrogen atom of each imide group and represented by $B^b$ are the same group as represented by $A^m$ of the formula (1).

Specific examples of a substituent represented by $R^8$ include the same group as a substituent represented by $A^m$ of the formula (1). Preferable examples of a substituent include the aforementioned substituted or unsubstituted alkyl, substituted or unsubstituted aralkyl, and substituted or unsubstituted aromatic ring.

A compound represented by the general formula (8) of the present invention has as a tautomeric structure and may have a tautomer. Specific examples include structures represented by the following general formulas (8), (81), (82), and (83).

In the present invention, the general formula (8) is employed for convenience sake. Therefore, any compound having structures represented by the general formulas (8), (81), (82), and (83) or mixtures of compounds having the structures represented by the general formulas (8), (81), (82), and (83) may be used without limitation.

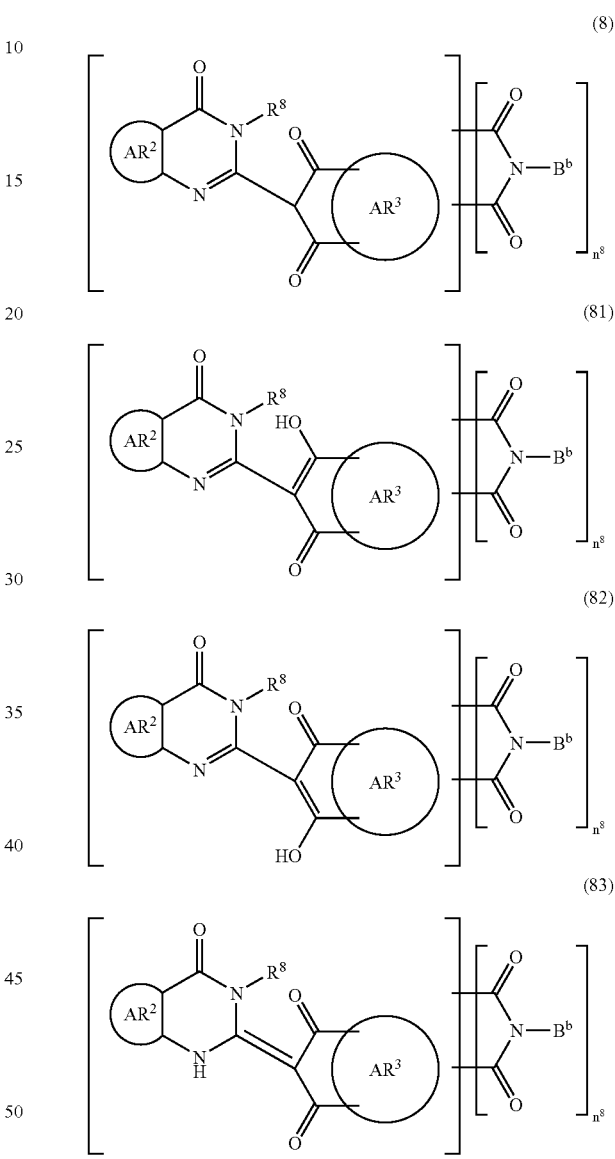

A compound represented by the general formula (8) of the present invention where $R^8$ is a hydrogen atom, may have tautomers of structures represented by general formulas (8a), (81a), (82a) and (83a) below, general formulas (8b), (81b) and (82b) below, and general formulas (8c), (81c), (82c) and (83c) below. A compound represented by the general formula (8) of the present invention may be a compound having a structure represented by general formula (8a), (81a), (82a) or (83a), general formula (8b), (81b) or (82b), or general formula (8c), (81c), (82c) or (83c) below, or a mixture of structures of general formulas (8a), (81 a), (82a) or (83a), formulas (8b), (81b) or (82b) and formulas (8c), (81c), (82c) or (83c). These may be used without limitation.

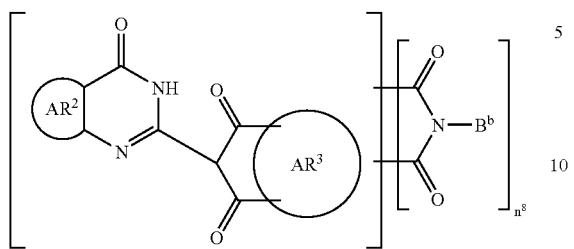
(8a)
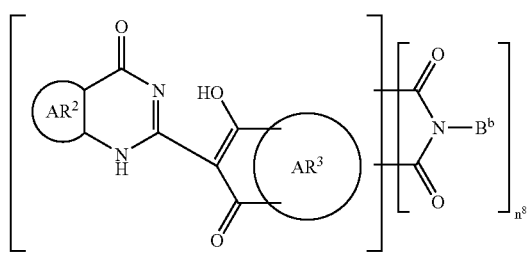
(81b)
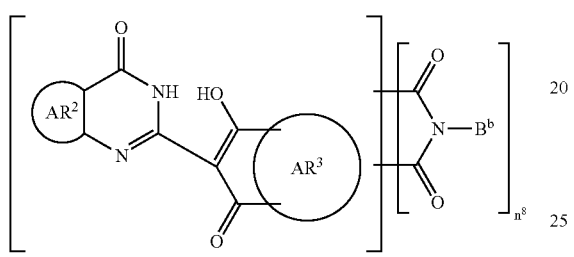
(81a)
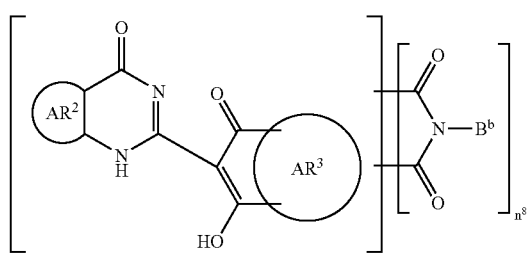
(82b)
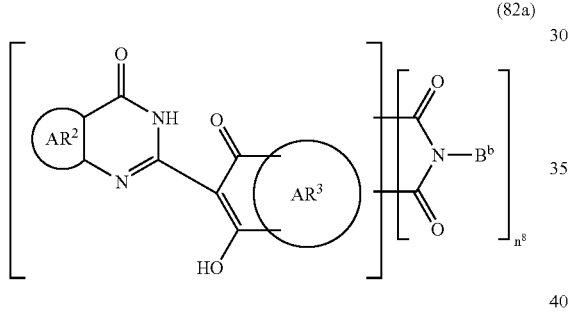
(82a)
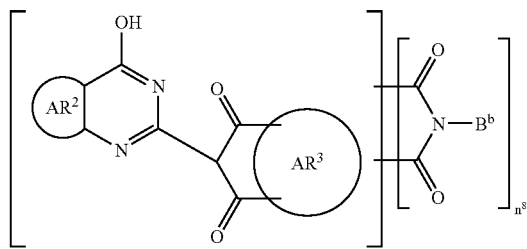
(8c)
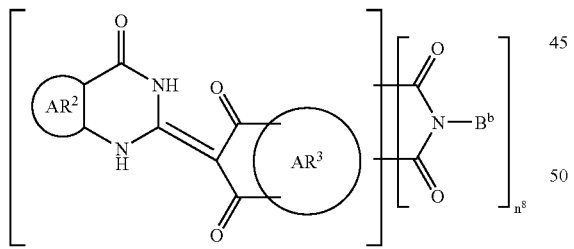
(83a)
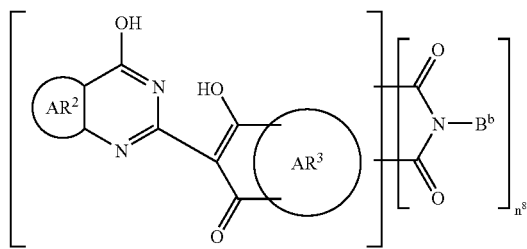
(81c)
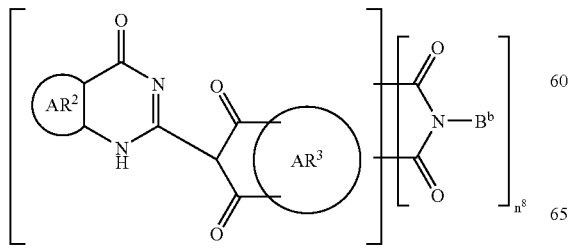
(8b)
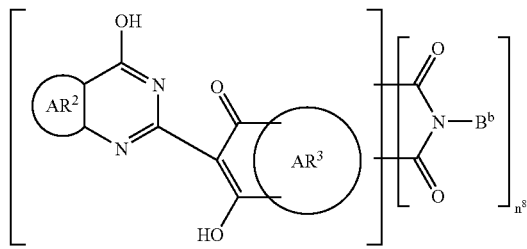
(82c)

-continued (83c)

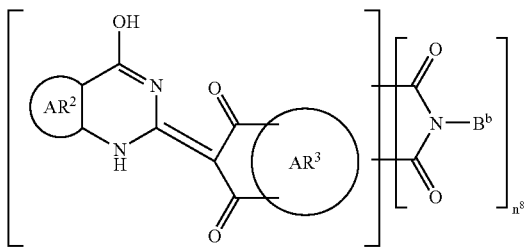

Furthermore, a preferable form of an imide compound according to the present invention includes a compound represented by the following general formula (9):

(9)

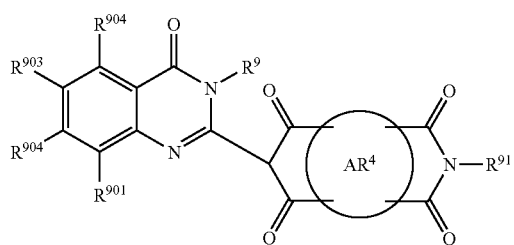

wherein a ring $AR^4$ represents a substituted or unsubstituted aromatic ring residue or a residue formed by combining two or more aromatic ring residues via one or more linking groups; $R^9$ represents hydrogen, substituted or unsubstituted alkyl, substituted or unsubstituted aralkyl, or substituted or unsubstituted aromatic ring; $R^{901}$ to $R^{904}$ each independently represent a hydrogen or halogen atom; a group selected from nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, substituted or unsubstituted heteroarylthio, or substituted or unsubstituted metallocenyl; or, in a combination of $R^{901}$ to $R^{904}$, two or more substituents selected from the combination may independently combine via a linking group to form a cyclic structure together with carbon atoms to which they are attached; and $R^{91}$ represents a group in which a substituted or unsubstituted metallocene residue bonds to the nitrogen atom of the imide via a bivalent linking group composed of at least one selected from a substituted or unsubstituted bivalent aliphatic hydrocarbon and substituted or unsubstituted bivalent aromatic ring.

Specific examples of an aromatic ring residue represented by a ring $AR^4$ include the same residues as an aromatic ring residue represented by a ring AR of the formula (1).

Specific examples of a linking group in the residue formed by combining two or more aromatic ring residues via one or more linking groups and represented by a ring $AR^4$ include the same linking group as a linking group T of the formula (1).

Specific examples of substituted or unsubstituted alkyl, substituted or unsubstituted aralkyl, and substituted or unsubstituted aromatic ring represented by $R^9$ include the same group as substituents substituting a ring AR of the formula (1).

Specific examples represented by $R^{901}$ to $R^{904}$, of halogen, nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, substituted or unsubstituted heteroarylthio, or substituted or unsubstituted metallocenyl include the same groups as substituents substituting a ring AR of the formula (1).

Examples of the linking group where, in a combination of $R^{901}$ to $R^{904}$, two or more substituents selected from the combination may independently combine via a linking group to form a cyclic structure together with carbon atoms to which they are attached include the same linking groups as those of $T^1$ of the formula (15) and $T^2$ of the formula (16).

Examples of alkyl, aralkyl, or aromatic ring substituted by substituted or unsubstituted metallocene represented by $R^{91}$ include the same groups as alkyl, aralkyl, or aromatic ring substituted by substituted or unsubstituted metallocene represented by $R^1$ or $R^2$ of the formula (3). Further, preferable examples of $R^{91}$ include the same groups of $R^1$ and $R^2$ of the formula (3).

Examples of tautomers of compounds represented by the general formula (9) of the present invention include those having similar structures corresponding to general formulas (8), (81), (82), and (83) and may also include a mixture of tautomers of the structures. These may be used without limitation. In the general formula (9) where $R^9$ is a hydrogen atom, examples of tautomers may include those having similar structures corresponding to general formulas (8a), (81a), (82a), and (83a), general formulas (8b), (81b), and (82b), and general formulas (8c), (81c), (82c), and (83c) below and may also include a mixture of tautomers having individual structures. These may be used without limitation.

A preferable form of an imide compound according to the present invention includes, as a tautomeric structure, a quinazolone-phthalon compound represented by the general formula (10):

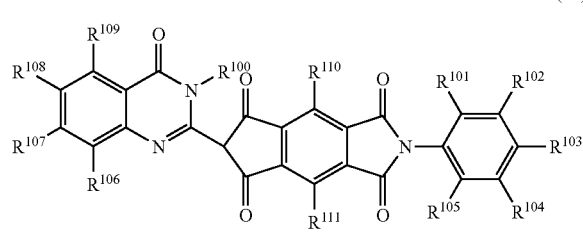

(10)

wherein $R^{100}$ represents hydrogen or substituted or unsubstituted alkyl, substituted or unsubstituted aralkyl or substituted or unsubstituted aromatic ring; $R^{101}$ to $R^{111}$ each independently represent a hydrogen or halogen atom; a group selected from nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, substituted or unsubstituted heteroarylthio, or substituted or unsubstituted metallocenyl; or, in a combination of $R^{101}$ to $R^{105}$, and/or a combination of $R^{106}$ to $R^{109}$, two or more substituents selected from each of the combinations may independently combine via a linking group in the same combination to form a cyclic structure together with carbon atoms to which they are attached, with the proviso that any one or more groups selected from $R^{101}$ to $R^{105}$ represent substituted or unsubstituted metallocenyl groups.

Specific examples of substituted or unsubstituted alkyl, substituted or unsubstituted aralkyl and substituted or unsubstituted aromatic ring represented by $R^{100}$ include the same groups as substituents substituting a ring AR of the formula (1).

Specific examples represented by $R^{101}$ to $R^{111}$, of halogen, nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, substituted or unsubstituted heteroarylthio, and substituted or unsubstituted metallocenyl include the same groups as substituents substituting a ring AR of the formula (1).

Specific examples of a linking group where, in a combination of $R^{101}$ to $R^{105}$ and/or a combination of $R^{106}$ to $R^{109}$, two or more substituents selected from each of the combinations may independently combine via a linking group in the same combination to form a cyclic structure together with carbon atoms to which they are attached include the same linking groups as those of $T^1$ of the formula (15) and $T^2$ of the formula (16).

Examples of substituted or unsubstituted metallocene represented by $R^{101}$ to $R^{105}$ include the same groups as the metallocene residues represented by $R^1$ and $R^2$ of the formula (3). Further preferable $R^{101}$ to $R^{105}$ include the same groups as those represented by $R^1$ and $R^2$ of the formula (3).

Examples of a tautomer of a compound represented by the general formula (10), include tautomers having similar structures corresponding to the general formulas (8), (81), (82), and (83), and may include a mixture of the tautomers of individual structures. These may be used without limitation. In the formula (10) where $R^{100}$ is a hydrogen atom, examples of a tautomer include tautomers having similar structures corresponding to general formulas (8a), (81a), (82a) and (83a), general formulas (8b), (81b) and (82b), and general formulas (8c), (81c), (82c) and (83c) or a mixture of the tautomers of individual structures. These may be used without limitation.

A preferable form of an imide compound according to the present invention, as a tautomeric structure, includes a quinazoline-naphthalone compound represented by the following general formula (11):

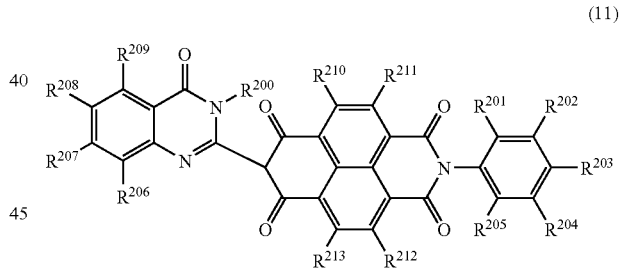

(11)

wherein $R^{200}$ represents hydrogen or substituted or unsubstituted alkyl, substituted or unsubstituted aralkyl, or substituted or unsubstituted aromatic ring; $R^{201}$ to $R^{213}$ each independently represent a hydrogen or halogen atom; a group selected from nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, substituted or unsubstituted heteroarylthio, or substituted or unsubstituted metallocenyl; or, in a combination of $R^{201}$ to $R^{205}$, and/or a combination of $R^{206}$ to $R^{209}$, and/or a combination of $R^{210}$ to $R^{211}$, and/or a combination of $R^{212}$ to $R^{213}$, two or more substituents selected from each of the combinations may independently combine via a linking group in the same combination to form a cyclic structure together with carbon atoms to which they are attached, with the proviso that any one or more groups selected from $R^{201}$ to $R^{205}$ represent substituted or unsubstituted metallocenyl groups.

Specific examples of substituted or unsubstituted alkyl, substituted or unsubstituted aralkyl, and substituted or unsubstituted aromatic ring represented by $R^{200}$, include the same groups as substituents substituting a ring AR of the formula (1).

Specific examples represented by $R^{201}$ to $R^{213}$, of halogen, nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, substituted or unsubstituted heteroarylthio, and substituted or unsubstituted metallocenyl include the same groups as substituents substituting a ring AR of the formula (1).

Specific examples of a linking group where, in a combination of $R^{201}$ to $R^{205}$, and/or a combination of $R^{206}$ to $R^{209}$, and/or a combination of $R^{210}$ to $R^{211}$, and/or a combination of $R^{212}$ to $R^{213}$, two or more substituents selected from each of the combinations may independently combine via a linking group in the same combination to form a cyclic structure together with carbon atoms to which they are attached include the same linking groups as those of $T^1$ of the formula (15) and $T^2$ of the formula (16).

Examples of substituted or unsubstituted metallocene represented by $R^{201}$ to $R^{205}$ include the same groups as substituted or unsubstituted metallocene represented by $R^1$ and $R^2$ of the formula (3). Further preferable $R^{201}$ to $R^{205}$ include the same groups as those represented by $R^1$ and $R^2$ of the formula (3).

Examples of a tautomer of a compound represented by the general formula (11), includes tautomers having similar structures corresponding to the general formulas (8), (81), (82), and (83), may also include a mixture of the tautomers of individual structures. These may be used without limitation.

In the formula (11) where $R^{200}$ is a hydrogen atom, examples of a tautomer include tautomers having similar structures corresponding to formulas (8a), (81a), (82a) and (83a), formulas (8b), (81b) and (82b), and formulas (8c), (81c), (82c) and (83c) and may also include a mixture of the tautomers of individual structures. These may be used without limitation.

Examples of an imide compound of the present invention for use in an optical recording medium of the present invention include, but not limited to compounds of A-1 to A-57, B-1 to B-70, C-1 to C-77, D-1 to D-115 and E-1.

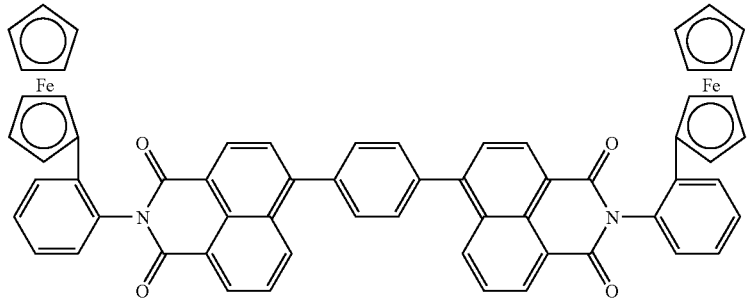

A-1

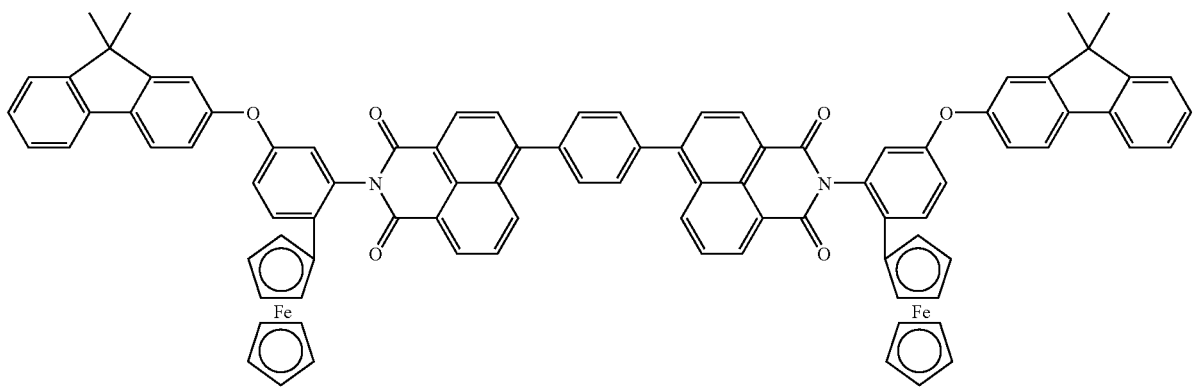

A-2

-continued
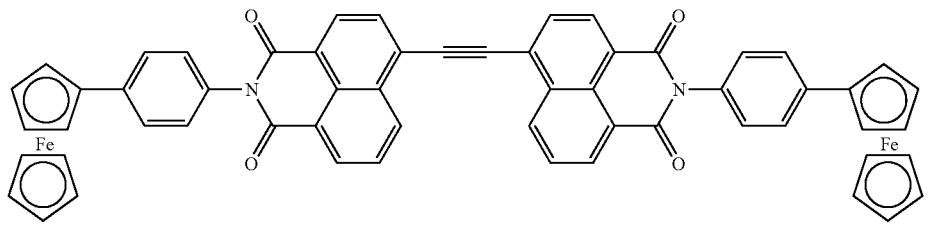
A-3
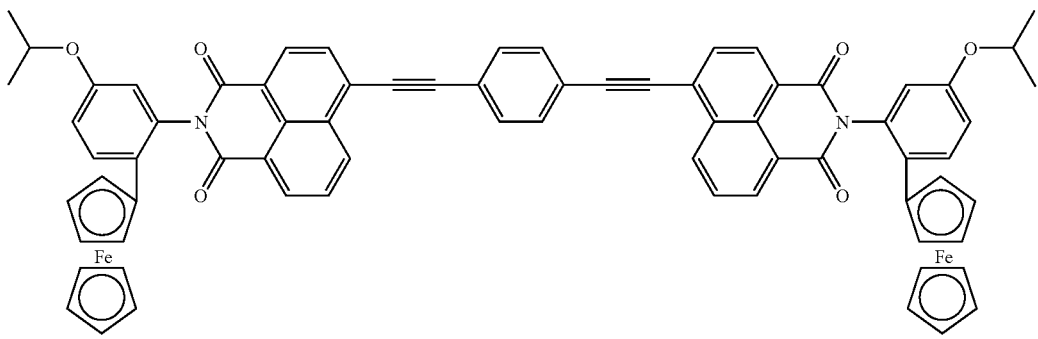
A-4
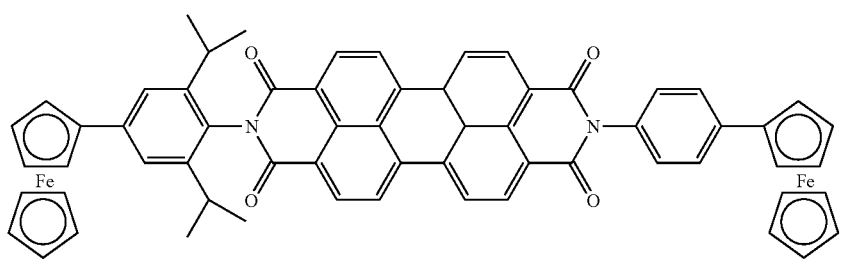
A-5
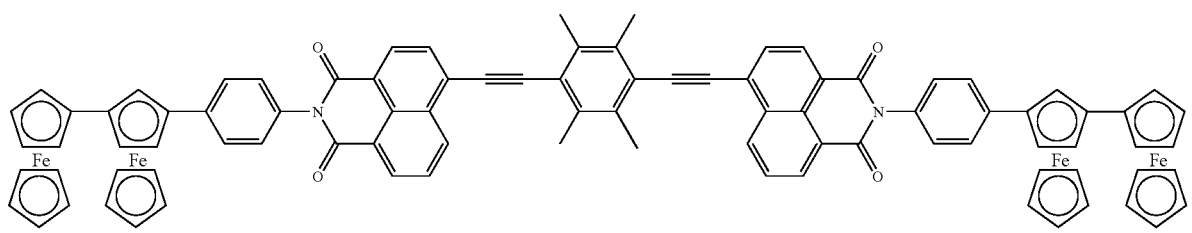
A-6
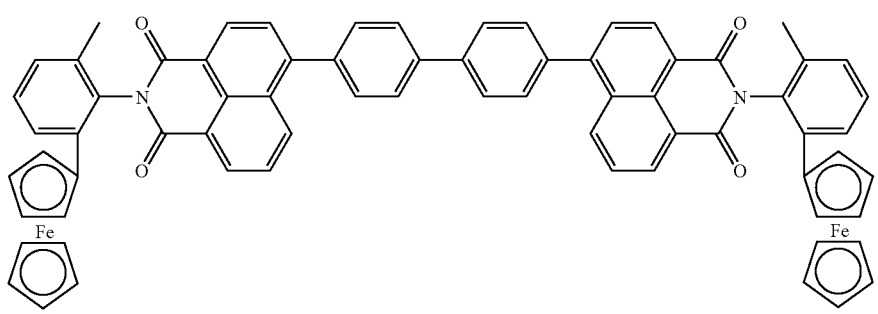
A-7

-continued
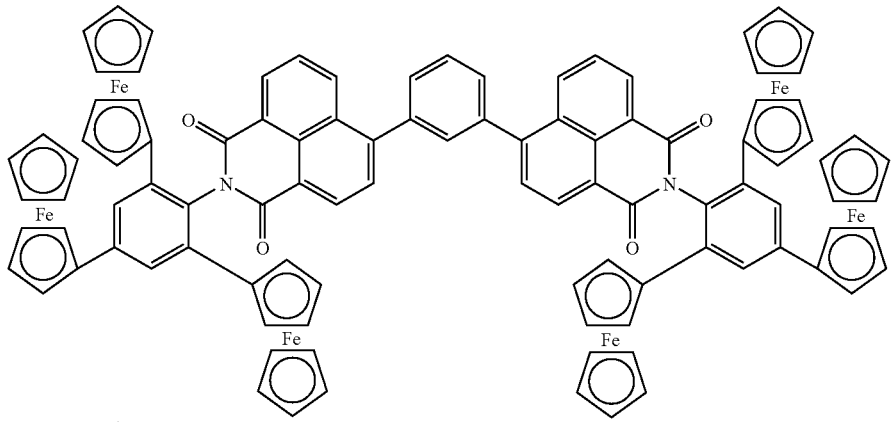
A-8
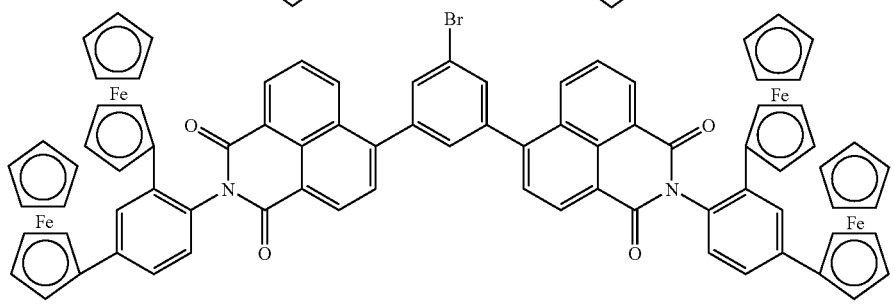
A-9
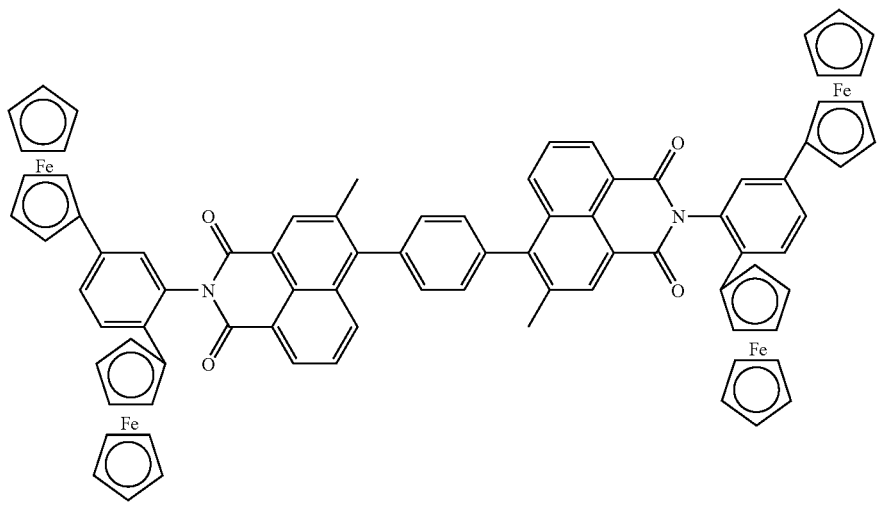
A-10
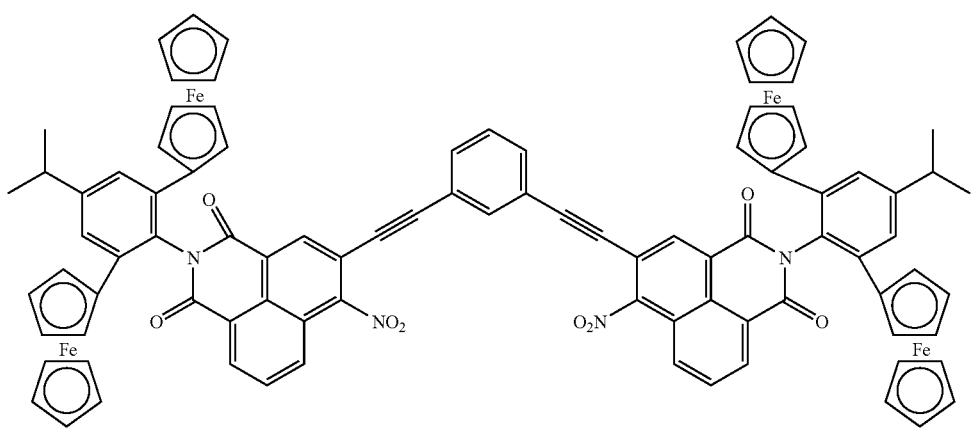
A-11

-continued
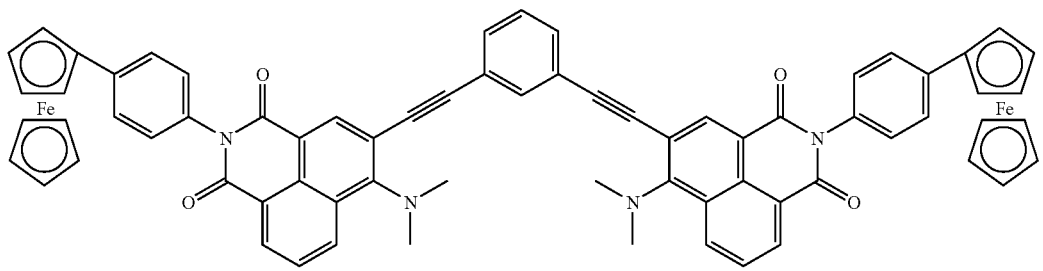
A-12
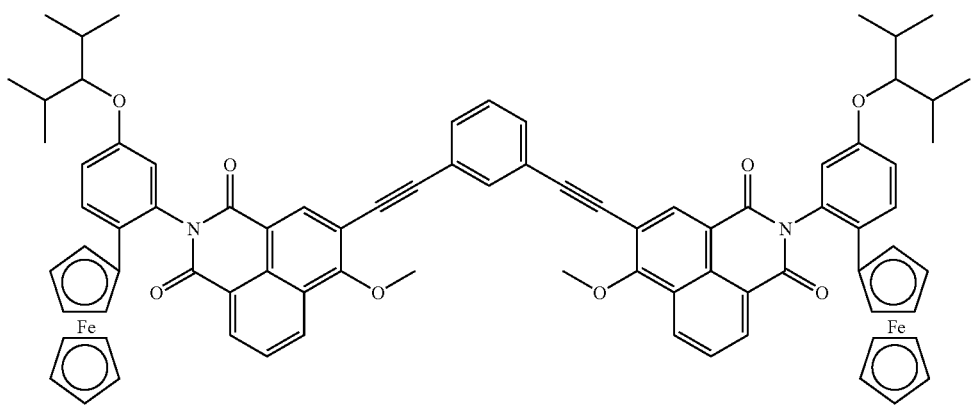
A-13
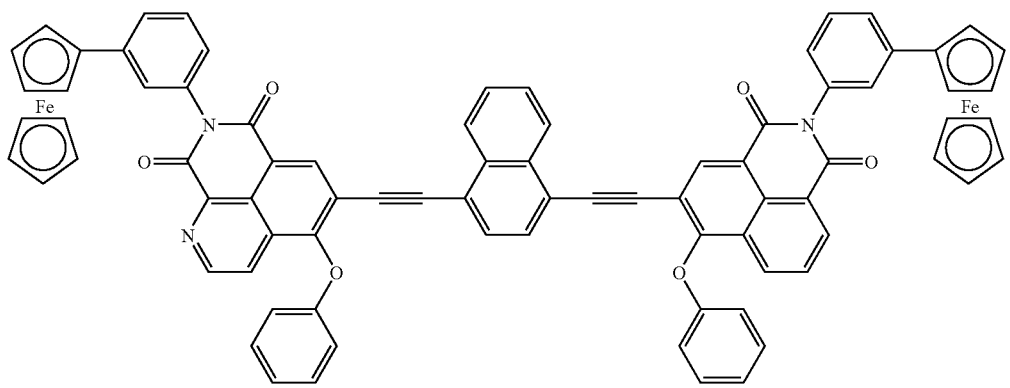
A-14
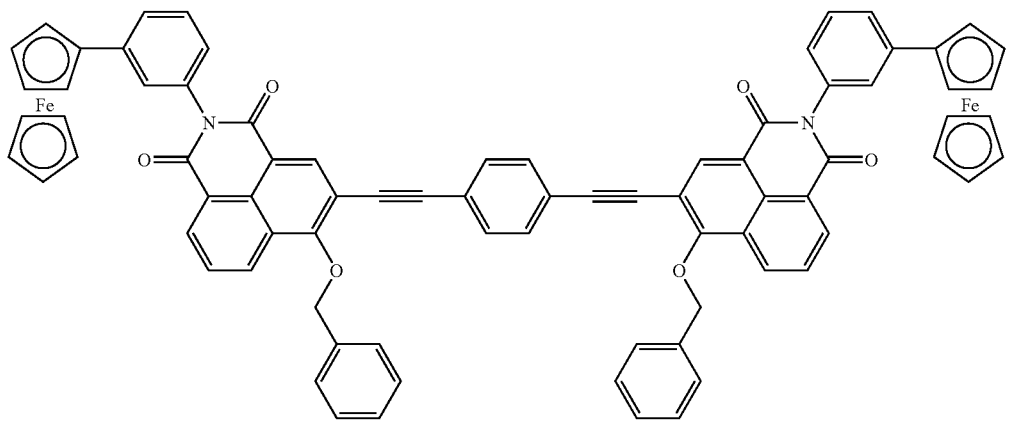
A-15

-continued
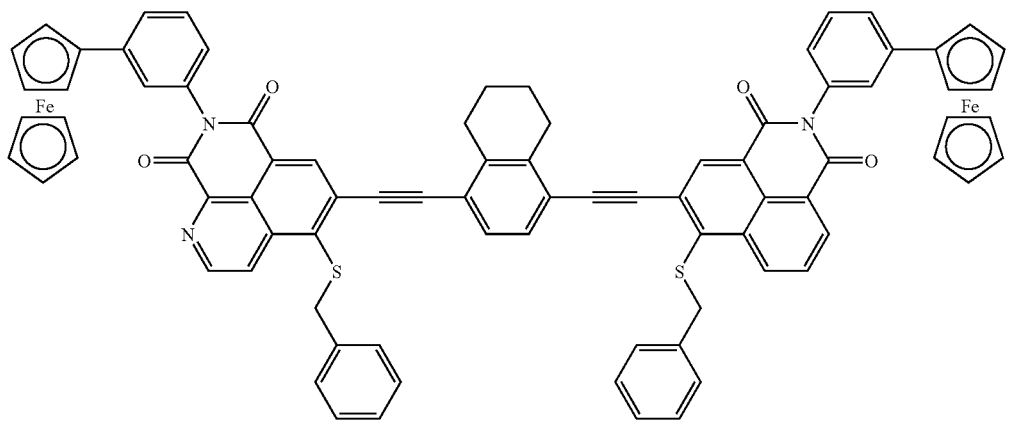
A-16
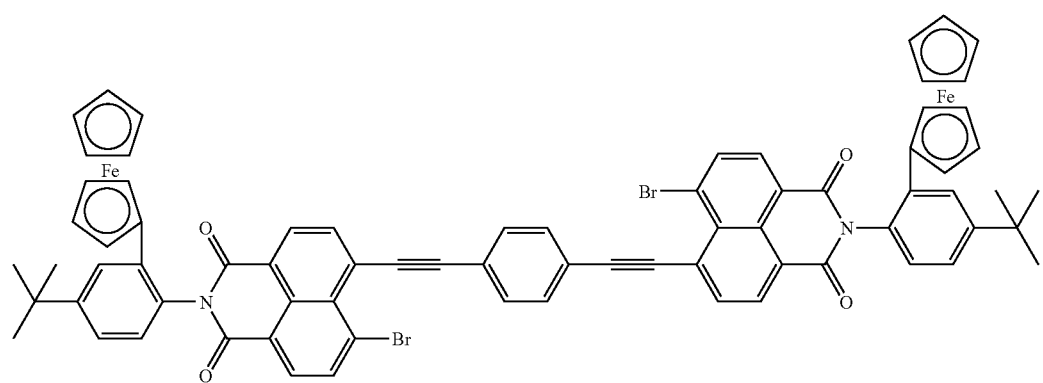
A-17
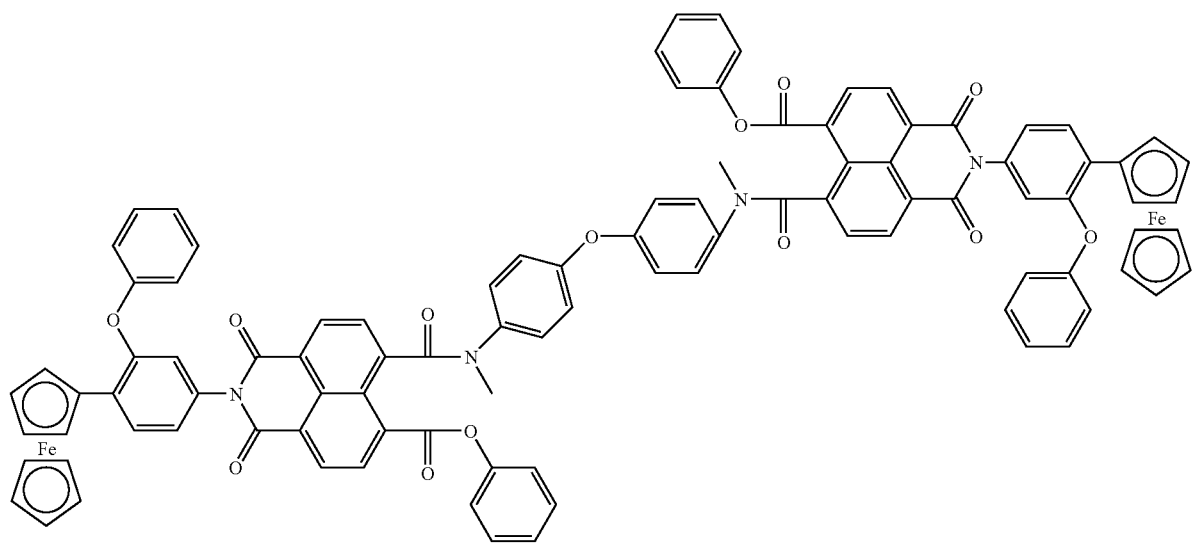
A-18

-continued
A-19
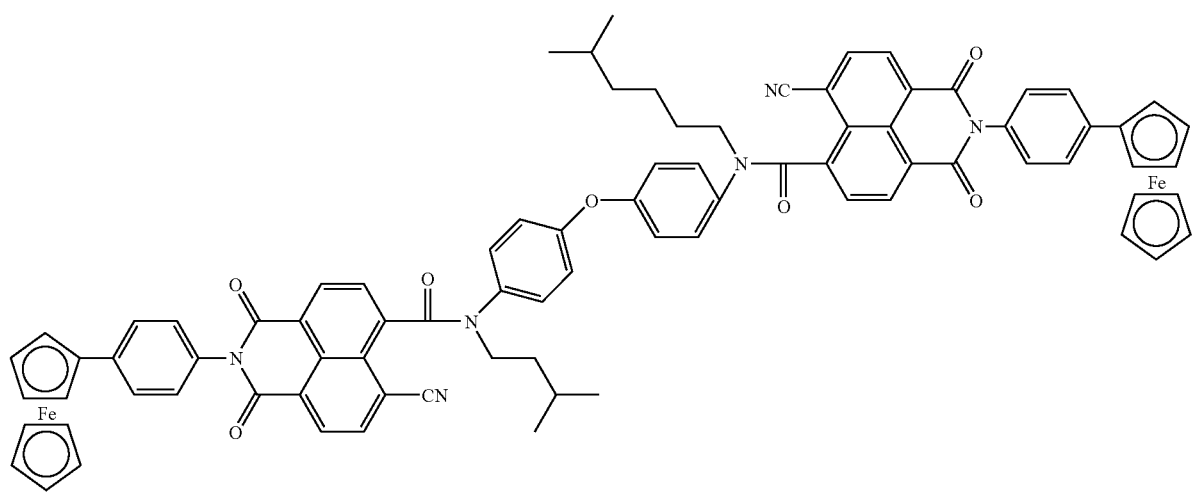
A-20
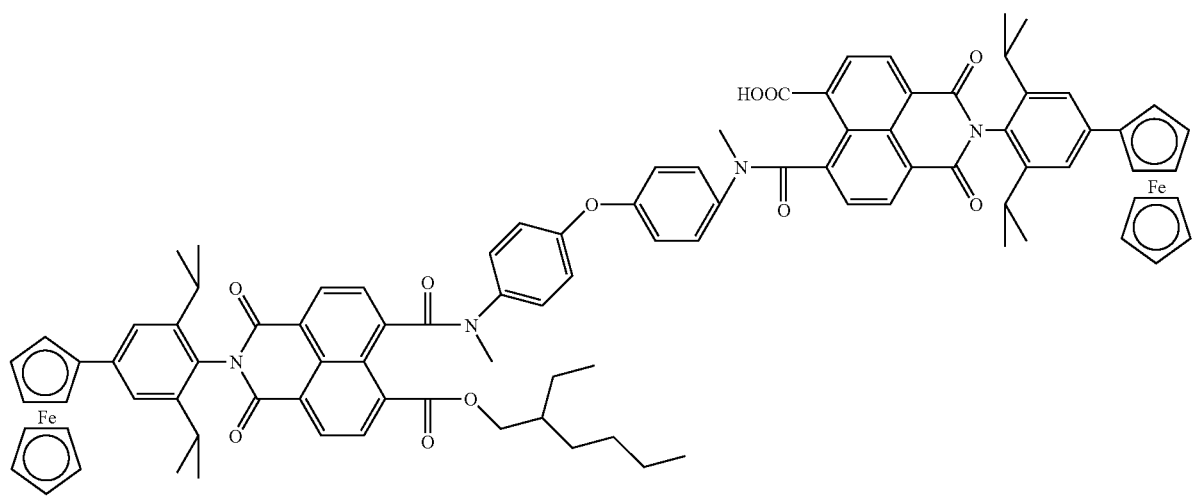
A-21
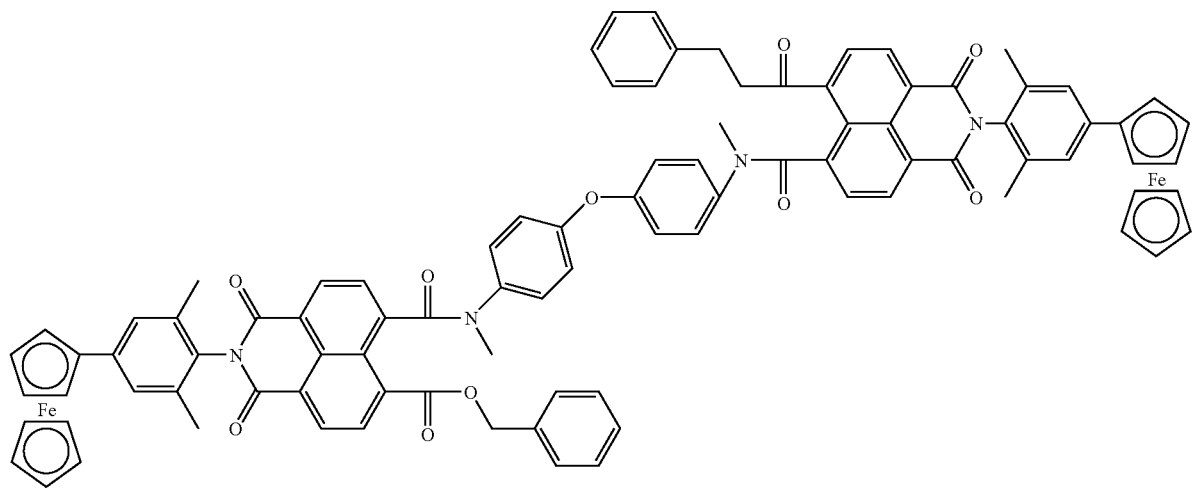

A-22
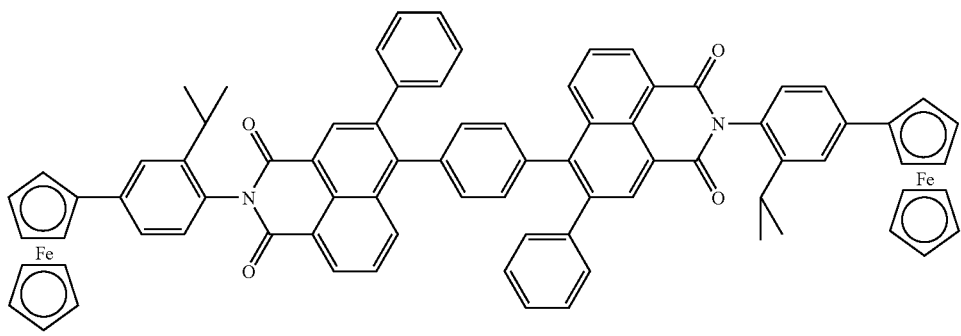
A-23
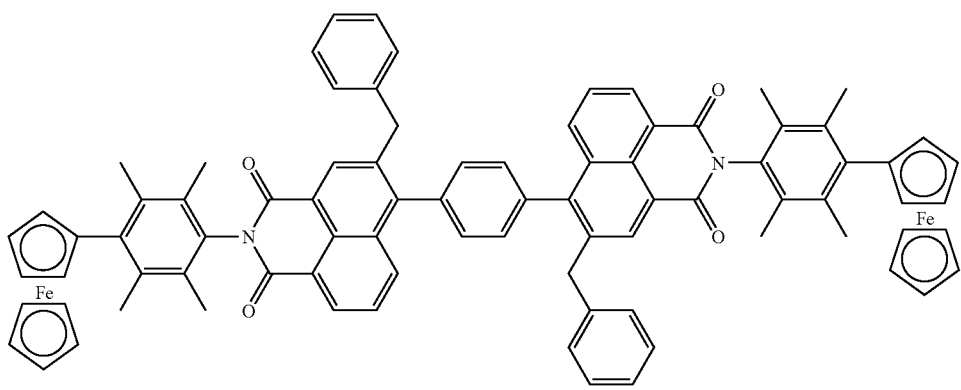
A-24
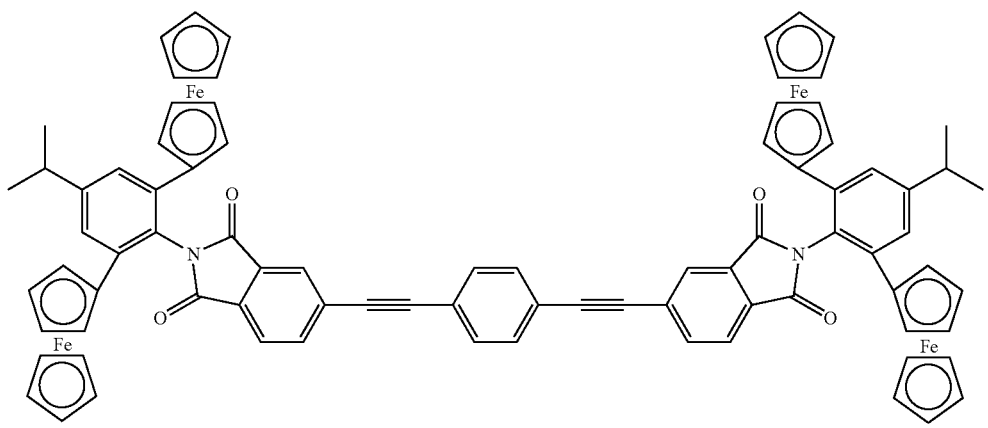
A-25
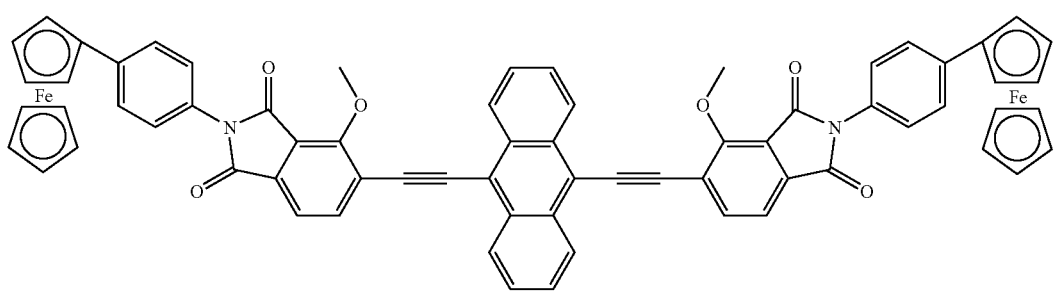

-continued
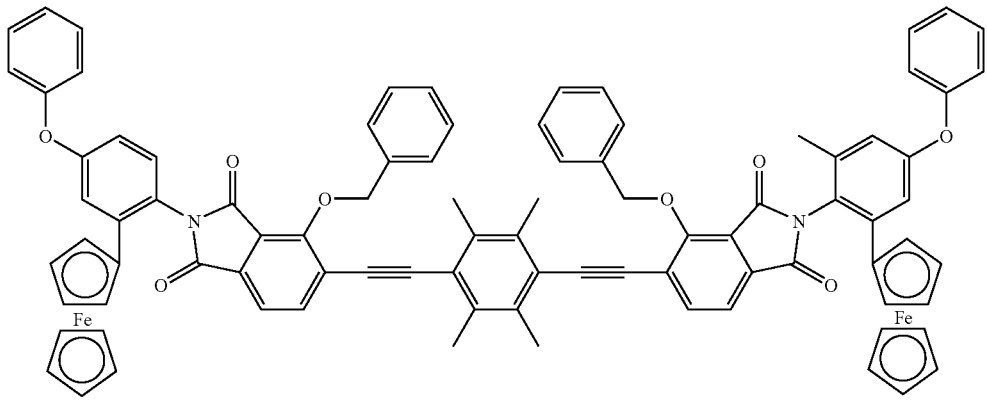
A-26
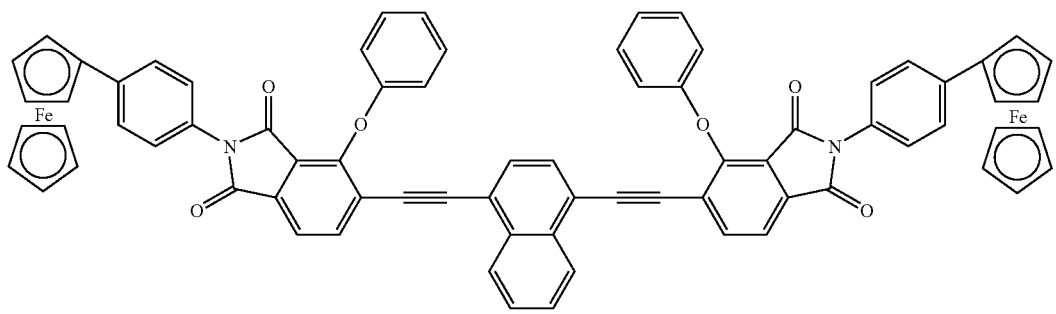
A-27
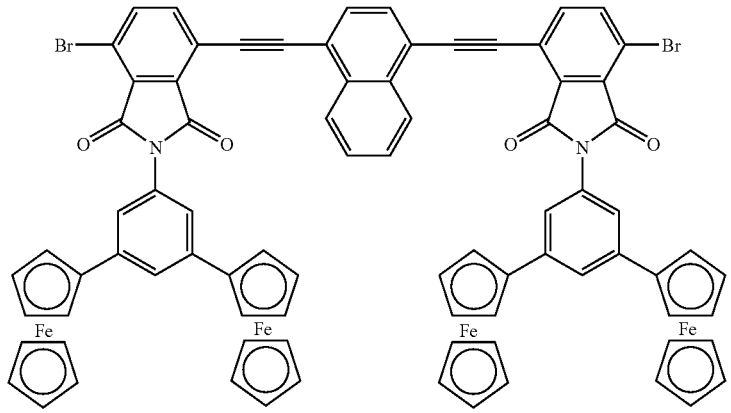
A-28
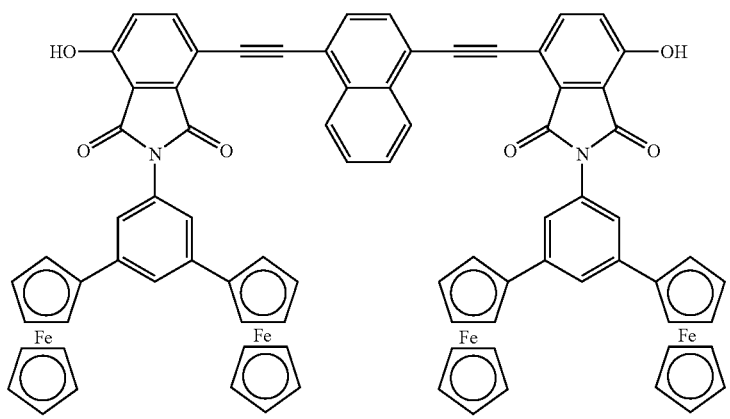
A-29

-continued
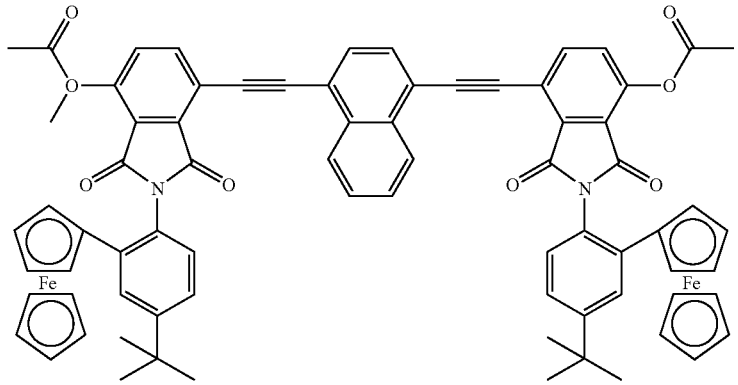
A-30
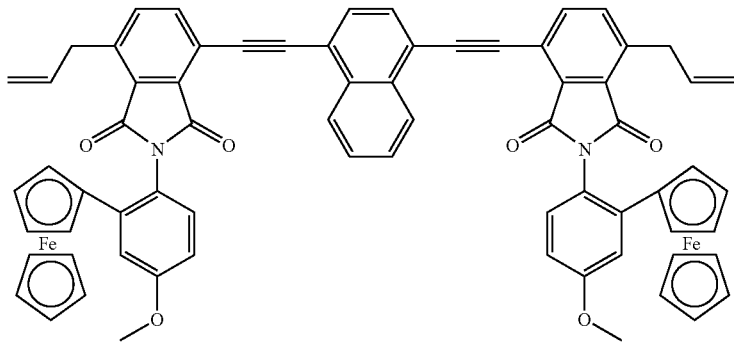
A-31
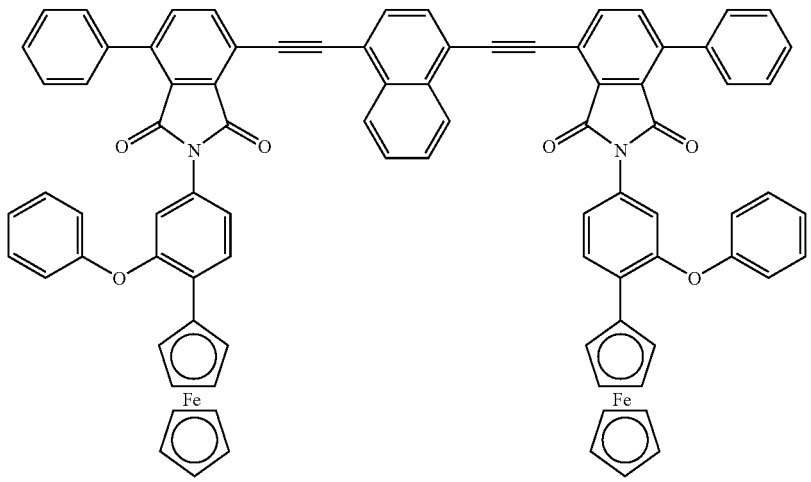
A-32
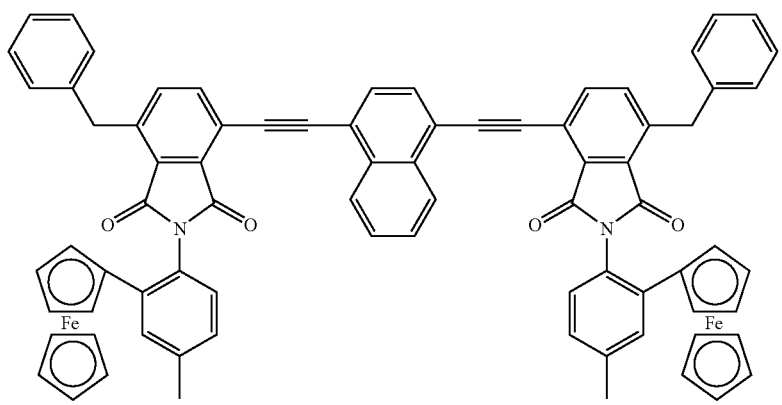
A-33

-continued
A-34
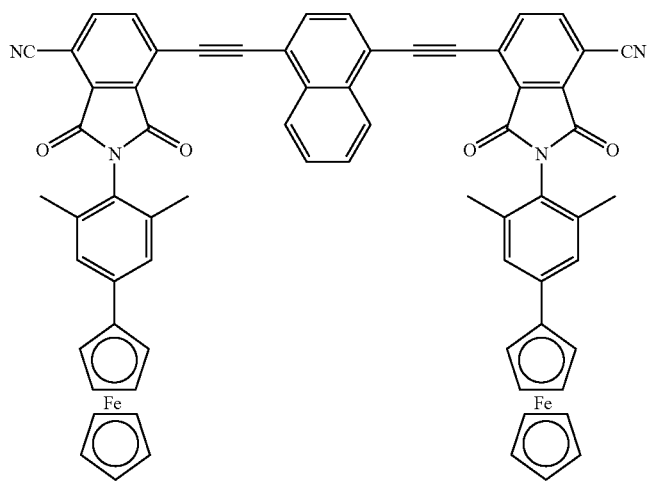
A-35
A-36
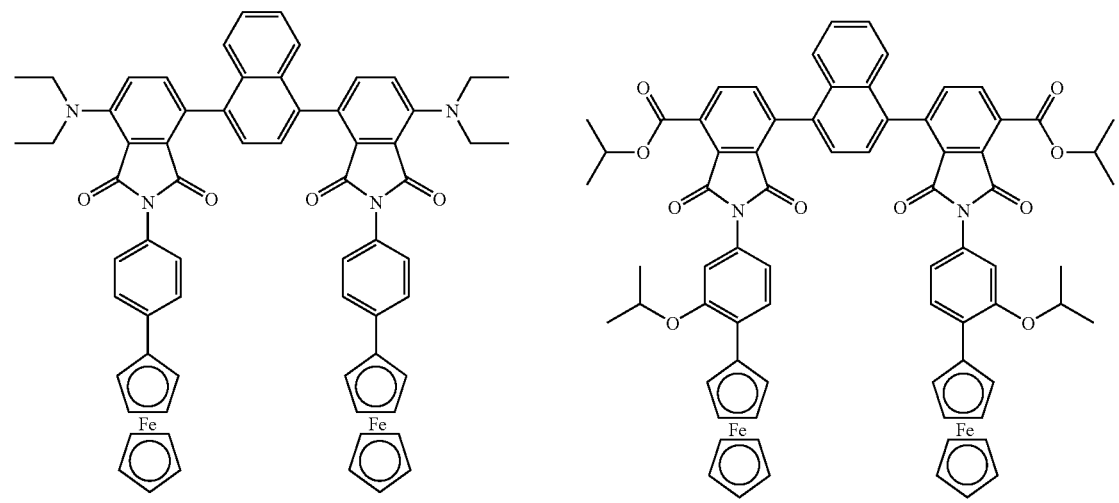
A-37
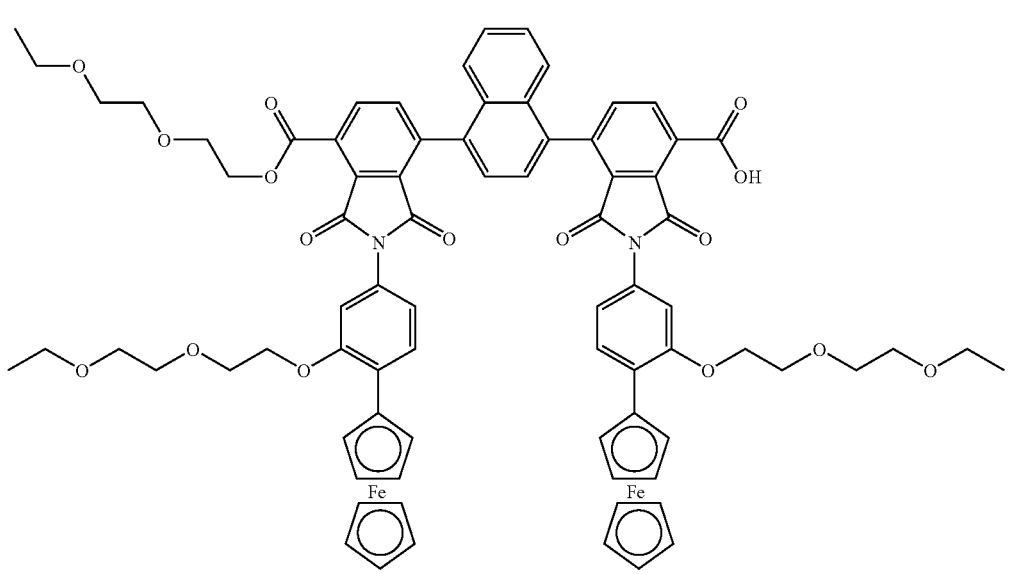

-continued
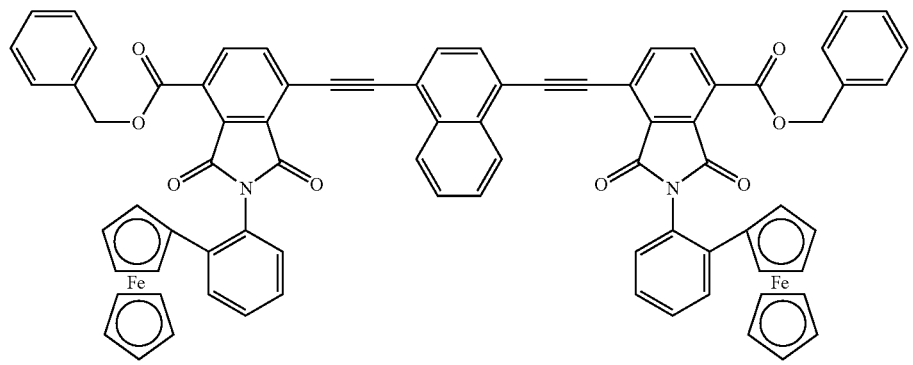
A-38
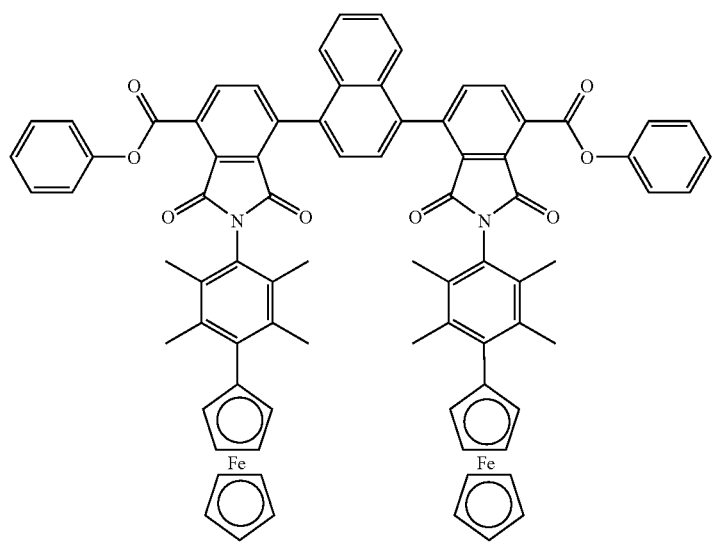
A-39
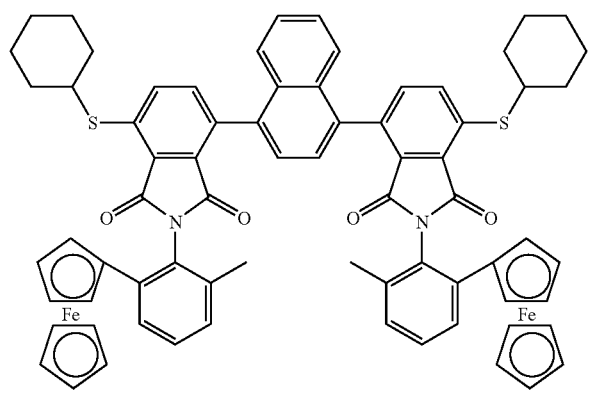
A-40

-continued
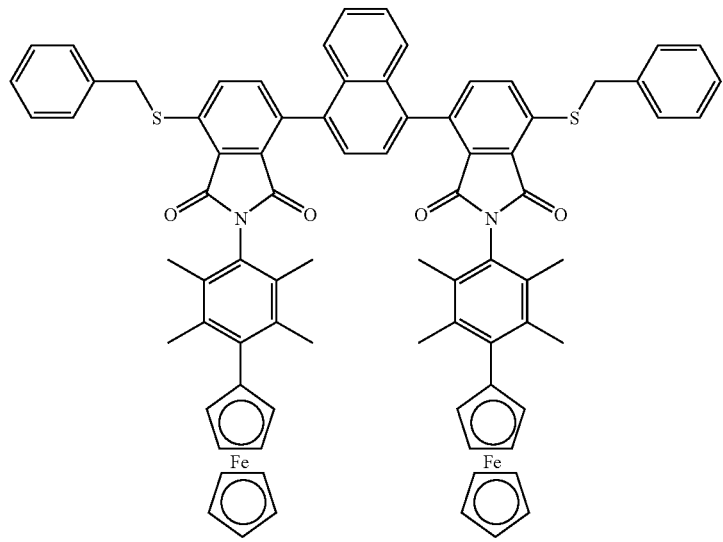
A-41
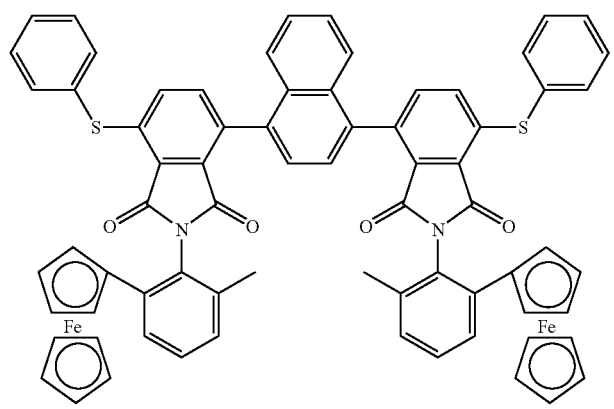
A-42
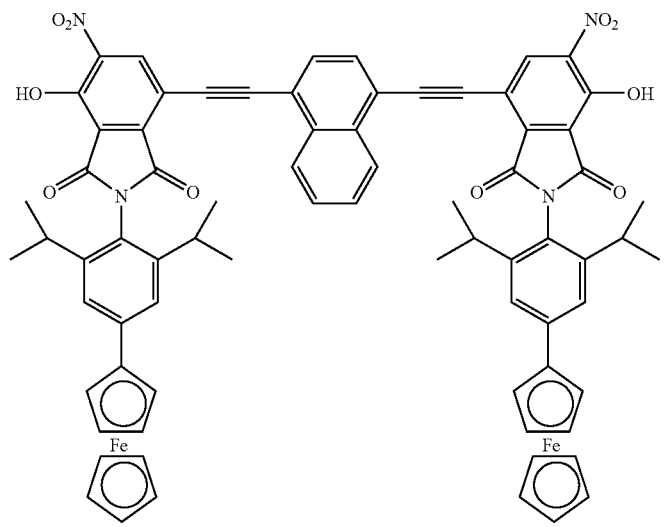
A-43

-continued
A-44
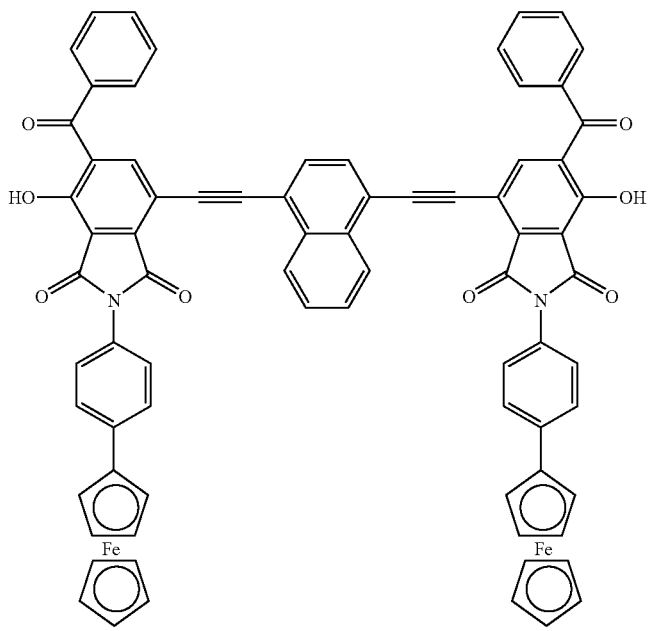
A-45
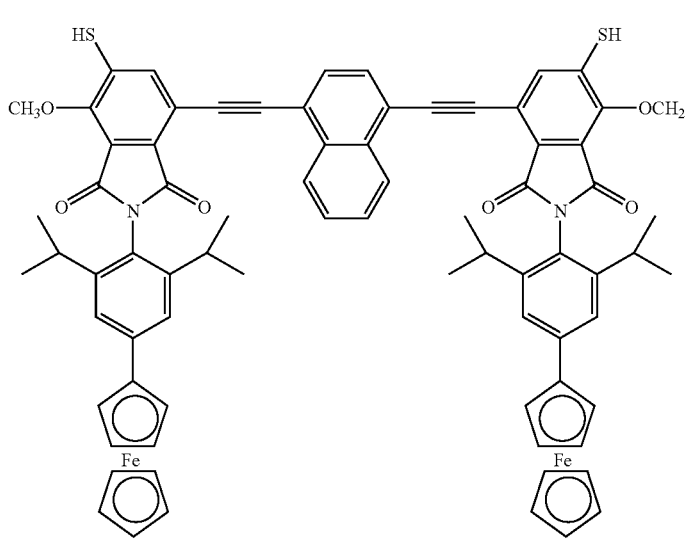
A-46
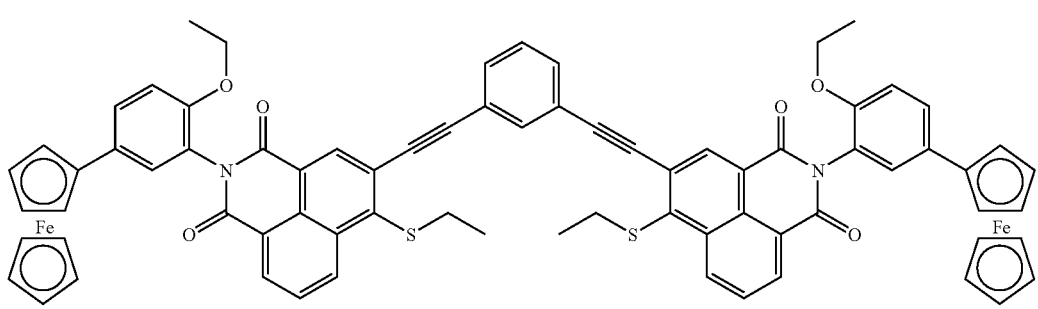

-continued
A-47
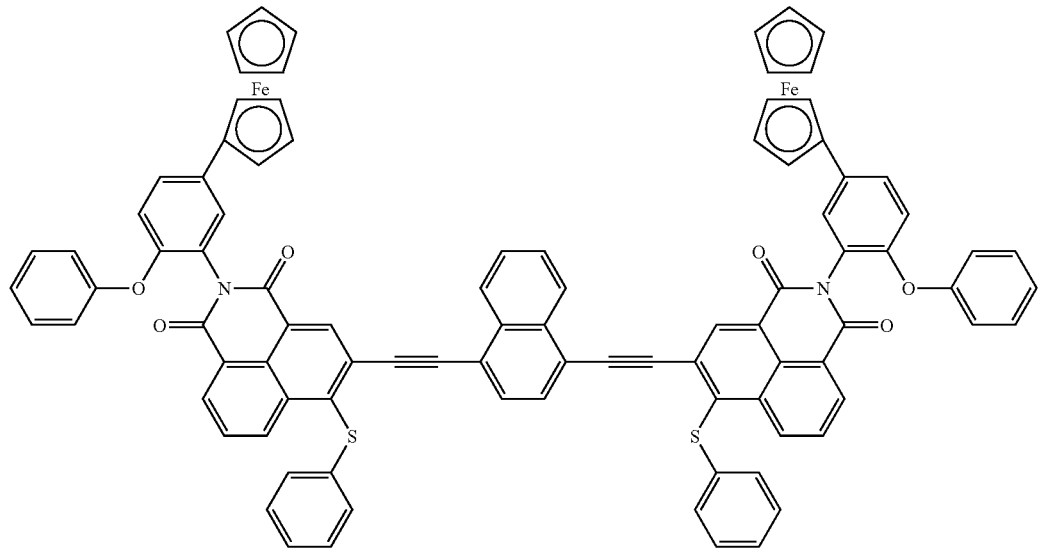
A-48
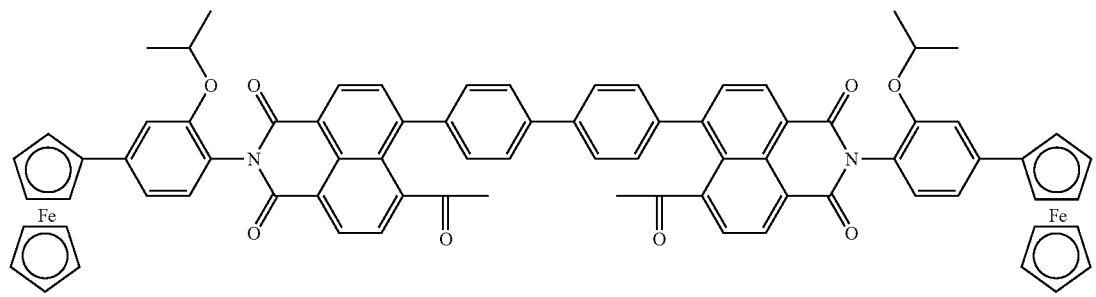
A-49
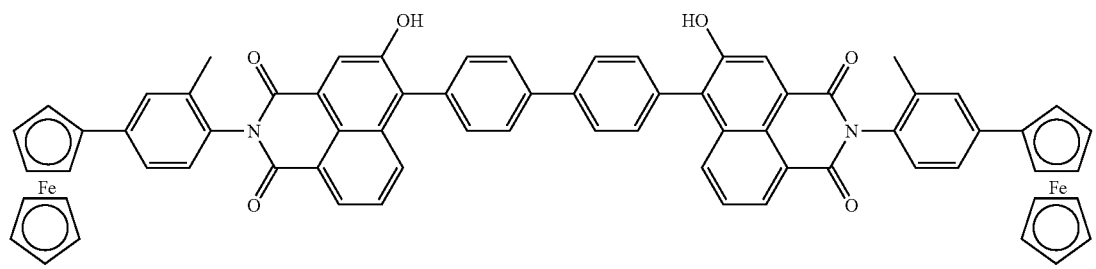
A-50
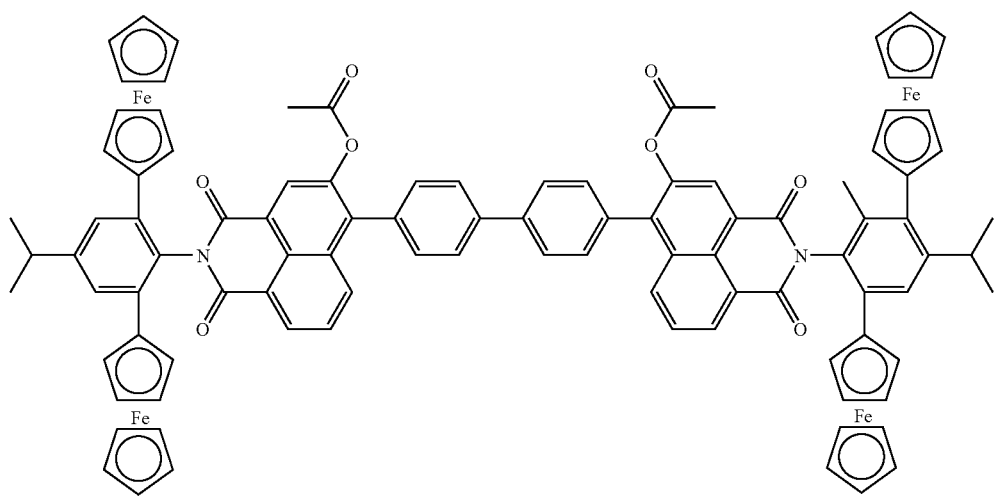

-continued
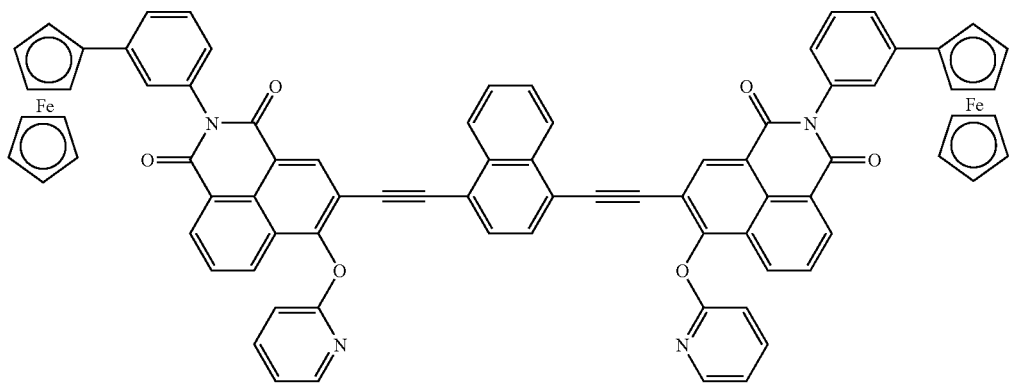
A-51
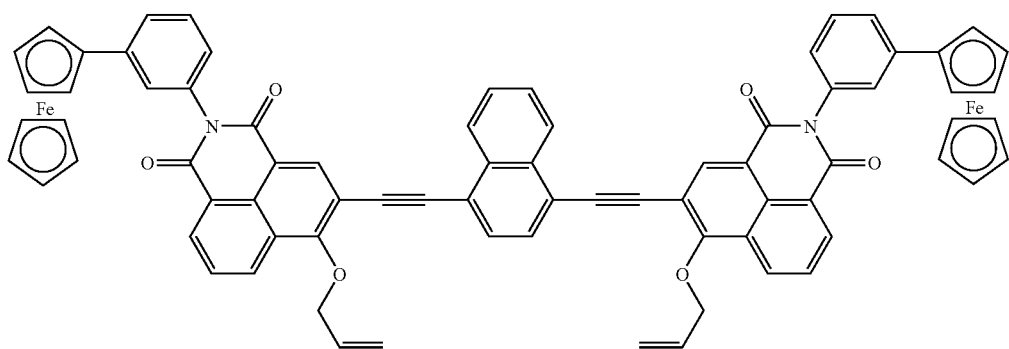
A-52
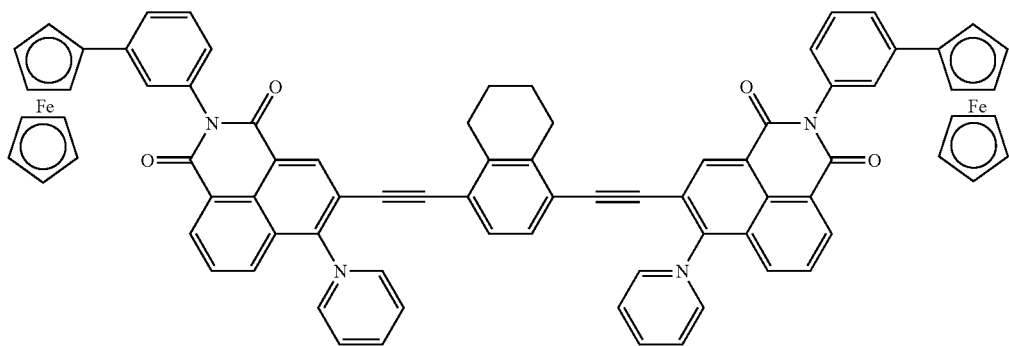
A-53
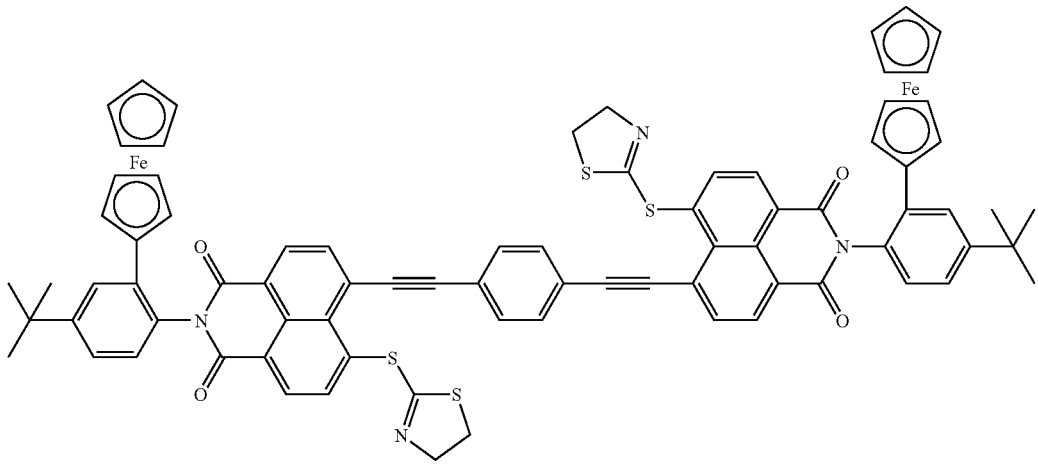
A-54

-continued
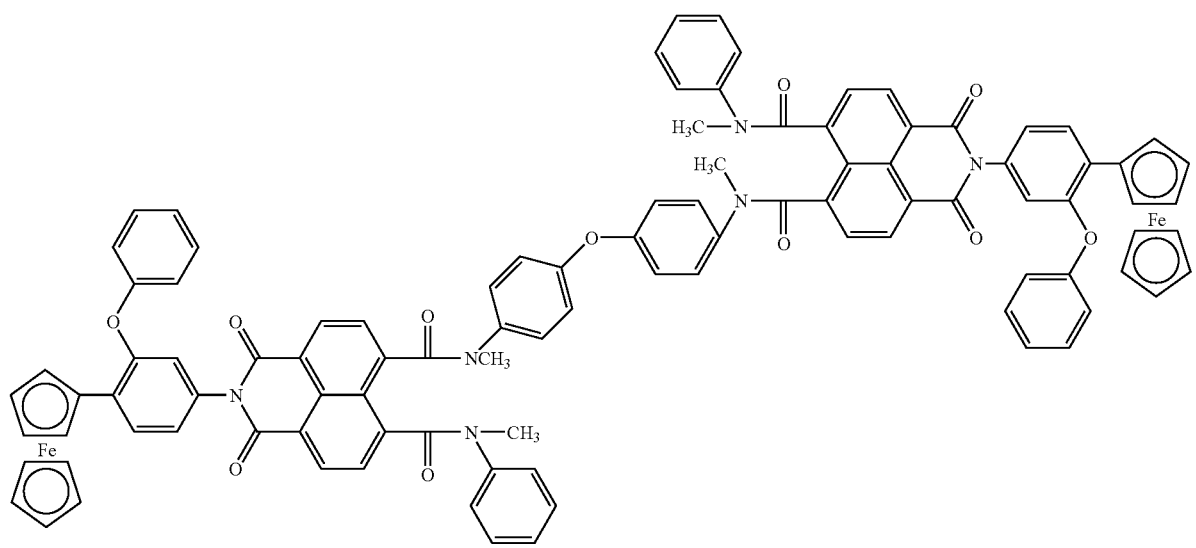
A-55
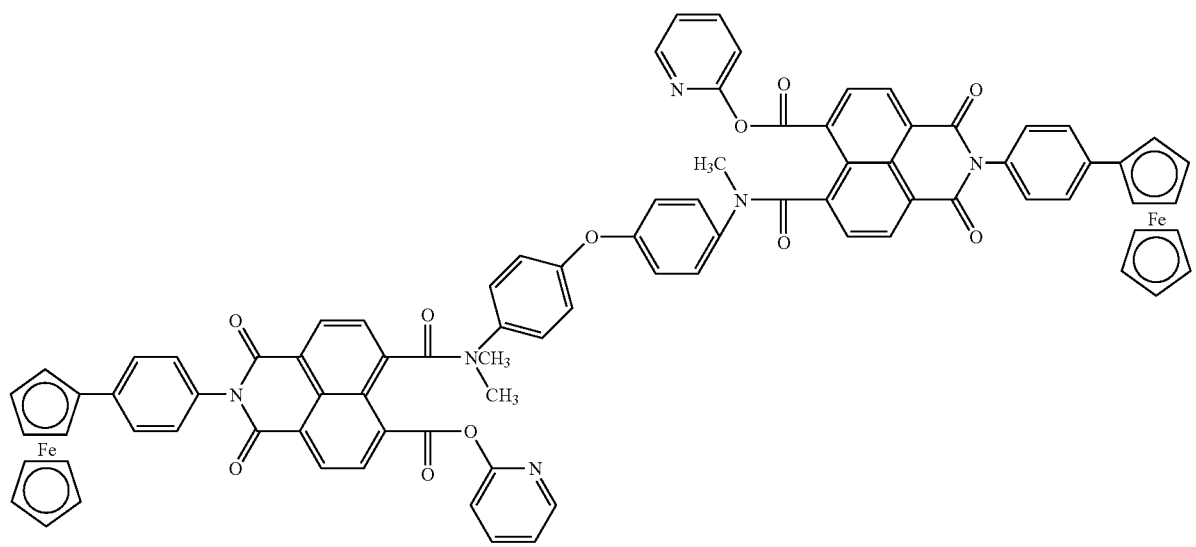
A-56
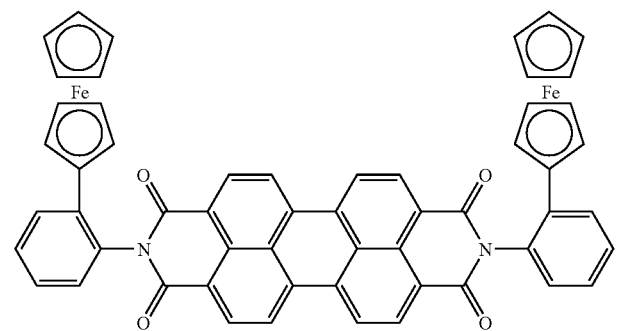
A-57
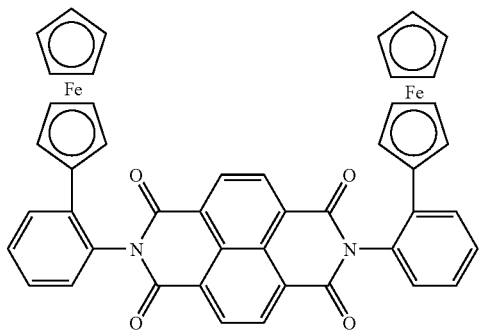
B-1

-continued
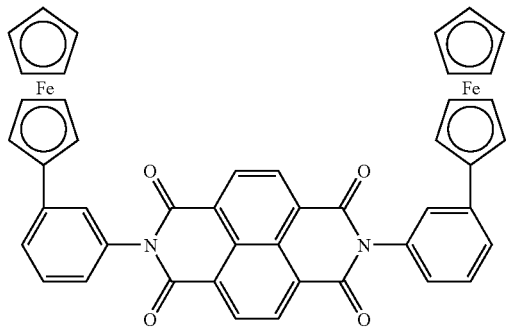
B-2
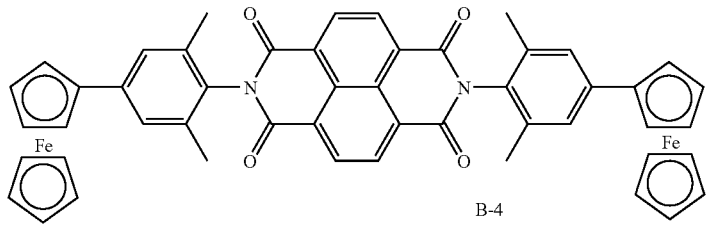
B-3
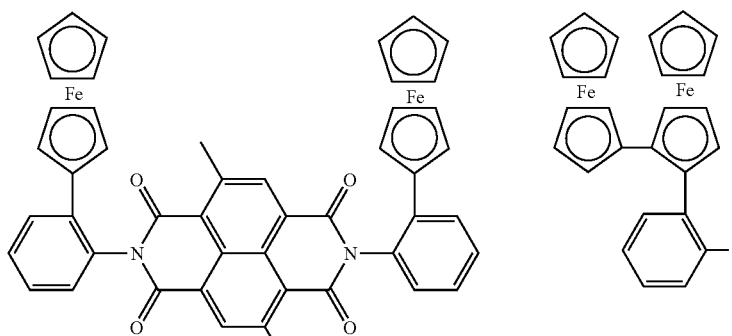
B-4
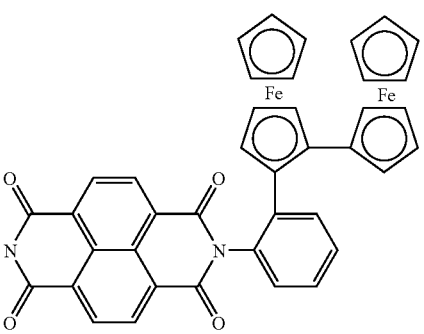
B-5
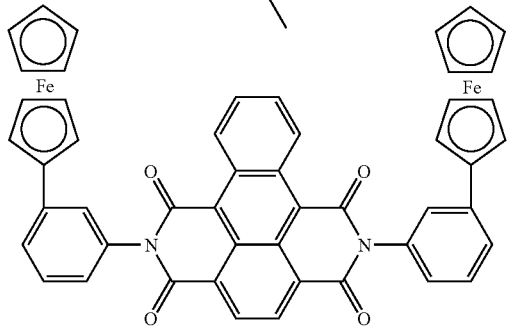
B-6
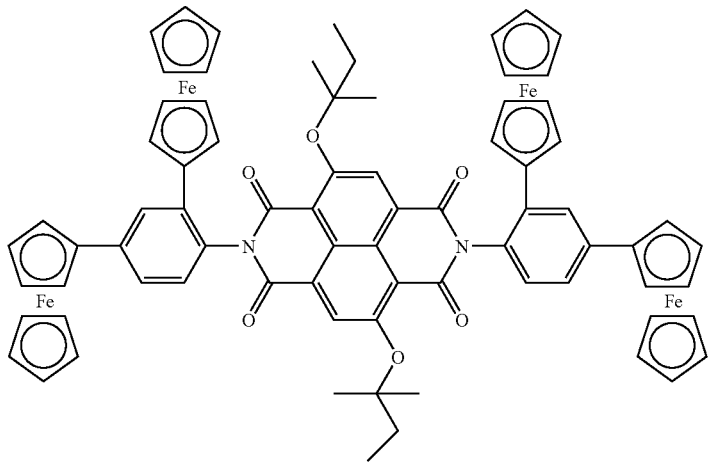
B-7

An imide compound of the present invention for use in an optical recording medium of the present invention can be produced, for example, by the following method. An imide compound represented by the formula (1) can be prepared, for example, by subjecting a carboxylic acid anhydride represented by the following general formula (22) and/or carboxylic acid obtained by hydrolysis thereof and an amine represented by the following general formula (23) to a reaction in the presence or absence of a solvent, if necessary, with heating.

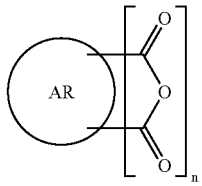
(22)

$A^m$-$NH_2$ (23)

wherein a ring AR, $A^m$, n and m are the same as those defined in the general formula (1).

Furthermore, a compound represented by the formula (2) can be prepared by subjecting a 1,8-naphthalenedicarboxylic acid anhydride represented by the following general formula (24) and/or carboxylic acid obtained by hydrolysis thereof and an amine represented by the general formula (25) and/or the general formula (26) and/or the general formula (27) below to a reaction in the presence or absence of a solvent, if necessary, with heating.

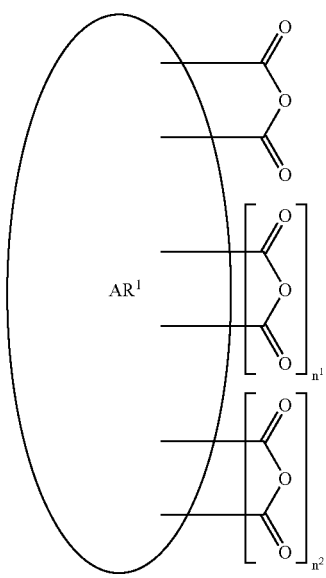
(24)

$A^{11}$-$NH_2$ (25)

$A^{21}$-$NH_2$ (26)

$A^{31}$-$NH_2$ (27)

wherein $AR^1$, $n^1$, $n^2$ and $A^{11}$ to $A^{31}$ are the same as those defined in the general formula (2).

Furthermore, a compound represented by the formula (3) can be prepared by subjecting a 1,8-naphthalene-dicarboxylic acid anhydride represented by the following general formula (28) and/or carboxylic acid obtained by hydrolysis thereof and an amine represented by the general formula (29) and/or the general formula (30) below to a reaction in the presence or absence of a solvent, if necessary, with heating.

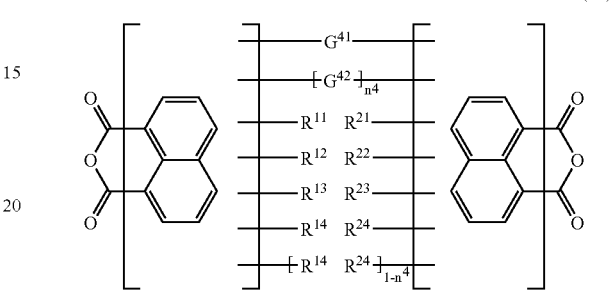
(28)

$R^1$—$NH_2$ (29)

$R^2$—$NH_2$ (30)

wherein $R^1$, $R^2$, $R^{11}$ to $R^{15}$, $R^{21}$ to $R^{25}$ and $n^4$ are the same as those defined in the formula (3).

Furthermore, a compound represented by the formula (4) can be prepared by subjecting a 1,8-naphthalene-dicarboxylic acid anhydride represented by the following general formula (31) and/or carboxylic acid obtained by hydrolysis thereof and an amine represented by the general formula (32) and/or the general formula (33) below to a reaction in the presence or absence of a solvent, if necessary, with heating.

(31)

$R^3$—$NH_2$ (32)

$R^4$—$NH_2$ (33)

wherein $R^3$, $R^4$, $R^{31}$ to $R^{33}$, $R^{41}$ to $R^{43}$ and $n^5$ are the same as those defined in the formula (4).

Furthermore, a compound represented by the formula (5) can be prepared by subjecting a 1,8-naphthalene-dicarboxylic acid anhydride represented by the following general formula (34) and/or carboxylic acid obtained by hydrolysis thereof and an amine represented by the general formula (35) below to a reaction in the presence or absence of a solvent, if necessary, with heating.

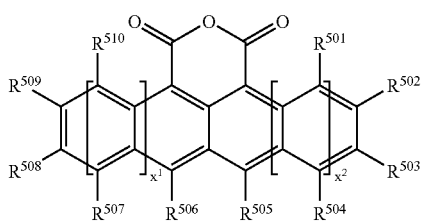

(5)

$R^5-NH_2$ (35)

wherein $R^{501}$ to $R^{510}$, $R^5$, $X^1$ and $X^2$ are the same as those defined in the general formula (5).

Furthermore, a compound represented by the general formula (6) can be prepared by subjecting a 1,8-naphthalene-dicarboxylic acid anhydride represented by the following general formula (36) and/or carboxylic acid obtained by hydrolysis thereof and an amine represented by the general formula (37) and/or the general formula (38) below to a reaction in the presence or absence of a solvent, if necessary, with heating.

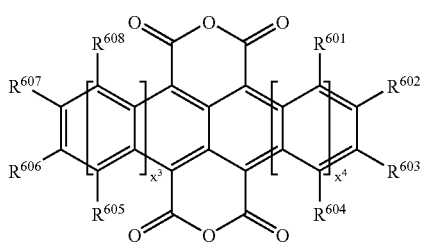

(36)

$R^{61}-NH_2$ (37)

$R^{62}-NH_2$ (38)

wherein $R^{601}$ to $R^{608}$, $R^{61}$, $R^{62}$, $X^3$ and $X^4$ are the same as those defined in the general formula (6).

Furthermore, a compound represented by the general formula (7) can be prepared by subjecting a 1,8-naphthalene-dicarboxylic acid anhydride represented by the following general formula (39) and/or carboxylic acid obtained by hydrolysis thereof and an amine represented by the general formula (40) and/or the general formula (41) below to a reaction in the presence or absence of a solvent, if necessary, with heating.

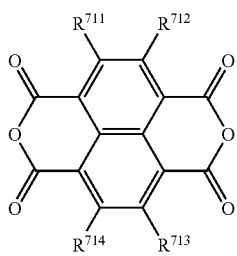

(39)

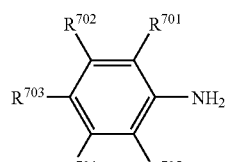

(40)

-continued

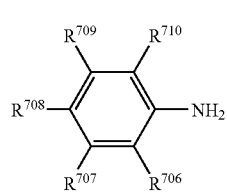

(41)

wherein $R^{701}$ to $R^{714}$ are the same as those defined in the general formula (7).

Furthermore, an imide compound represented by the general formula (8) can be prepared by subjecting a carboxylic acid anhydride represented by the following general formula (42) and/or carboxylic acid obtained by hydrolysis thereof and an amine represented by the general formula (43) to a reaction in the presence or absence of a solvent, if necessary, with heating.

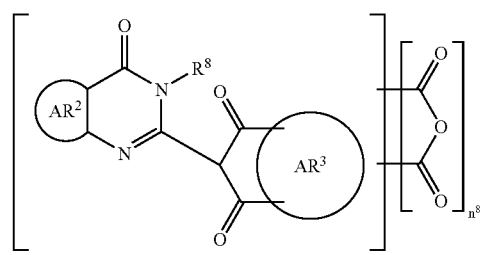

(42)

$B^b-NH_2$ (43)

wherein a ring $AR^2$, ring $AR^3$, $B^b$, $R^8$, and $n^8$ are the same as those defined in the general formula (8).

Furthermore, an imide compound represented by the general formula (9) can be prepared by subjecting a carboxylic acid anhydride represented by the following general formula (44) and/or a carboxylic acid obtained by hydrolysis thereof and an amine represented by the following general formula (45) to a reaction in the presence or absence of a solvent, if necessary, with heating.

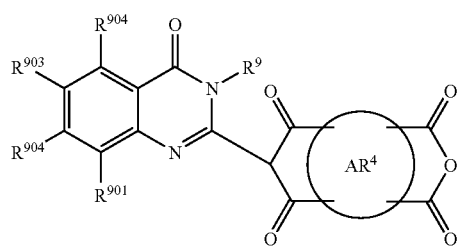

(44)

$R^{91}-NH_2$ (45)

wherein a ring $AR^4$, $R^{901}$ to $R^{904}$, and $R^9$ and $R^{91}$ are the same as those defined in the general formula (9).

Furthermore, an imide compound represented by the general formula (10) can be prepared by subjecting a carboxylic acid anhydride represented by the following general formula (46) and/or a carboxylic acid obtained by hydrolysis thereof and an amine represented by the following general formula (47) to a reaction in the presence or absence of a solvent, if necessary, with heating.

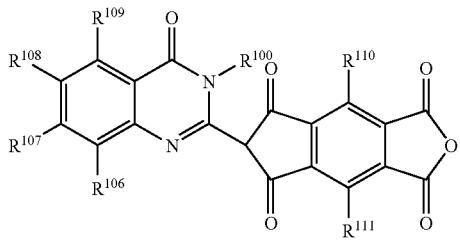
(46)

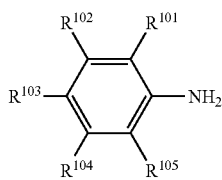
(47)

wherein $R^{100}$ to $R^{111}$ are the same as those defined in the general formula (10).

Furthermore, an imide compound represented by the general formula (11) can be prepared by subjecting a carboxylic acid anhydride represented by the following general formula (48) and/or carboxylic acid obtained by hydrolysis thereof and an amine represented by the following general formula (49) to a reaction in the presence or absence of a solvent, if necessary, with heating.

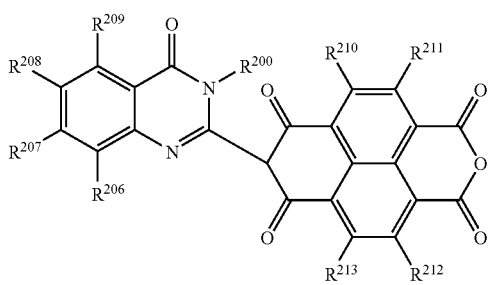
(48)

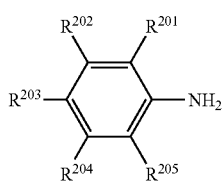
(49)

wherein $R^{200}$ to $R^{213}$ are the same as those defined in the general formula (11).

A reaction solvent to be used in producing the compounds of the general formulas (1) to (11) by the aforementioned synthesis is not particularly limited as long as an imide can be formed in the solvent. Preferable examples include organic carboxylic acids such as acetic acid, propionic acid, and butanoic acid; carbocyclic aromatic compounds such as 1-chloronaphthalene, monochlorobenzene, dichlorobenzene and trichlorobenzene, heterocyclic aromatic compounds such as quinoline and isoquinoline; amide series compounds such as N,N-dimethylformamide, N,N-dimethylacetoamide, N,N-dimethylimidazolidine-2-one, and N-methylpyrrolidine-2-one; and sulfur-containing compounds such as sulfolane. Furthermore, if necessary, metal salts such as zinc acetate and zinc chloride may be used. The reaction may be generally performed at a temperature of from 0 to 400° C., preferably from 50 to 300° C., more preferably from 100° C. to 250° C.

In an optical recording medium of the present invention, a recording layer is formed on a substrate. The recording layer contains at least one type of imide compound according to the present invention. In the optical recording medium of the present invention, write and read can be performed by recording laser and regenerating laser having a wavelength selected from the range of 300 to 900 nm. Of them, a recording laser and regenerating laser having a wavelength selected from the range of 390 to 430 nm, more preferable 400 to 410 nm provides a good C/N ratio. Furthermore, satisfactory stability to regeneration light and high-quality signal characteristics can be obtained.

A dye of the recording layer constituting an optical recording medium of the present invention is formed of substantially one or more imide compounds according to the present invention and may be mixed with a compound other than the aforementioned compounds having an absorption maximum within a wavelength of 290 to 690 nm and a large refractive index within a wavelength of 300 to 700 nm. Specific examples of such a compound include compounds of cyanine, squarylium, naphthoquinone, anthraquinone, tetra-pyra-porphyrazin, indophenol, pyrylium, thiopyrylium, azulenium, triphenyl methane, xanthene, indanthrene, indigo, thioindigo, merocyanine, thiazine, acridine, oxadine, dipyrromethene, oxazole, azaporphyrin, and porphyrin types; and may include a mixture of a plurality of compounds. These compounds are mixed in an amount of about 0.1 to 30% by weight.

To form a recording layer, to an imide compound of the present invention may be added, if necessary, additive such as a quencher, compound-thermolysing accelerator, ultraviolet-ray absorbing agent, adhesive agent, endothermic or endothermically decomposing compound, or a polymer for improving dissolution, or a compound having such an effect can be introduced as a substituent of an imide compound according to the present invention.

Specific examples of a quencher preferably include metal complexes such as acetylacetonates, bisdithiols such as bisdithio-α-diketone or bisphenyldithiols, thiocatechonales, salicylaldehydeoxims, and thiobisphenolates. Also amines may be preferable.

A compound-thermolysing accelerator is not particularly limited as long as it can be verified by weight loss analysis (thermogravimetry) that it may accelerate thermolysis of a compound. For example, metal containing compounds such as metallic anti-knocking agents, metallocene compounds, and metal acetylacetonato complexes may be mentioned.

As an endothermic or endothermically decomposing compound, compounds described in Japanese Patent Laid-Open No. 10-291366 or substituted compounds described in the publication may be mentioned.

Each of various types of quencher, compound-thermolysing accelerators, and endothermic or endothermically decomposing compounds mentioned above may be used singly or in a mixture of two or more elements, if necessary.

Furthermore, if necessary, additional substances such as a binder, leveling agent, and defoaming agent may be added. Furthermore, preferable examples of a binder include polyvinyl alcohol, polyvinyl pyrrolidone, nitrocellulose, cellulose acetate, ketone resin, acrylic resin, polystyrene resin, urethane resin, polyvinyl butyral, polycarbonate, and polyolefin.

When a recording layer is formed on a substrate, other layers formed of an inorganic substance and a polymer, respectively, may be provided on the substrate in order to improve solvent-resistance, reflectivity, and recording sensitivity.

Although the content of an imide compound according to the present invention in the recording layer may be arbitrarily set as long as it attains write and read, usually the content is 30% or more and preferably 60% or more. Incidentally, it is also preferable that the content be substantially 100%.

Examples of providing a recording layer include coating methods such as a spin coating, spraying, casting, slide coating, curtain coating, extrusion, wire coating, gravure coating, spreading, roller coating, knife coating, and soaking; sputtering method; chemical vapor deposition method; and vacuum vapor deposition method; however, a spin coating method is simple and thus preferable.

When a coating method such as a spin coating method is used, a coating solution in which an imide compound according to the present invention is dissolved or dispersed in a solvent in an amount of 1 to 40% by weight, preferably 3 to 30% by weight, is used. In this case, it is preferable to choose as a solvent that will not damage a reflecting layer. Examples of a solvent for use in coating include alcohol solvents such as methanol, ethanol, isopropyl alcohol, octafluoro pentanol, allyl alcohol, methyl cellosolve, ethyl cellosolve, and tetrafluoro propanol; aliphatic or alicyclic hydrocarbon solvents such as hexane, heptane, octane, decane, cyclohexane, methylcyclohexane, ethylcyclohexane, and dimethylcyclohexane; aromatic hydrocarbon solvents such as toluene, xylene, and benzene; halogenated hydrocarbon solvents such as carbon tetrachloride, chloroform, tetrachloroethane, and dibromoethane; ether solvents such as diethyl ether, dibutyl ether, diisopropyl ether, and dioxane; ketone solvents such as acetone, 3-hydroxy-3-methyl-2-butanone; ester solvents such as ethyl acetate, and methyl lactate; and water. These may be used singly or in combination.

Incidentally, if necessary, a compound for a recording layer may be used by dispersing it in a polymer thin film.

In the case where a solvent not damaging a substrate is not selected, a sputter method, chemical vapor deposition method or vacuum vapor deposition method may be effective.

The film thickness of a recording layer is 10 to 1,000 nm and preferably 20 to 300 nm. When the film thickness of the recording layer is set thinner than 10 nm, thermal diffusion may become large. As a result, write may not be performed or distortion of a recording signal may occur. In addition, signal amplitude sometimes decreases. On the other hand, when the film thickness is thicker than 1,000 nm, the reflectivity decreases and regeneration signal characteristics sometimes decrease.

Subsequently, on the recording layer, a reflecting layer preferably having a thickness of 50 to 300 nm is formed. To increase the reflectivity and adhesiveness, a reflection-amplification layer and adhesive layer may be provided between the recording layer and the reflecting layer. As a material for the reflecting layer, metals exhibiting a high reflectivity at a wavelength of regeneration light such as Au, Al, Ag, Cu, Ti, Cr, Ni, Pt, Ta and Pd can be used singly or in the form of an alloy. Of them, Au, Ag and Al are preferable as a material for the reflecting layer since they have high reflectivities. When write and read is performed by a blue laser, Al or Ag is preferable. Other than this, the following elements may be contained. For example, metals or semi metals such as Mg, Se, Hf, V, Nb, Ru, W, Mn, Re, Fe, Co, Rh, Ir, Zn, Cd, Ga, In, Si, Ge, Te, Pb, Po, Sn, and Bi may be mentioned. A material containing Ag or Al as a main component is preferable since a reflecting layer exhibiting a high reflectivity can be easily obtained. Alternatively, a low-reflectivity thin film and a high-reflectively thin film are formed of non-metal materials and they are alternately layered to form a multi-layered form, which may be used as a reflecting layer.

Examples of a method for forming a reflecting layer include methods of sputtering, ion-plating, chemical vapor deposition, and vacuum vapor deposition. Further on a substrate or under a reflecting layer, an intermediate layer and an adhesive layer of known inorganic or organic substances may be provided in order to improve the reflectivity, recording characteristics, stability to regeneration light, and adhesiveness.

A material for a protecting layer formed on the reflecting layer is not particularly limited as long as it can protect the reflecting layer from external force. Examples of an inorganic substance include $SiO_2$, $Si_3N_4$, $MgF_2$, AlN, $SnO_2$, and $TiO_2$. Examples of an organic substance include thermoplastic resin, thermosetting resin, electron beam curing resin, and ultraviolet-ray curing resin. In the case of a thermoplastic resin or thermosetting resin, a resin is dissolved in an appropriate solvent to prepare a coating solution and thereafter the coating solution is applied and dried to form a protecting layer. An ultraviolet-ray curing resin may be directly coated or after it is dissolved in an appropriate solvent to prepare a coating solution, and the coating solution is coated and then ultraviolet-ray is applied to cure, thereby forming a protecting layer. As an ultraviolet-ray curing resin, acrylate resins such as urethane acrylate, epoxy acrylate, and polyester acrylate may be used. These materials may be used singly or in a mixture and may be formed into a single layer or a multi-layer film.

As a method of forming a protecting layer, the same methods as employed in forming a recording layer, that is, a coating method such as a spin coating and casting; sputtering method, and a chemical vapor deposition method may be used. Of them, a spin coating method is preferable.

The film thickness of a protecting layer generally falls within the range of 0.1 μm to 100 μm; however, in the present invention, it falls within the range of 3 to 30 μm, and more preferably 5 to 20 μm.

Further on the protecting layer, a label, bar cord or the like may be printed.

Furthermore, on the reflecting layer surface, a protecting sheet or a substrate may be adhered or two optical recording media may be adhered by making reflecting layer surfaces to face inward each other.

On the mirror surface of a substrate, an ultraviolet-ray curing resin, an inorganic thin film and the like may be formed for the protection of the surface, prevention of dust deposition, or the like.

When an optical recording medium as shown in FIG. 4 is prepared, a reflecting layer of, preferably, 1 to 300 nm thick, is formed on a substrate. To improve a reflectivity or adhesiveness, a reflection-amplification layer and an adhesion layer may be provided between the recording layer and the reflecting layer. As a material for the reflecting layer, metals exhibiting a high reflectivity at a wavelength of regeneration light, metals such as Al, Ag, Ni and Pt may be used singly or in the form of an alloy. Of them, Ag and Al are preferable as a material for the reflecting layer since they have high reflectivities. Besides this, the following elements may be contained, if necessary. For example, metals or semi metals such as Mg, Se, Hf, V, Nb, Ru, W, Mn, Re, Fe, Co, Rh, Ir, Zn, Cd, Ga, In, Si, Ge, Te, Pb, Po, Sn, Bi, Au, Cu, Ti, Cr, Pd, and Ta may be mentioned. A metal material containing Ag or Al as a main component and readily providing a reflecting layer exhibiting a high reflectivity is preferable. It is also possible that a multi-layer film is formed by alternately stacking a low-reflectivity thin film and a high-reflectivity thin film formed of non-metal materials and used as a reflecting layer.

Examples of a method for forming a reflecting layer include methods of sputtering, ion-plating, chemical vapor deposition, and vacuum vapor deposition. Further on a substrate or under a reflecting layer, an intermediate layer and an adhesive layer of known inorganic or organic substances may be provided in order to improve the reflectivity, recording characteristics, stability to regeneration light, and adhesiveness.

Next, when a recording layer is formed on a reflecting layer, a layer formed of an inorganic substance or a polymer may be provided on the reflecting layer in order to improve solvent-resistance, reflectivity, and recording sensitivity.

Although the content of an imide compound according to the present invention in the recording layer may be arbitrarily set as long as it attains write and read, usually the content is 30% by weight or more and preferably 60% by weight or more. Incidentally, it is also preferable that the content is substantially 100% by weight.

Examples of providing a recording layer include coating methods such as a spin coating, spraying, casting, slide coating, curtain coating, extrusion, wire coating, gravure coating, spreading, roller coating, knife coating, and soaking; sputtering method; chemical vapor deposition method; and vacuum vapor deposition method; however, a spin coating method is simple and thus preferable.

When a coating method such as a spin coating method is used, a coating solution in which an imide compound according to the present invention is dissolved or dispersed in a solvent in an amount of 1 to 40% by weight, preferably 3 to 30% by weight, is used. In this case, it is preferable to choose as a solvent that will not damage a reflecting layer. Examples of a solvent for use in coating include alcohol solvents such as methanol, ethanol, isopropyl alcohol, octafluoro pentanol, allyl alcohol, methyl cellosolve, ethyl cellosolve, and tetrafluoro propanol; aliphatic or alicyclic hydrocarbon solvents such as hexane, heptane, octane, decane, cyclohexane, methylcyclohexane, ethylcyclohexane, and dimethylcyclohexane; aromatic hydrocarbon solvents such as toluene, xylene, and benzene; halogenated hydrocarbon solvents such as carbon tetrachloride, chloroform, tetrachloroethane, and dibromoethane; ether solvents such as diethyl ether, dibutyl ether, diisopropyl ether, and dioxane; ketone solvents such as acetone, 3-hydroxy-3-methyl-2-butanone; ester solvents such as ethyl acetate, and methyl lactate; and water. These may be used singly or in combination.

Incidentally, if necessary, a compound for a recording layer may be used by dispersing it in a polymer thin film.

In the case where a solvent not damaging a reflecting layer is not selected, sputtering method, chemical vapor deposition method or vacuum vapor deposition method may be effective.

The film thickness of a recording layer is 1 to 1,000 nm and preferably 5 to 300 nm. When the film thickness of a recording layer is set thinner than 1 nm, write may not be performed or distortion of a recording signal may occur. In addition, signal amplitude sometimes decreases. On the other hand, when the film thickness is thicker than 1,000 nm, the reflectivity decreases and regeneration signal characteristics sometimes decrease.

A material for a protecting layer formed on a recording layer is not particularly limited as long as it can protect the recording layer from external adverse effects such as external force and atmosphere. Examples of an inorganic substance include $SiO_2$, $Si_3N_4$, $MgF_2$, AlN, $SnO_2$, and $TiO_2$. Examples of an organic substance include thermoplastic resin, thermosetting resin, electron beam curing resin, and ultraviolet-ray curing resin. In a thermoplastic resin and thermosetting resin, a resin is dissolved in an appropriate solvent to prepare a coating solution and thereafter the coating solution is applied and dried to form a protecting layer. An ultraviolet-ray curing resin may be directly coated or after it is dissolved in an appropriate solvent to prepare a coating solution, and the coating solution is coated and then ultraviolet-ray is applied to cure, thereby forming a protecting layer. As an ultraviolet-ray resin, acrylate resins such as urethane acrylate, epoxy acrylate, and polyester acrylate may be used. These materials may be used singly or in a mixture and may be formed into a single layer or a multi-layer film.

As a method of forming a protecting layer, the same methods as employed in forming a recording layer, that is, a coating method such as a spin coating and casting; sputtering method; and a chemical vapor deposition method may be used. Of them, a spin coating method is preferable.

The film thickness of a protecting layer generally falls within the range of 0.01 to 1,000 µm; may be within the range of 0.1 to 100 µm, and further 1 to 20 µm, depending on conditions.

Furthermore, on the substrate surface, a protecting sheet or a reflecting layer may be adhered or two optical recording media may be adhered by making substrate surfaces to face inward each other.

On the protecting layer side, an ultraviolet-ray curing resin, an inorganic thin film and the like may be formed for the protection of the surface, prevention of dust deposition, or the like.

In an optical recording medium according to the present invention, to protect the entire medium, a protecting unit such as a case for protecting a disk may be provided, as is seen in a flexible disk and photomagnetic disk. As a material, a plastic and a metal such as aluminum may be used.

As a material for a substrate, any material capable of transmitting the wavelength of recording light and regeneration light may be basically used. As a material for a support substrate, in consideration of the case where a bluish-violet laser is applied through the substrate 11 as shown in FIG. 5, transparent materials including polymer materials such as acrylic resin, polyethylene resin, polycarbonate resin, polyolefin resin, and epoxy resin; and inorganic materials such as glass, may be used. On the other hand, in the case where a laser is applied from the side of the light transmission layer 15 opposite to the substrate 11' as is in the structure shown in FIG. 6, a material for the substrate needs not satisfy the optical requirements and may be chosen from a wide variety of materials. In view of mechanical characteristics required for a substrate or substrate productivity, a material applicable to injection molding or cast molding is preferable. Examples of such a material include an acrylic resin, polycarbonate resin and polyolefin. These substrate materials may be formed into a disk as a substrate by injection molding or the like.

Furthermore, if necessary, on the surface of these substrates, guide grooves and/or prepits of a submicron order may be spirally or concentrically formed. These guide grooves and prepits are preferably formed at the time the substrate is formed and may be formed by injection molding using a stamper or a thermal transfer method using a photopolymer. Guide grooves and/or prepits may be formed in the light transmission layer 15' in FIG. 6 and may be provided in the same method mentioned above. The pitch and depth of a guide groove in the case of HD-DVD-R where recording is performed with a higher density than a DVD, are preferably selected from a pitch range of 0.25 to 0.80 μm and a depth range of 20 to 150 nm.

Generally, in the case of an optical disk, a disk having a thickness of about 1.2 mm and a diameter of about 80 to 120 mm may be used and a hole of about 15 mm diameter may be formed at the center.

The laser having a wavelength of 300 to 500 nm defined in the present invention is not particularly limited. Examples of the laser include dye lasers which can be selected from a wide wavelength range of visible light; gas lasers such as a nitrogen laser (337 nm); ion lasers such as a helium cadmium laser of 445 nm wavelength and an argon laser of 457 nm or 488 nm wavelength; and semiconductor lasers such as a GaN laser of 400 to 410 wavelength, infrared lasers using Cr-doped $LiSnAlF_6$ of 860 nm wavelength and oscillating the second harmonic of 430 nm, and visible-light semiconductor lasers having a wavelength of 415 nm and 425 nm. In the present invention, a laser can be appropriately selected depending upon the wavelength to which the recording layer for performing write and read can respond. High-density recording and regeneration can be made at a single wavelength or a plurality of wavelengths selected from the lasers mentioned above.

Examples of the present invention will be described below, however, the present invention will not limited to these examples.

SYNTHETIC EXAMPLE 1

Synthesis of a Compound Represented by Reference Number A-57

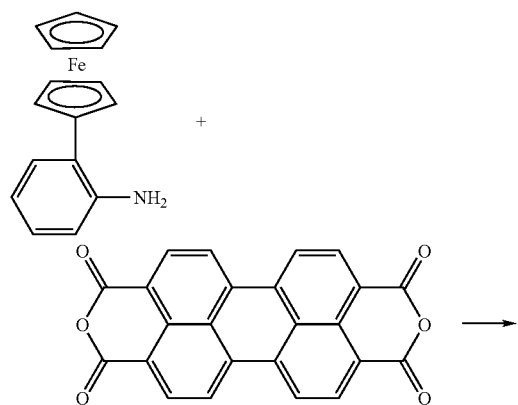

(A-57)

-continued

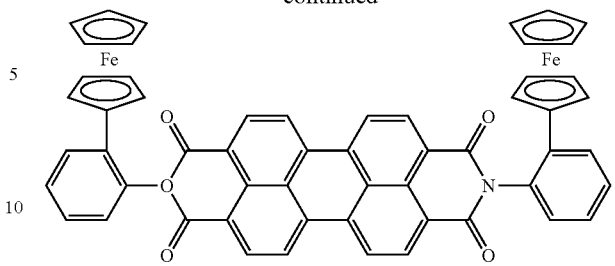

22 parts of 2-ferrocenyl aniline, 15 parts of perylene tetracarboxylic acid dianhydride, 6 parts of anhydrous zinc acetate, and 600 parts of quinoline were added and reacted at 220° C. for 3 hours. The reaction mass was cooled to room temperature and discharged in 4,000 parts of methanol. After filtration, the filtrated matter was washed with methanol and redissolved in chloroform. The solution was dried over anhydrous magnesium sulfate and subsequently subjected to silica gel chromatography (using a developing solution: chloroform/ethyl acetate=9/1) to fractionate a target material. After condensation, the obtained solid matter is subjected to sludging with methanol, filtrated and dried to obtain 10 parts of a compound, which was confirmed as a compound represented by reference number A-57 by mass spectrometry.

SYNTHETIC EXAMPLE 2

Synthesis of a Compound Represented by Reference Number B-69

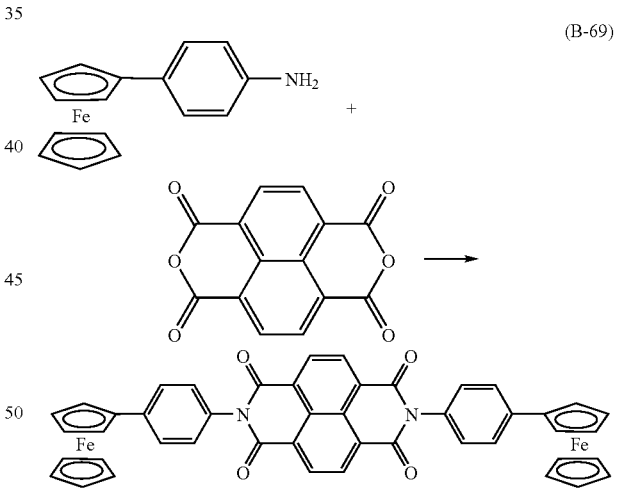

(B-69)

28 parts of 4-ferrocenyl aniline, 13 parts of 1,4,5,8-naphthalenetetracarboxylic acid dianhydride, 300 parts of N,N-dimethylimidazolidine-2-one, and 30 parts of toluene, were added and reacted at 150° C. for 5 hours. The reaction mass was cooled to room temperature and discharged in 3,000 parts of water. After filtration, the filtrated matter was washed with water and dried. The solid matter was subjected to silica gel chromatography (using chloroform as a developing solution) to fractionate a target material. After condensation, recrystallization and drying steps were taken to obtain 6 parts of a compound, which was confirmed as a compound represented by reference number B-69 by mass spectrometric analysis.

SYNTHETIC EXAMPLE 3

Synthesis of a Compound Represented by Reference Number B-70

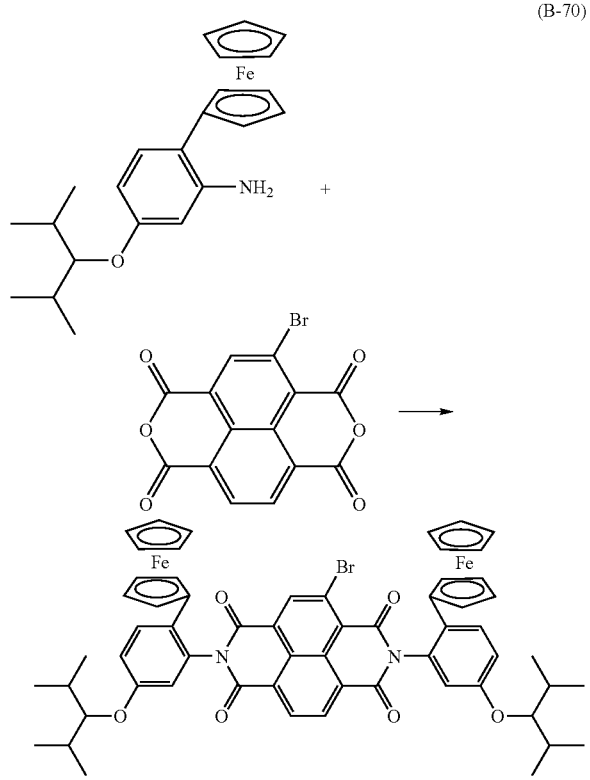

78 parts of 2-ferrocenyl-5-(2',4'-dimethylpentane-3'-yl) oxyaniline, 34 parts of 2-bromo-1,4,5,8-naphthalenetetra-carboxylic acid dianhydride, 300 parts of acetic acid, were added and reacted at 120° C. for 6 hours. The reaction mass was cooled to room temperature and discharged in 3,000 parts of water. After filtration, the filtrated matter was washed with water and dried. The solid matter was subjected to silica gel chromatography (using chloroform as a developing solution) to fractionate a target material. After condensation, recrystallization and drying steps were taken to obtain 11 parts of a compound, which was confirmed as a compound represented by reference number B-70 by mass spectrometry.

SYNTHETIC EXAMPLE 4

Synthesis of a Compound Represented by Reference Number C-77

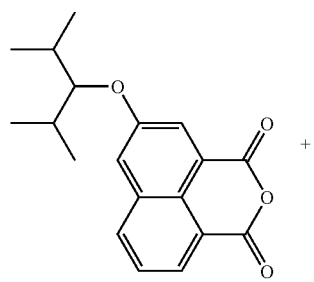

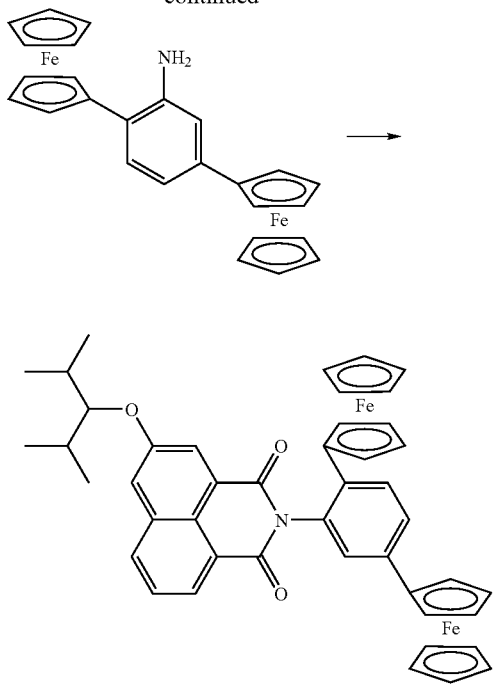

32 parts of 2,5-diferrocenyl aniline, 46 parts of 3-(2',4'-dimethyl-pentane-3'-yl)oxy-1,8-naphthalic anhydride, and 600 parts of N,N-dimethyl-imidazolidine-2-one, were added and reacted at 180° C. for 6 hours. The reaction mass was cooled to room temperature and discharged in 3,000 parts of water. After filtration, the filtrated matter was washed with water and dried. The solid matter was subjected to silica gel chromatography (using chloroform as a developing solution) to fractionate a target material. After condensation, recrystallization and drying steps were taken to obtain 45 parts of a compound, which was confirmed as a compound represented by reference number C-77 by mass spectrometry.

SYNTHETIC EXAMPLE 5

Synthesis of a Compound Represented by Reference Number D-1

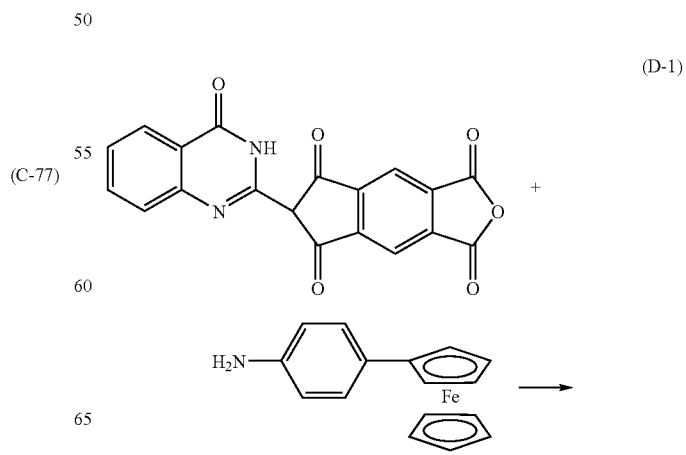

-continued

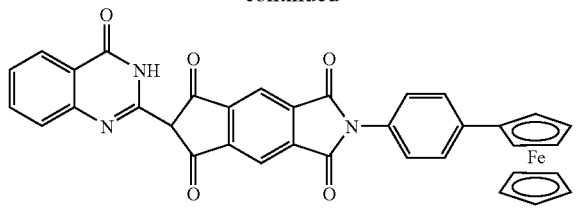

To a mixture containing 36 parts of 6-(4-oxo-3,4-dihydroquinazoline-2-yl)-2-oxa-s-indaceno-1,3,5,7-tetraone, 10 parts of 1,3-dimethylimidazolidine-2-one, and 1 part of toluene, 28 parts of 4-ferrocenylaniline was added and the resultant mixture was stirred at 150° C. for 8 hours. The reaction mass was cooled to room temperature, and the precipitated solid matter was filtrated and washed with water and methanol to obtain 41 parts of a light-yellow solid matter, which was confirmed as a compound represented by reference number D-1 by mass spectrometry.

EXAMPLE 1

On a disk-form substrate made of polycarbonate resin and having an outer diameter of 120 mmφ and a thickness of 0.6 mm with a continuous guide groove (track pitch: 0.74 μm) formed therein, a compound represented by reference number B-69 was deposited by vacuum vapor deposition method up to a thickness of 70 nm, thereby forming a recording layer.

On the recording layer, silver was sputtered by use of a sputter apparatus (CDI-900) manufactured by Balzers to obtain a reflecting layer 100 nm thick. As a sputter gas, argon gas was used. Sputter was performed under the conditions: a sputter power of 2.5 kW and a sputter gas pressure of 1.33 Pa ($1.0 \times 10^{-2}$ Torr).

Further on the reflecting layer, an ultraviolet ray curing resin "SD-1700" (manufactured by Dai-Nippon Ink Chemical Industries Co., Ltd.) was spin-coated and thereafter, irradiated with ultraviolet rays to obtain a protecting layer of 5 μm thick. Further on the protecting layer, an ultraviolet ray curing resin "DeSolite KZ-8681" (manufactured by JSR Corporation) was spin coated and thereafter a polycarbonate resin substrate which was the same as the substrate mentioned above and had no guide groove was mounted. Both substrates were adhered by ultraviolet irradiation to form an optical recording medium.

With respect to the optical recording medium having the recording layer formed in the manner mentioned above, the following tests were performed.

Recording was performed by an evaluation machine on which a blue laser head of 403 nm wavelength having a numeric aperture of 0.65 is installed, at a recording frequency of 9.7 MHz, a recording laser power of 8.0 mW, a line speed of 9.0 m/s, and the minimum pit length of 0.30 μm. Fine shape pits were regularly formed with a high density. After recording, regeneration was performed by the same evaluation machine at a regeneration laser power of 0.6 mW and a line speed of 9.0 m/s. As a result, pits were successfully read. Although regeneration was repeatedly performed for 1,000 times or more, pits were able to be read out. The disk was excellent in stability to regeneration light. The C/N ratio was 50 dB or more.

Furthermore, a light fastness test was performed by applying a Xe light of 40,000 lux. Even after 100 hours from start of a test, pits were able to be read. Assuming that the light absorption amount of a recording layer before the test was 100%, the light absorption amount after light irradiation for 100 hours changed by as low as 10% or less. Good results were obtained.

Furthermore, a humidity and heat resistance test was performed by allowing an optical recording medium to stand alone under an atmosphere of 85% RH and 80° C. Even after 100 hours from start of the test, pit was successfully read.

EXAMPLE 2

An optical recording medium was prepared in the same manner as in Example 1 except that a recording layer was formed by using a compound represented by reference number D-1 in place of a compound represented by reference number B-69 and write and read were performed in the same manner as in Example 1. As a result, pits of a good shape were formed and successfully read. Stability to regeneration light was excellent and the C/N ratio was 50 dB or more.

Pits were able to be read after light fastness and humidity and heat resistance were tested.

EXAMPLE 3

An optical recording medium was prepared in the same manner as in Example 1 except that a recording layer was formed by using a compound represented by reference number A-57 in place of a compound represented by reference number B-69 and write and read were performed in the same manner as in Example 1. As a result, pits of a good shape were formed and successfully read. Stability to regeneration light was excellent and the C/N ratio was 50 dB or more.

Pits were able to be read after light fastness and humidity and heat resistance were tested.

EXAMPLES 4-317

Optical recording media were prepared in the same manner as in Example 1 except that recording layers were formed by using compounds represented by reference numbers A-1 to 56, B-1 to 68, C-1 to 76 and D-2 to 115 in place of a compound represented by reference number B-69 and write and read were performed in the same manner as in Example 1. As a result, pits of good shapes were formed and read. Stability to regeneration light was excellent. Pits were able to be read after light fastness and humidity and heat resistance were tested.

EXAMPLE 318

For a recording layer, 0.2 g of a compound (B-70) listed in Table 1 was dissolved in 10 ml of 2,2,3,3-tetrafluoropropanol, to prepare a dye solution. As a substrate, a disk made of a polycarbonate resin having an outer diameter of 120 mmφ and a thickness of 0.6 mm with a continuous guide groove (track pitch: 0.74 μm) was used. On the substrate, the dye solution was spin coated at a rotation speed of 1,500 $min^{-1}$ and dried at 70° C. for 3 hours to form a recording layer. On the recording layer, silver was sputtered by using a sputter apparatus (CDI-900) manufactured by Balzers to obtain a reflecting layer of 100 nm thick. As a sputter gas, argon gas was used. Sputter was performed under the conditions: a sputter power of 2.5 kW and a sputter gas pressure of 1.33 Pa ($1.0 \times 10^{-2}$ Torr).

Further on the reflecting layer, an ultraviolet ray curing resin "SD-1700" (manufactured by Dai-Nippon Ink Chemical Industries Co., Ltd.) was spin-coated and thereafter, irradiated with ultraviolet rays to obtain a protecting layer of 5 µm thick. Further on the protecting layer, an ultraviolet ray curing resin "DeSolite KZ-8681" (manufactured by JSR Corporation) was spin coated and then a polycarbonate resin substrate which was the same as the substrate mentioned above and had no guide groove was mounted. Both substrates were adhered by ultraviolet irradiation to form an optical recording medium.

Read and write were performed in the same manner as in Example 1. Good shaped pits were formed and successfully read. Regeneration light stability was excellent.

Pits were able to be read after light fastness and humidity and heat resistance were tested.

EXAMPLE 319

A recording layer was formed as in Example 318 except for using a compound represented by reference number C-77 in place of a compound represented by reference number B-70. Except for the above, an optical recording medium was prepared in the same manner as in Example 1, and write and read were performed in the same manner as in Example 1. Read and write was performed in the same manner as in Example 1. Pits of a good shaped were formed and successfully read. Stability to regeneration light was excellent.

Pits were able to be read after light fastness and humidity and heat resistance were tested.

EXAMPLE 320

A recording layer was formed as in Example 318 except for using a compound represented by reference number E-1 in place of a compound represented by reference number B-70. Except for the above, an optical recording medium was prepared in the same manner as in Example 1, and write and read were performed in the same manner as in Example 1. Pits of a good shape were formed and successfully read. Stability to regeneration light was excellent.

Pits were able to be read after light fastness and humidity and heat resistance were tested.

COMPARATIVE EXAMPLE 1

An optical recording medium was prepared in the same manner as in Example 318 except that a compound represented by a formula (a)

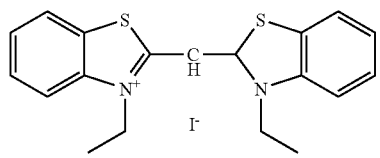

(a)

was used in place of a compound represented by reference number B-70, and write and read were performed in the same manner as in Example 1. It was difficult to read data since the C/N ratio was as low as 20 dB or less.

COMPARATIVE EXAMPLE 2

An optical recording medium was prepared in the same manner as in Example 1 except that a compound represented by a formula (b)

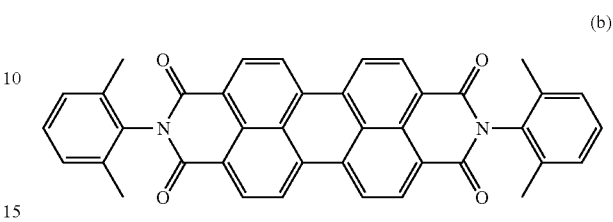

(b)

was used in place of a compound represented by reference number B69, and write and read were performed in the same manner as in Example 1. A signal ratio decreased, that is, the C/N ratio was as low as 40 dB or less. The C/N ratio of less than 45 dB was a low signal ratio.

As a result of a light fastness test, read becomes difficult after 100 hours from initiation of irradiation. Assuming that the light absorption amount of a recording layer before the test was 100%, the light amount after 100 hours from light irradiation changed by as large as 70% or more. A significant deterioration was observed.

As described as in Examples 1 to 320, the optical recording medium according to the present invention is capable of recording and regenerating data in a blue laser wavelength region and has excellent recording properties.

Form this, a recording layer containing a compound having a structure defined by the present invention is capable of writing signal data by a laser beam selected from a wavelength region of 300 to 900 nm. The optical recording medium of the present invention can be applied to that using a laser beam selected from the wavelength region to 300 to 900 nm for read and write.

INDUSTRIAL APPLICABILITY

According to the present invention, it is possible to provide an optical recording medium, which attracts attention very much as a high-density recording medium, capable of recording and regenerating data by a laser having a wavelength of 300 to 900 nm, in particular, a bluish-violet laser having a wavelength of 400 to 410 nm.

What is claimed is:

1. An imide compound having a quinazoline-4-on residue represented by a general formula (9) as one of tautomeric structures:

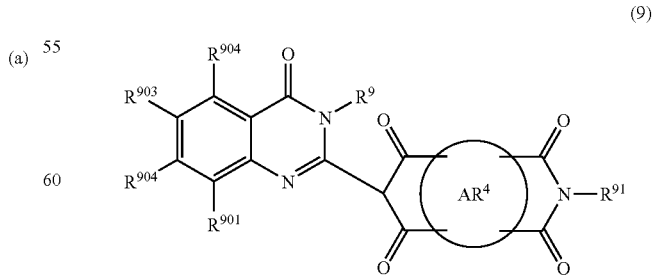

(9)

wherein a ring $AR^4$ represents a substituted or unsubstituted aromatic ring residue or a residue formed by combining two or more aromatic ring residues via one or more linking groups; $R^9$ represents hydrogen, substituted or unsubstituted alkyl, substituted or unsubstituted aralkyl, or substituted or unsubstituted aromatic ring; $R^{901}$ to $R^{904}$ each independently represent a hydrogen or halogen atom; a group selected from nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, heteroarylthio, or substituted or unsubstituted metallocenyl; or, in a combination of $R^{901}$ to $R^{904}$, two or more substituents selected from the combination may independently combine via a linking group to form a cyclic structure together with carbon atoms to which they are attached; and $R^{91}$ represents a group in which a substituted or unsubstituted metallocenyl group bonds to the nitrogen atom of the imide group via a bivalent linking group composed of at least one selected from a substituted or unsubstituted bivalent aromatic ring.

2. The imide compound according to claim 1, wherein the imide compound having a quinazoline-4-on residue is represented by a general formula (10) as one of the tautomeric structures:

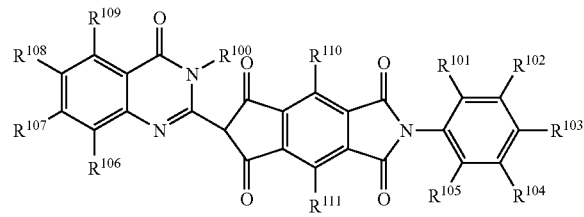

(10)

wherein $R^{100}$ represents hydrogen or substituted or unsubstituted alkyl, substituted or unsubstituted aralkyl or substituted or unsubstituted aromatic ring; $R^{101}$ to $R^{111}$ each independently represent a hydrogen or halogen atom; a group selected from nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthio, substituted or unsubstituted arylthio, substituted or unsubstituted amino, substituted or unsubstituted acyl, substituted or unsubstituted acytoxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenyfthio, substituted or unsubstituted heteroaryl, substituted or unsubstituted heteroaryloxy, substituted or unsubstituted heteroaryloxycarbonyl, heteroarylthio, or substituted or unsubstituted metallocenyl; or, in a combination of $R^{101}$ to $R^{105}$, and/or a combination of $R^{106}$ to $R^{109}$, two or more substituents selected from each of the combinations may independently combine via a linking group in the same combination to form a cyclic structure together with carbon atoms to which they are attached, with the proviso that any one or more groups selected from $R^{101}$ to $R^{105}$ represent substituted or unsubstituted metallocenyl groups.

3. The imide compound according to claim 1, wherein the imide compound having a quinazoline-4-on residue is represented by a general formula (11) as one of the tautomeric structures:

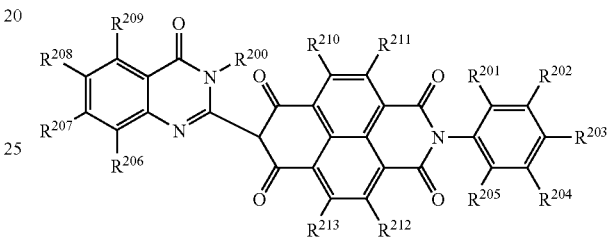

(11)

wherein $R^{200}$ represents hydrogen or substituted or unsubstituted alkyl, substituted or unsubstituted aralkyl, or substituted or unsubstituted aromatic ring; $R^{201}$ to $R^{213}$ each independently represent a hydrogen or halogen atom; a group selected from nitro, cyano, hydroxyl, mercapto, carboxyl, substituted or unsubstituted alkyl, substituted or unsubstituted aralkyl, substituted or unsubstituted aromatic ring, substituted or unsubstituted alkoxy, substituted or unsubstituted aralkyloxy, substituted or unsubstituted aryloxy, substituted or unsubstituted alkylthio, substituted or unsubstituted aralkylthia, substituted or unsubstituted arylthio, substituted or unsubstituted amino, substituted or unsubstituted acyl, substituted or unsubstituted acyloxy, substituted or unsubstituted alkoxycarbonyl, substituted or unsubstituted aralkyloxycarbonyl, substituted or unsubstituted aryloxycarbonyl, substituted or unsubstituted alkenyloxycarbonyl, substituted or unsubstituted aminocarbonyl, substituted or unsubstituted alkenyl, substituted or unsubstituted alkenyloxy, substituted or unsubstituted alkenylthio, substituted or unsubstituted heteroaryl, substituted or unsubstituted heteroaryloxy, substituted or unsubstituted heteroaryloxycarbonyl, heteroarylthio, or substituted or unsubstituted metallocenyl; or, in a combination of $R^{201}$ to $R^{205}$, and/or a combination of $R^{206}$ to $R^{209}$, and/or a combination of $R^{210}$ to $R^{211}$, and/or a combination of $R^{212}$ to $R^{213}$, two or more substituents selected from each of the combinations may independently combine via a linking group in the same combination to form a cyclic structure together with carbon atoms to which they are attached, with the proviso that any one or more groups selected from $R^{201}$ to $R^{205}$ represent substituted or unsubstituted metallocenyl groups.

* * * * *